(12) United States Patent
Coll Mulet et al.

(10) Patent No.: US 11,459,602 B2
(45) Date of Patent: Oct. 4, 2022

(54) METHOD FOR GENERATING DOUBLE STRANDED DNA LIBRARIES AND SEQUENCING METHODS FOR THE IDENTIFICATION OF METHYLATED CYTOSINES

(71) Applicants: Fundació Privada Institut De Medicina Predictiva I Personalitzada Del Cáncer, Badalona (ES); Llorenç Coll Mulet, Badalona (ES)

(72) Inventors: Llorenç Coll Mulet, Badalona (ES); Miguel A. Peinado Morales, Badalona (ES)

(73) Assignees: Fundadó Privada Institut De Medicina Predictiva I, Badalona (ES); Personalitzada Del Cáncer Llorenç Coll Mulet, Badalona (ES)

(*) Notice: Subject to any disclaimer, the term of this patent is extended or adjusted under 35 U.S.C. 154(b) by 0 days.

(21) Appl. No.: 16/133,842

(22) Filed: Sep. 18, 2018

(65) Prior Publication Data
US 2019/0177776 A1    Jun. 13, 2019

Related U.S. Application Data

(62) Division of application No. 15/110,110, filed as application No. PCT/EP2015/050182 on Jan. 7, 2015, now Pat. No. 10,260,087.

(30) Foreign Application Priority Data

Jan. 7, 2014    (EP) .................................... 14382002

(51) Int. Cl.
*C12Q 1/6806*    (2018.01)
*C12Q 1/6855*    (2018.01)
(Continued)

(52) U.S. Cl.
CPC .......... *C12Q 1/6827* (2013.01); *C07H 21/04* (2013.01); *C12N 15/1093* (2013.01);
(Continued)

(58) Field of Classification Search
CPC ................ C12Q 1/6806; C12Q 1/6855; C12Q 2525/301; C12Q 2525/191; C12Q 1/68;
(Continued)

(56) References Cited

U.S. PATENT DOCUMENTS

| 6,287,825 | B1 | 9/2001 | Weissman et al. |
| 10,260,087 | B2 | 4/2019 | Coll Mulet et al. |

(Continued)

FOREIGN PATENT DOCUMENTS

| JP | 2011-516031 A | 5/2011 |
| RU | 2332462 C2 | 8/2008 |

(Continued)

OTHER PUBLICATIONS

Zheng et al. Nature Protocols. 2011. 6(9):1367. (Year: 2011).*

(Continued)

*Primary Examiner* — Joseph G. Dauner
(74) *Attorney, Agent, or Firm* — Wolf, Greenfield & Sacks, P.C.

(57) ABSTRACT

The present invention relates to methods for the identification of methylated cytosines in a population of double stranded DNA molecules. The invention also relates to adapters and kits for synthesizing said adapters as well as to double stranded DNA libraries obtained by the methods of the invention.

9 Claims, 16 Drawing Sheets

Specification includes a Sequence Listing.

(51) Int. Cl.
   *C12Q 1/6827* (2018.01)
   *C12N 15/10* (2006.01)
   *C07H 21/04* (2006.01)

(52) U.S. Cl.
   CPC ......... *C12Q 1/6806* (2013.01); *C12Q 1/6855* (2013.01); *Y02P 20/582* (2015.11)

(58) Field of Classification Search
   CPC ............ C12Q 1/6827; C12Q 2523/125; C12N 15/1093
   See application file for complete search history.

(56) References Cited

U.S. PATENT DOCUMENTS

| | | | |
|---|---|---|---|
| 2004/0197791 A1 | 10/2004 | Makarov et al. | |
| 2009/0148842 A1 | 6/2009 | Gormley et al. | |
| 2009/0275087 A1 | 11/2009 | Mikawa | |
| 2011/0003701 A1* | 1/2011 | Ferreri | C12N 15/66 506/9 |
| 2011/0319290 A1* | 12/2011 | Raymond | C12Q 1/6855 506/9 |
| 2013/0079231 A1* | 3/2013 | Pushkarev | C12Q 1/6874 506/2 |
| 2013/0231253 A1* | 9/2013 | Amorese | C12N 15/66 506/2 |
| 2017/0002404 A1 | 1/2017 | Coll Mulet et al. | |

FOREIGN PATENT DOCUMENTS

| | | |
|---|---|---|
| WO | WO 2009/106308 A2 | 9/2009 |
| WO | WO 2009/132315 A1 | 10/2009 |
| WO | WO 2010/048337 A2 | 4/2010 |

OTHER PUBLICATIONS

Office Communication dated Dec. 4, 2018 for Japanese Application No. 2016-546043.

[No Author Listed] NEXTflexTM Bisulfite-Seq Barcodes-6 (Illumina compatible) Catalog #:511911. Jan. 1, 2012. Retrieved from http://search.cosmobio.co.jp/cosmo_search_p/search_gate2/docs/BIO_/511911.20120924.pdf on Oct. 4, 2016.

Chen et al., Generation and analysis of a barcode-tagged insertion mutant library in the fission yeast *Schizosaccharomyces pombe*. BMC Genomics. 2012;13:161 and Fig. S3.

Clark et al., High sensitivity mapping of methylated cytosines. Nucleic Acids Res. Aug. 11, 1994;22(15):2990-7.

Hayatsu, The bisulfite genomic sequencing used in the analysis of epigenetic states, a technique in the emerging environmental genotoxicology research. Mutat Res. Jul.-Aug. 2008;659(1-2):77-82. doi: 10.1016/j.mrrev.2008.04.003. Epub May 14, 2008.

Hodges et al., High definition profiling of mammalian DNA methylation by array capture and single molecule bisulfite sequencing. Genome Res. Sep. 2009;19(9):1593-605. doi:10.1101/gr.095190.109. Epub Jul. 6, 2009.

Laird et al., Hairpin-bisulfite PCR: assessing epigenetic methylation patterns on complementary strands of individual DNA molecules. Proc Natl Acad Sci USA. Jan. 6, 2004;101(1):204-9. Epub Dec. 12, 2003.

Laird, Principles and challenges of genomewide DNA methylation analysis. Nat Rev Genet. Mar. 2010;11(3):191-203. doi: 10.1038/nrg2732.

Lister et al., Finding the fifth base: genome-wide sequencing of cytosine methylation. Genome Res. Jun. 2009;19(6):959-66. doi: 10.1101/gr.083451.108. Epub Mar. 9, 2009.

Miner et al., Molecular barcodes detect redundancy and contamination in hairpin-bisulfite PCR. Nucleic Acids Res. Sep. 30, 2004;32(17):e135.

Monson-Miller et al., Reference genome-independent assessment of mutation density using restriction enzyme-phased sequencing. BMC Genomics. Feb. 14, 2012;13:72. doi:10.1186/1471-2164-13-72.

Patterson et al., DNA methylation: bisulphite modification and analysis. J Vis Exp. Oct. 21, 2011;(56). pii: 3170. doi: 10.3791/3170.

Riggs et al., Methylation and epigenetic fidelity. Proc Natl Acad Sci USA. Jan. 6, 2004;101(1):4-5. Epub Dec. 26, 2003.

Shapiro et al., Nucleic acid reactivity and conformation. II. Reaction of cytosine and uracil with sodium bisulfite. J Biol Chem. Jun. 10, 1973;248(11):4060-4.

Shiroguchi et al., Digital RNA sequencing minimizes sequence-dependent bias and amplification noise with optimized single-molecule barcodes. Proc Natl Acad Sci USA. Jan. 24, 2012;109(4):1347-52. doi:10.1073/pnas.1118018109. Epub Jan. 9, 2012.

Uren et al., A high-throughput splinkerette-PCR method for the isolation and sequencing of retroviral insertion sites. Nat Protoc. 2009;4(5):789-98. doi: 10.1038/nprot.2009.64. Epub Apr. 30, 2009.

Urich et al., MethylC-seq library preparation for base-resolution whole-genome bisulfite sequencing. Nat Protoc. Mar. 2015;10(3):475-83. doi: 10.1038/nprot.2014.114. Epub Feb. 18, 2015.

Wang et al., Tagmentation-based whole-genome bisulfite sequencing. Nat Protoc. Oct. 2013;8(10):2022-32. doi:10.1038/nprot.2013.118. Epub Sep. 26, 2013.

\* cited by examiner

METHOD FOR GENERATING DOUBLE STRANDED DNA LIBRARIES AND SEQUENCING METHODS FOR THE IDENTIFICATION OF METHYLATED CYTOSINES

RELATED APPLICATIONS

This application is a divisional application of Ser. No. 15/110,110, filed Jul. 7, 2016, which is a national stage filing under 35 U.S.C. § 371 of International Application PCT/EP2015/050182, filed Jan. 7, 2015, which was published under PCT Article 21(2) in English, the entire contents of each of which are incorporated by reference herein in its entirety.

FIELD OF THE INVENTION

The present invention relates to methods for determining the sequence of a population of double stranded DNA molecules and for the identification of methylated cytosines in a population of double stranded DNA molecules. The invention also relates to adapters and kits for synthesizing said adapters as well as to double stranded DNA libraries that are useful in the methods of the invention.

BACKGROUND OF THE INVENTION

Analysis of the primary structure of nucleic acids (as DNA and RNA) including epigenetic modifications (i.e. DNA methylation) can be addressed with the use of different techniques commonly termed "sequencing".

All methods currently available do not analyse directly the original material. They require the processing or conversion of the original template, the generation of a replica and often the amplification of the replica. The generated replicas (named genomic libraries) are suitable to be sequenced by using one or many of the currently available sequencing technologies (e.g. Illumina, Roche or IonTorrent sequencing platforms).

The sequencing can be performed either at the low scale, which consists in the analysis of selected fragments, or high throughput (also named genome-scale), which consists in the massive analysis of all or a large representation of the whole material. The length of the fragment that can be analysed depends on the sequencing methodology used. Current state of the art sequencing techniques aiming the genomic scale and most of the locus specific assess DNA strands separately.

The current Gold Standard for the assessment of DNA methylation implies the chemical transformation with bisulfite of the nucleic acids, which results in the generation of ambiguity, as non-methylated cytosines will be transformed to uracils and visualized as thymines, which makes them indistinguishable from actual thymines in every sequencing method. This reduction of information represents a challenge to genome-scale approaches since there are some drawbacks which are still unsolved and limit their applications, for example:
1) independent processes must be used to determine the primary sequence (i.e. for the detection of mutations or genetic variants) and the epigenetic modifications (i.e. methylation of cytosines);
2) the generated ambiguity limits the efficiency (a large proportion of sequence reads are discarded as ambiguous) and coverage (some regions cannot be analysed) and involves a demanding computational processing;
3) high amounts of starting material are required to perform studies with high coverage;
4) uncontrolled biases limit the quantitative determination; and
5) sequencing errors are hardly detected by the system.

Another method is the so-called hairpin-bisulfite PCR method (see Laird et al., 2004, Proc. Natl. Acad. Sci. USA 101, 204-209; Riggs and Xiong, 2004, Proc. Natl. Acad. Sci. USA 101, 4-5). In this method, prior to the bisulfite treatment, the two complementary strands are covalently linked by means of a hairpin loop sequence. However, this method is suitable only for a specific double-stranded molecule and not for determining the sequence of a population of double stranded DNA molecules and particularly for the identification of methylated cytosines in a population of double stranded DNA molecules.

It has therefore been of interest to develop further methods for determining the sequence of a population of double stranded DNA molecules and particularly for the identification of methylated cytosines in a population of double stranded DNA molecules which are capable of solving all or some of the above mentioned drawbacks related to the methods of the state of the art.

WO2010/048337 discloses a method for identifying methylated cytosines comprising the steps of generating a complementary copy of a template nucleic acid using a bisulfite-resistant cytosine analog, optionally pairing the template nucleic acid and the complementary copy, converting non-methylated cytosine residues in the template nucleic acid and the complementary copy to uracil residues, and determining the nucleotide sequence of the bisulfite-converted template nucleic acid and the non-converted complementary copy. Since both the bisulfite-converted template nucleic acid and the non-converted complementary copy are rich in methylated cytosines, these strands are however difficult to process.

The present invention addresses these problems.

SUMMARY OF THE INVENTION

The present invention relates to a method for the identification of methylated cytosines in a population of double stranded DNA molecules comprising the steps of
  (i) Ligating double-stranded DNA adaptors to at least one end of the strands of a plurality of double-stranded DNA molecules and pairing the strands of a plurality of double-stranded DNA molecules to provide a plurality of paired adaptor-modified DNA molecules;
  (ii) Transforming any (non-methylated) cytosine in the paired adaptor-modified DNA molecules to uracil in the paired adaptor-modified DNA molecules;
  (iii) Providing complementary strands of the paired and transformed adaptor-modified DNA molecules using the nucleotides A, G, C and T and primers the sequences of which are complementary to at least a portion of the double-stranded adaptors to provide partially transformed paired double-stranded molecules;
  (iv) Optionally amplifying the partially transformed paired double stranded DNA molecules obtained in step (iii) to provide amplified paired double stranded DNA molecules;
  (v) Sequencing the paired DNA molecules obtained in step (iii) or in step (iv),
wherein the presence of methylated cytosine at a given position is determined if a cytosine appears in one of the strands of the paired double stranded DNA molecules obtained in step (iii) or in step (iv) and a guanine appears in the corresponding position in the other strand of the paired double stranded DNA molecules, and/or wherein the presence of an non-methylated cytosine at a given position is determined if a uracil or thymine appears in one of the strands of the paired double stranded DNA molecules obtained in step (iii) or in step (iv) and a guanine appears in the corresponding position in the other strand of the paired double stranded DNA molecules.

and the synthetic sequence (B) of each amplified product that are joined by the hairpin adapter (C) is shown.

Figure 13:
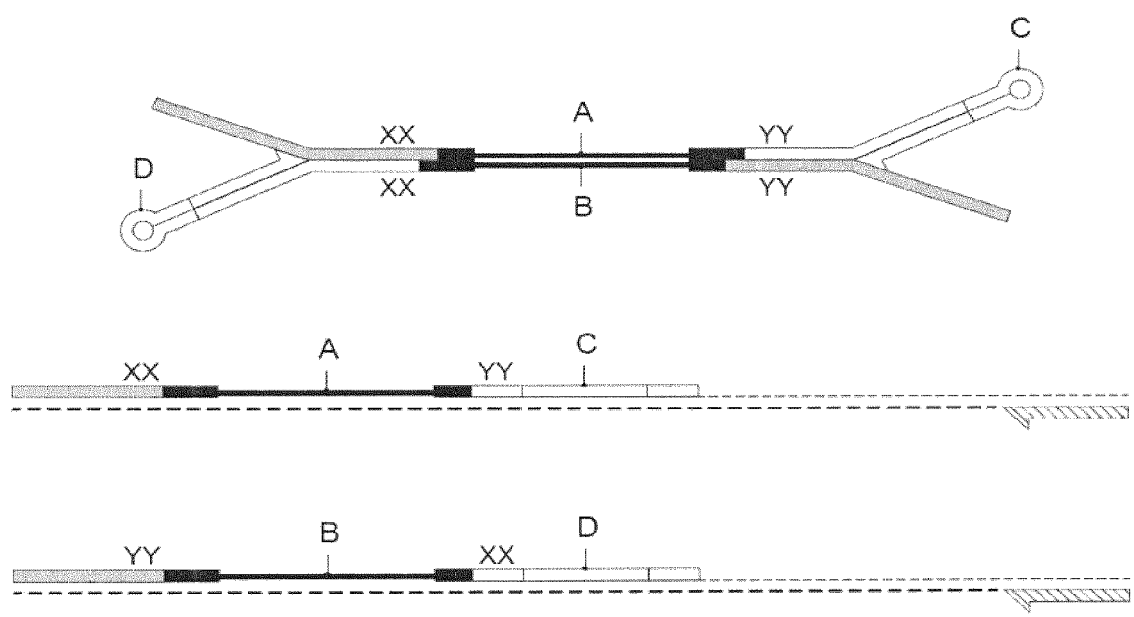

FIG. 13. Schematic diagram showing several embodiments of the method of the invention wherein the adapters (C and D) comprise a different combinatorial sequence. Combinatorial barcodes (YY, XX, respectively) allow the unique labeling of the molecule. After the whole process, those complementary strands that were originally together will share the same two barcodes. This allows keeping track of both strands (A and B) of each double stranded DNA fragment.

Figure 14:
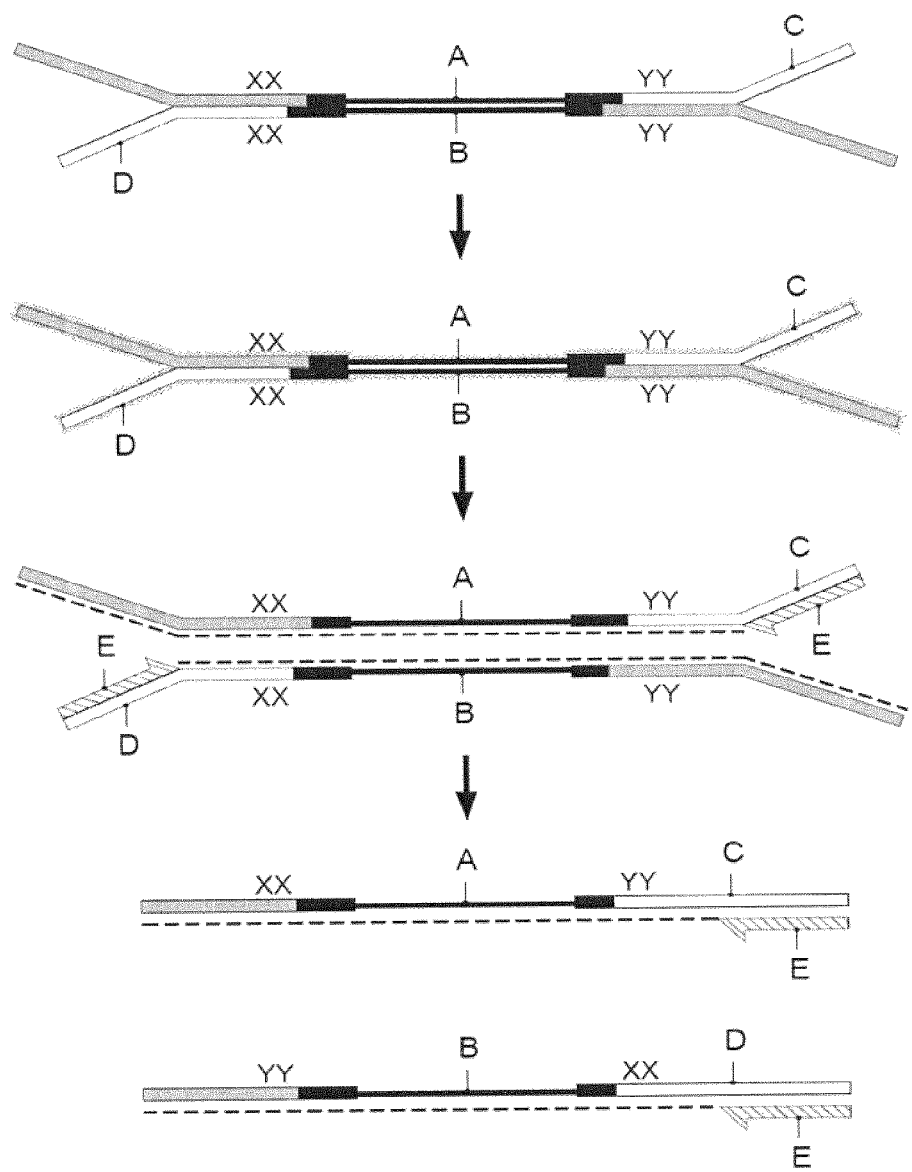

FIG. 14. Schematic diagram showing an embodiment of the method of the invention wherein the adapter is an Y-adapter. Ligation step [step (i)]. Genomic fragments (black line; A, B) from the sample preparation step are ligated to two Y-adapters (C, D), each formed by a first DNA strand (grey) and a second DNA strand (white), wherein the adapters comprise a different dsDNA combinatorial sequence (XX and YY, respectively). Bisulfite step [step (ii)]. The molecules obtained after the ligation step are bisulfite treated and the complementarity of the strands is lost (glow). Complementary strand generation step (elongation step)[step (iii)]. Primer (E) is added for the first round of amplification (dotted line). Combinatorial barcodes allow the unique labeling of the molecule. After the whole process, those complementary strands that were originally together will share the same two barcodes. This allows keeping track of both strands (A and B) of each double stranded DNA fragment.

Figure 15:
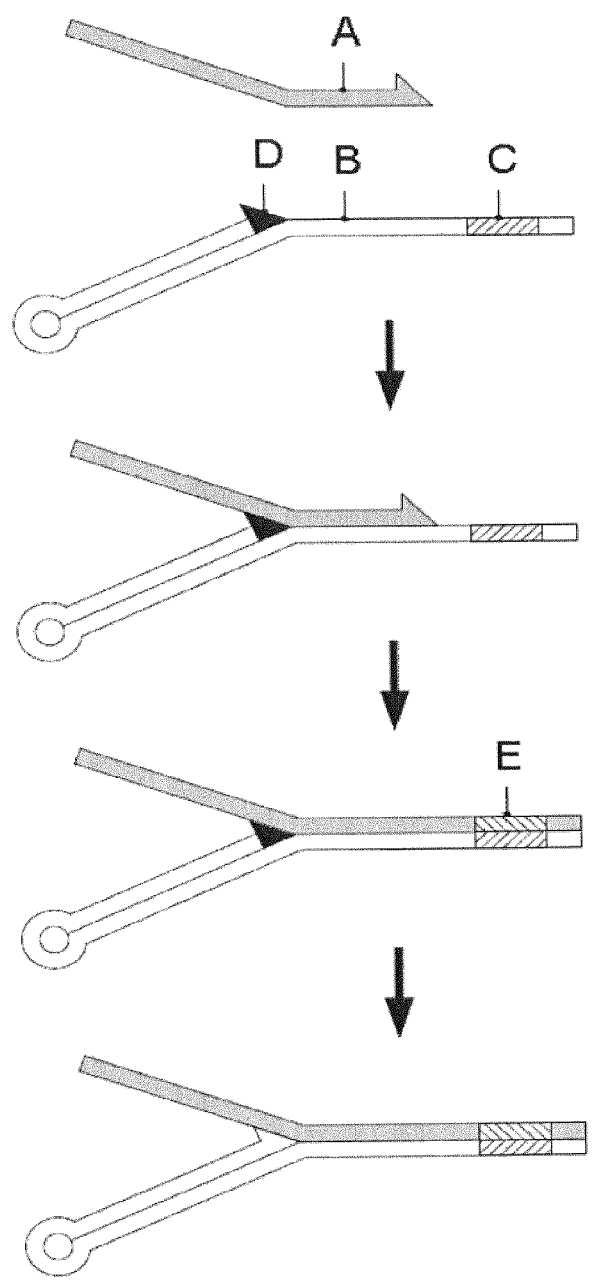

FIG. 15. Schematic diagram showing a method for producing a DNA Y-adapter containing a combinatorial sequence. Hybridization step. A first single stranded polynucleotide (A) is contacted with a second single stranded polynucleotide (B), wherein said second polynucleotide has a combinatorial sequence (C) and is reversibly blocked (black triangle; D) in the 3' end. Elongation step. The 3' end of the first polynucleotide is elongated to generate a sequence (E) complementary to the 5' region of the second polynucleotide. Unblocking step. The 3' end of the second polynucleotide is unblocked (white triangle).

Figure 16:
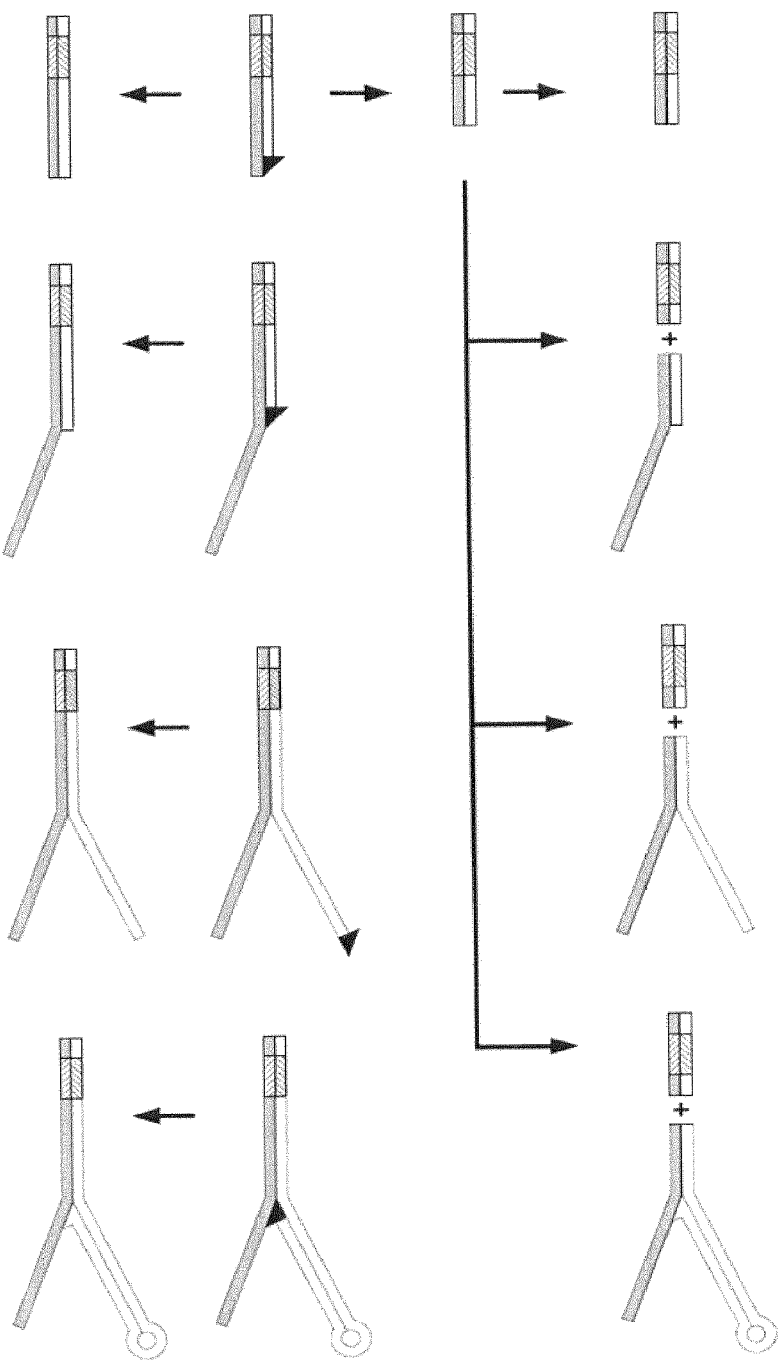

FIG. 16. Schematic diagram showing exemplary adapters comprising a combinatorial sequence for use in the method of the invention and their method of synthesis. Protocol for generating different Y-adapters according to several embodiments of the present invention.

DETAILED DESCRIPTION OF THE INVENTION

The present invention relates to a method for the identification of methylated cytosines in a population of double stranded DNA molecules. This method in any of the described embodiments ensures sequence fidelity and increases the quality of sequencing because both strands of the same DNA molecule are read at the same time and error and bias control are exhaustive.

In addition, due to the more accurate sequencing, less coverage is needed to obtain reliable readings, and less starting material is required. Specifically, the double stranded DNA libraries generated by the method of the invention can be generated from small amounts of DNA and a wide source of sample preparations, including those that involve DNA fragmentation.

The method of the invention in any of the described embodiments provides the further advantage that the sample used as a DNA template may be preserved during the process, and it may be recovered, stored and submitted to multiple amplifications with different conditions and multiple sequencings without sample exhaustion. Particularly, the adapter and/or hairpin sequences and/or barcode sequences, as the case may be, used in the method of the invention in any of the described embodiments may have unique barcodes (also referred to as barcode sequences, combinatorial sequences or combinatorial barcodes) for sample identification and functional groups to allow the recovery of the original DNA template after the elongation or amplification step. The barcodes may also be present as separate molecules, as described below.

The method of the present invention in all its embodiments is particularly useful for sequencing methylated sequences. The double stranded DNA libraries generated by the method of the invention retain unambiguous DNA sequence and DNA methylation information, allowing the simultaneous detection of sequence variations (including polymorphisms and mutations) and DNA methylation modifications. Particularly, since both strands are concurrently analyzed, the method of the invention allows the determination of DNA methylation symmetry at the genome scale. By reading both strands, the sequencing process can be monitored and the errors produced in every individual sequence read can be corrected, thus obtaining more reliable information for both the genome and the methylome.

Furthermore, quantitative results for sequence variants (including polymorphisms and mutations) and for DNA methylation modifications may be obtained by introducing combinatorial barcodes in the DNA templates. Said barcodes allow monitoring every library for biases introduced during the processing of the sample (i.e. heterogeneous degradation of the DNA) and amplification (i.e. different amplification efficiency for sequence variants). In order to achieve this goal, the present invention provides a method for synthesizing combinatorial barcode DNA adapters with ultrahigh efficiency.

Furthermore, the invention also provides the generation of libraries and the sequencing of methylated sequences wherein the adapters used include a unique combinatorial barcode that allows keeping track of the sense and antisense strands of the original DNA molecule. In summary, the whole process of obtaining a DNA library and sequencing it by the method of the invention is less labor intensive, both hand work and computationally, and less expensive than using the methods of the state of the art. It allows for the identification of methylated cytosines in both strands of the original double-stranded DNA molecules, preferably genomic DNA.

The invention relates to a method for the identification of methylated cytosines in a population of double stranded DNA molecules comprising the steps of
 (i) Ligating double-stranded DNA adaptors to at least one end of the strands of a plurality of double-stranded DNA molecules and pairing the strands of a plurality of double-stranded DNA molecules to provide a plurality of paired adaptor-modified DNA molecules;
 (ii) Transforming (non-methylated) cytosine present in both strands of the paired adaptor-modified DNA molecules to uracil in the paired adaptor-modified DNA molecules;
 (iii) Providing complementary strands of the paired and transformed adaptor-modified DNA molecules using the nucleotides A, G, C and T and primers the sequences of which are complementary to at least a portion of the double-stranded adaptors (as obtained after the transformation step (ii)) to provide partially transformed paired double-stranded molecules;

(iv) Optionally amplifying the partially transformed paired double stranded DNA molecules obtained in step (iii) to provide amplified paired double stranded DNA molecules;
(v) Sequencing the paired DNA molecules obtained in steps (ii), (iii) or in step (iv) (preferably in step (iii) and/or in step (iv)),
wherein the presence of methylated cytosine at a given position is determined if a cytosine appears in one of the strands of the paired double stranded DNA molecules obtained in step (iii) or in step (iv) and a guanine appears in the corresponding position in the other strand of the paired double stranded DNA molecules, or wherein the presence of an non-methylated cytosine at a given position is determined if a uracil or thymine appears in one of the strands of the paired double stranded DNA molecules obtained in step (iii) or in step (iv) and a guanine appears in the corresponding position in the other strand of the paired double stranded DNA molecules.

The method of the invention allows obtaining double stranded DNA libraries wherein the original sense and antisense strands of a DNA molecule may be physically bound (if the pairing occurs via a hairpin molecule, as described below) after steps (i), (ii), (iii) and, optionally, (iv). A schematic diagram of the method of the invention is showed in FIG. 1.

The term "DNA library", as used herein, may refer to a collection of DNA fragments that have been ligated to adapter molecules in order to identify and isolate the DNA fragments of interest.

The expression "double stranded DNA library", as used herein, may refer to a library that contains both strands of a molecule of DNA (i.e. the sense and antisense strands) which may be physically joined by one of their ends and forming part of the same molecule. The strands of the double-stranded DNA molecules of the DNA library may also not be physically joined by one of their ends. They may be paired by the presence of barcode sequences, as described below. The double stranded DNA library of the method of the invention is not a circular library. The original strands of the DNA molecule may be physically joined by one of their ends by a loop thus forming a duplex between the sense and antisense strand. Each molecule of the double stranded DNA library may also be in linear conformation when complementarity between the sense and antisense strands of the DNA molecule is partially or completely lost. In addition, the original strands of the DNA molecule may not be physically joined by one of their ends, but paired through the presence of at least one barcode sequence.

The method of the invention requires a population or plurality of double stranded DNA molecules. The "population or plurality of double stranded DNA molecules", as used herein, is a collection of double stranded DNA molecules that may be, without limitation, genomic DNA (nuclear DNA, mitochondrial DNA, chloroplast DNA, etc.), plasmid DNA or double stranded DNA molecules obtained from single stranded nucleic acid samples (e.g. DNA, cDNA, mRNA). In an embodiment said population is formed by fragments of DNA.

Preferably, the plurality of double stranded DNA molecules is genomic DNA. This can be the whole genome or a reduced representation of the genome. Said DNA may be obtained for example, by enrichment or by chromatin immunoprecipitation (ChiP).

The term "genomic DNA" refers to the heritable genetic information of an organism. The genomic DNA comprises the DNA of the nucleus (also referred to as chromosomal DNA) but also the DNA of the plastids (e.g. chloroplasts) and other cellular organelles (e.g. mitochondria). The term "genomic DNA" contemplated in the present invention includes the genomic DNA containing sequences complementary to those described herein.

Preferably, the plurality of double stranded DNA molecules are fragments of DNA. The DNA is fragmented through any suitable method including, but not limited to, mechanical stress (sonication, nebulization, cavitation, etc.), enzymatic fragmentation (enzyme digestion with restriction endonucleases, nicking endonucleases, exonucleases, etc.) and chemical fragmentation (dimethyl sulfate, hydrazine, NaCl, piperidine, acid, etc.). In principle, there is no restriction on the length of the DNA fragments after fragmentation, though it is preferable to have a narrow range of lengths. The suitable size of fragments may be selected prior to step (i) of the first method of the invention. The optimal length will ultimately depend on the available sequencing methods. In a more preferred embodiment the double stranded DNA molecules are fragments of genomic DNA.

The plurality of double-stranded DNA molecules used in step (i) may be obtained by:
a) Providing a population of double stranded DNA molecules derived from genomic DNA;
b) Separating the double stranded molecules derived from genomic DNA to provide single stranded DNA molecules derived from genomic DNA;
c) Providing complementary strands of the single stranded DNA molecules derived from genomic DNA using the nucleotides A, G, C and T to obtain the double-stranded DNA molecules used in step (i).

Preferably, the plurality of double stranded DNA molecules to which the adaptors are ligated comprise DNA molecules containing (non-methylated) cytosine in both strands and/or no methylated cytosine in one of the strands.

Usually the ends of the population of double stranded DNA molecules are processed so that the sample can enter the specific protocol of the sequencing platform.

Optionally, the double-stranded DNA adaptors may contain "sites for cutting" (e.g. "restriction sites", sequences of oligonucleotides that are recognized by restriction enzymes). The "sites for cutting" add a way to adapt the final elements of the library to the needs of the different sequencing platforms. Although this adaptation can be achieved through the specific design of the double-stranded DNA adaptors (by introducing sequences that are compatible with the platform reagents, such as sequencing primers), the cutting sites allow modularity, to add barcodes or adapters for multiplexing (mixing sample from different origins) or for the needs of any of the platforms for massive sequencing (or also to eliminate possibly unnecessary nucleotides). The "sites for cutting" are specific sequences that allow the presence of a known target in the edges of the plurality of paired adaptor-modified DNA molecules (library of paired adaptor-modified DNA molecules obtained in step (i), or a library of paired and transformed adaptor-modified DNA molecules as obtained in step (iii) (and optionally in step (iv)). The "sites for cutting" may be ligated to the plurality of double-stranded DNA molecules before or after the step of ligating the adapters and/or hairpin sequences and/or barcode sequences. As stated above, the "sites for cutting" may be already included in the adaptors and/or hairpin sequences and/or barcode sequences. This way, all fragments can be cut and adapters can be ligated properly (this way sequences of the adaptors and/or hairpin sequences and/or barcode sequences that are no longer required may be removed to increase sequencing efficiency).

Preferably, the double stranded DNA molecules used in step (i) are end-repaired prior to step (i).

The term "end-repaired", as used herein, refers to the conversion of the DNA fragments that contain damaged or incompatible 5'- and/or 3'-protruding ends into blunt-ended DNA containing a 5'-phosphate and 3'-hydroxil groups. The blunting of the DNA ends can be achieved by enzymes including, without limitation, T4 DNA polymerase (having 5'→3' polymerase activity that fills-in 5' protruded DNA ends) and the Klenow fragment of E. coli DNA polymerase I (having 3'→5' exonuclease activity that removes 3'-overhangs). For efficient phosphorylation of DNA ends any enzyme capable of adding 5'-phosphates to ends of unphosphorylated DNA fragments can be used, including, without limitation, T4 polynucleotide kinase.

Preferably, the method of the invention further comprises a step of dA-tailing the DNA molecules after the end-repairing step.

The term "dA-tailing", as used herein, refers to the addition of an A base to the 3' end of a blunt phosphorylated DNA fragment. This treatment creates compatible overhangs for subsequent ligation. This step is performed by methods well known by the person skilled in the art by using, for example, the Klenow fragment of E. coli DNA polymerase I.

The plurality of double stranded DNA used as starting material in the methods of the invention may also be obtained from synthesis from a single stranded DNA or cDNA. The population of double stranded DNA molecules may be obtained from cDNA. The double stranded DNA may also be obtained from mRNA (for example from the RNA of a virus) by methods well known in the state of the art that comprise the isolation of the mRNA, reverse transcription of the RNA to yield single stranded cDNA and treating the single-stranded DNA to obtain double-stranded DNA.

The sample used for obtaining the plurality of double stranded DNA molecules can be from a biological or environmental source. Biological samples include, without limitation, animal or human samples, liquid and solid food and feed products (dairy items, vegetables, meat, etc.). Preferred biological samples include, without limitation, any biological fluid, cell, tissue, organ or portion thereof that contains DNA or mRNA. A biological sample can include a neoplastic cell, such as a cell from the colon, rectum, breast, ovary, prostate, kidney, lung, blood, brain or other organ or tissue. Any organism can be used as a source and includes, but is not restricted to, bacteria, fungi, viruses, plants, animals, e.g. human beings, non-human primates, reptiles, insects, birds, worms, fish, mammals, domestic and farm animals (cows, horses, pigs, sheep, goats, dogs, cats, rodents, etc.). Environmental samples include, without limitation, surface matter, soil, water and industrial samples, as well as samples obtained from food and dairy processing instruments. The sample being analyzed can be derived from a single source (e.g. a single organism, tissue, cell, etc.) or be a pool of nucleic acids from a plurality of organisms, tissues or cells.

Step (i)

In a first step, the method for the identification of methylated cytosines in a population of double stranded DNA molecules of the invention involves ligating double-stranded DNA adaptors to at least one end of the strands of a plurality of double-stranded DNA molecules. Preferably, the double-stranded DNA adaptors may be ligated to one end of the strands of a plurality of double-stranded DNA molecules. Alternatively, the double-stranded DNA adaptors may be ligated to both ends of the strands of a plurality of double-stranded DNA molecules.

The terms "adapter" and "adaptor" are used interchangeably and refer to an oligonucleotide or nucleic acid fragment or segment that can be ligated to a nucleic acid molecule of interest.

The "adapter molecule" of the method of the invention is a double stranded DNA molecule having ends at one end which are compatible with the ends of the double stranded DNA. The adapter molecule may be formed by a first DNA strand and a second DNA strand that are substantially complementary. The adapter molecule may be a Y-adapter wherein the 3' region of the first DNA strand and the 5' region of the second DNA strand form a double stranded region by sequence complementarity and wherein the 5' region of the first DNA strand and the 3' region of the second DNA strand are not complementary.

In one embodiment, at least one portion of the double-stranded adaptors has sequences common to all the double-stranded adaptors used in step (i). In this case, identical primers for the generation of complementary strands of the paired and transformed adaptor-modified DNA molecules in step (iii), and/or the amplification step (iv) could be used.

Optionally, the adapters include unique and combinatorial barcodes (also referred to "combinatorial sequences" or "barcodes" or "barcode sequences" or "combinatorial labelling") that allow sample identification, multiplexing, pairing as well as quantitative analysis. The constructs obtained by the methods of the invention have barcodes that allow generating unique identifiers associated with the initial construct, thus giving the ability to differentiate between constructs. Said unique identifiers allow identification of a specific construct comprising said identifier and its descendants. Each unique identifier is associated with an individual molecule in the starting sample. Therefore, any amplification products of said initial individual molecule bearing the unique identifier are assumed to be identical by descent. The combinatorial barcodes also allow quantifying the percentage of individual sequences within a sample and are useful for monitoring biases and error control during the amplification steps.

The barcodes sequences add the feature of 'bias control'. When amplification occurs, some fragments may become selectively amplified for a number of reasons. This undesirable effect is a major problem for quantification purposes, which is critical in many applications for sequencing, specially for the analysis of methylation status of the DNA (since each allele in each cell can have different methylation status, and even samples can have heterogeneous compositions, which make the quantification and bias control a must for most applications). Accordingly, the presence of at least one barcode sequence allows the possibility of having a bias control. Since each double-stranded DNA molecule from the plurality of double-stranded DNA molecules may have one or more different barcode sequence(s), it may be possible to perform a bias control and detect the selective amplification of a given double-stranded or single-stranded DNA molecule.

Currently, sequencing machines have error rates that need to be assumed. Most of these errors cannot be depicted and remain hidden in the final results. This has negative consequences on the subsequent processing and analyzing of the results. The method of the invention provides up to four sources of information for each nucleotide (the top and bottom strands of a given dsDNA and, as the case may be, their respective synthetic complementary strands) allowing the validation of the reading of each nucleotide, as all readings must be consistent. Thus, the method of invention allows detection and even correction of errors of the sequence determination (both for primary sequence determination and for methylation of cytosines analysis).

Preferably, the adapter molecules and/or hairpin sequences and/or barcode sequences are provided, respectively, as a library of molecules, wherein each member in the library is distinguishable from the others by a combinatorial sequence within the sequence, as described below.

The term "library of adapter molecules and/or hairpin sequences and/or barcode sequences" and/or "combinatorial labelling", as used herein, refers to a collection of adapter molecules and/or hairpin sequences and/or barcode sequences wherein each member of the collection is distinguishable from the others by a combinatorial sequence within the adapter and/or hairpin sequences and/or barcode sequences.

The terms "combinatorial sequence", "barcode sequence", "barcode" and "combinatorial barcode" are used interchangeably all along the present description and refer to an identifier unique to the individual adapter/hairpin sequence or a separate DNA molecule (barcode sequence on its own, not belonging to the adapter and/or hairpin sequence). Preferably, the barcode sequence is included in the adapter and/or hairpin sequence. In an embodiment, the combinatorial sequence within the adapter sequence/hairpin sequence is a degenerate nucleic acid sequence. The combinatorial sequence may contain any nucleotide, including adenine, guanine, thymine, cytosine, methylated cytosine and other modified nucleotides. The number of nucleotides in the combinatorial sequence is preferably designed such that the number of potential and actual sequences represented by the combinatorial sequence is greater than the total number of adapters in the library. The combinatorial sequence may be located in any region of the adapter/hairpin sequence. Preferably, it is located within the double stranded region of the adapter/hairpin sequence.

Optionally, the adapter/hairpin sequence/barcode sequence incorporate bases labeled with the second member of a binding pair as described hereinafter that allow the recovery of the original DNA template after the elongation or amplification steps. This provides the advantage that the sample used as a DNA template is preserved during the process and the original DNA template formed by the sense and antisense strands can be recovered, stored and submitted to multiple amplifications with different conditions and sequencings without sample exhaustion. A schematic diagram of the method of the invention is showed in FIG. 1.

In the first step (i), the method for the identification of methylated cytosines in a population of double stranded DNA molecules of the invention further involves pairing the strands of a plurality of double-stranded DNA molecules to provide a plurality of paired adaptor-modified DNA molecules.

The "pairing step" of the first step of the method of the invention may be performed by covalently coupling the strands of one or more double-stranded DNA molecules with hairpin sequences (also referred to as "hairpin molecules" or "hairpin adapters"). The "pairing step" of the first step of the method of the invention may be performed by using barcode sequences. The "pairing step" of the first step of the method of the invention may be performed by using both hairpin sequences and barcode sequences.

For example, the "pairing step" of the first step of the method of the invention may be achieved through a hairpin sequence. The hairpin sequence may comprise a hairpin loop region and a double stranded region, wherein said double stranded region contains ends which are compatible with the ends of the double stranded DNA molecules (and/or with the ends of the barcode sequences, if they have been already ligated to the DNA strands). The pairing step may thus be performed by covalently coupling the strands of one or more double-stranded DNA molecules with a hairpin sequence. The hairpin sequence may also contain one or more barcode sequences.

Figure 1:
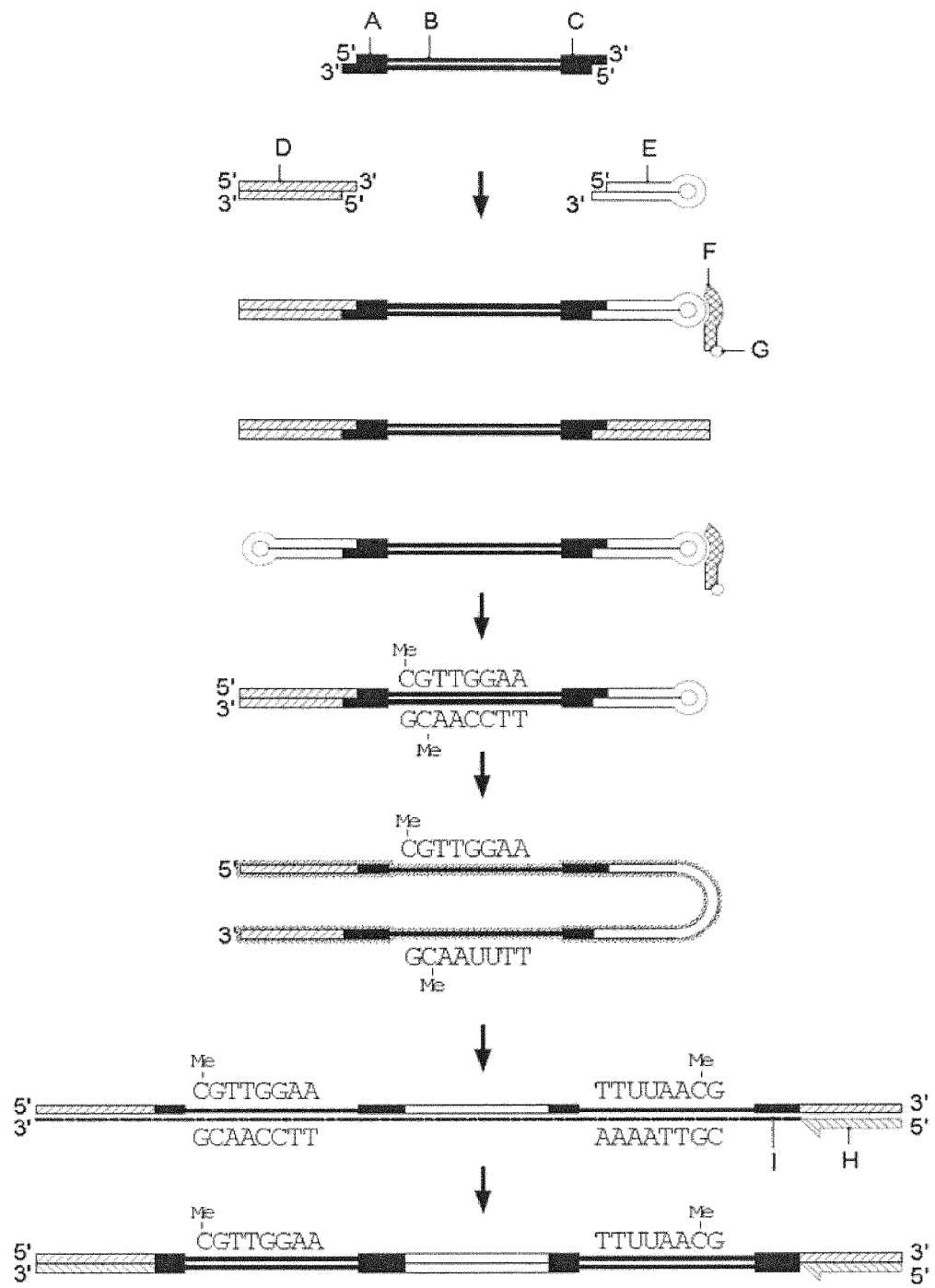
FIG. 1. Schematic diagram showing one embodiment of the method of the invention. Ligation step [step (i)]. Genomic fragments (black line; B) from the sample preparation step having overhanging ends (A and C) are ligated to two molecules: a dsDNA (adapter; D) and a hairpin (E). Capture step. A probe (F) marked with biotine (G) hybridizes with the hairpin to remove ligation products that do not contain the hairpin. Bisulfite and elongation step [step (iii)]. The ligation products are bisulfite treated and the complementarity is lost (glow). This allows the primer (H) to prime for polymerase extension (dashed line; I), with the subsequent amplification steps (not shown). An exemplary sequence fragment of the genomic fragment B is shown. The nucleotide sequence C*GTTGGAA and its complementary sequence TTCCAAC*G are treated with bisulfite and TTCCAAC*G is converted to TTUUAAC*G. After the amplification step, nucleotide sequences CGTTAAAA and TTCCAACG are obtained. C*: methylated cytosine.

In this case, double stranded DNA libraries wherein the original sense and antisense strands of a DNA molecule are physically bound are obtained (see e.g. FIG. 1).

The term "pairing sequences" or "pairing molecules" may be used in the context of the present invention to refer to sequences suitable for pairing the strands of one or more double-stranded DNA molecules. For example, "pairing sequences" may refer to hairpin sequences and/or to one or more barcode sequences. The term "hairpin sequence" (or "hairpin molecule" or "hairpin adapter"), as used in the method of the invention, refers to a duplex formed by a single-stranded nucleic acid that doubles back on itself to form a double stranded region maintained by base-pairing between complementary base sequences on the same strand. Said hairpin molecule also comprises a hairpin loop region formed by unpaired bases. The hairpin sequence is located in an opposite end of the double-stranded DNA molecules with respect to the location of the double-stranded DNA adaptor in the double-stranded DNA molecules.

Optionally, the "pairing step" of the first step (step (i)) of the method of the invention may be achieved through the use of barcodes (also referred to as "barcode sequences", "combinatorial sequence" and/or "combinatorial barcode" and/or "barcodes" and/or "combinatorial labelling", as described above). The pairing step may thus be performed by using barcode sequences.

The "combinatorial sequence", "combinatorial barcode", "barcode sequences" or "barcodes" used for pairing the strands of a plurality of double-stranded DNA molecules may be located in the adaptor(s) and/or, if present, in the hairpin sequence. The barcode may be a separated double-stranded DNA molecule that may be ligated to either one or both ends of the double-stranded DNA molecule. For example, the barcode may be ligated to one or to the two ends of the double-stranded DNA molecule before the adaptor and/or hairpin sequence is ligated to the double-stranded DNA molecule (and in this case, the adaptor and/or hairpin sequence may be ligated to the barcode). For example, the barcode may be ligated to one or to the two ends of the double-stranded DNA molecule after the adaptor is ligated to the double-stranded DNA molecule, and may be thus ligated to the adaptor.

The pairing step may also be performed by using both, hairpin sequences and barcodes.

The adaptors, hairpin sequences and/or barcode sequences may contain non-methylated cytosines and/or methylated cytosines. The adaptors, hairpin sequences and/or or barcode sequences may not contain non-methylated cytosines. For example, the adaptors, hairpin sequences and/or barcode sequences do not contain cytosines. For example, the adaptors hairpin sequences and/or barcode sequences contain methylated cytosines but they do not contain non-methylated cytosines. For example, the adaptors, hairpin sequences and/or barcode sequences contain methylated cytosines. For example, the adaptors, hairpin sequences and/or barcode sequences contain methylated cytosines and non-methylated cytosines.

If the adaptor contains non-methylated cytosines, these non-methylated cytosines will be equally treated with a reagent which allows transformation of non-methylated cytosines to a base that is detectably dissimilar to cytosine in terms of hybridization properties (preferably uracil) (in step (ii) of the method of the invention in any of its embodiments), and thus equally transformed to a base that is detectably dissimilar to cytosine in terms of hybridization properties (preferably uracil). Accordingly, the primers used in step (iii) (and, optionally in step (iv)), should contain sequences complementary to at least a portion of the double-stranded adaptors after such transformation.

The term "ends", as used herein, refers to the regions of sequence at (or proximal to) either end of a nucleic acid sequence.

The term "compatible", as used herein, means that both strands of one of the ends of the adapter molecule are capable of being ligated to one end or to both ends of the double stranded DNA molecule used as starting material. Compatible ends include blunt DNA ends and sticky ends with complimentary overhangs. Two compatible ends can be joined together preferably without any gap or mismatch and can be ligated to produce DNA sequences that often contain restriction endonuclease sites.

The term "blunt ends", as used herein, means that both strands of the double stranded DNA are of the same length and terminate in a base pair (i.e. there are no unpaired bases and the strands do not overlap or overhang the other).

The terms "sticky ends", "cohesive ends" and "overhanging ends" are used here interchangeably and refer to non-blunt ends created by various overhangs. An overhang is a stretch of unpaired nucleotides in the end of a DNA molecule. These unpaired nucleotides can be in either strand, creating either 3' or 5' overhangs. These overhangs are in most cases palindromic. The simplest case of an overhang is a single nucleotide. This is most often adenosine and is created as a 3' overhang by some DNA polymerases. The product is joined with a linear DNA molecule with 3' thymine overhangs. Since adenine and thymine form a base pair, this facilitates the joining of the two molecules by a ligase. In the first method of the invention, when the double stranded DNA molecules used in step (i) are end-repaired and d-A tailing prior to step (i), the first and second adapter molecules must have a 3'-thymine overhang. Longer overhangs are most often created by restriction endonucleases. For example, a restriction endonuclease may cut the two DNA strands four base pairs from each other, creating a four-base 5' overhang in one molecule and a complementary 5' overhang in the other. These ends are called cohesive ends since they are easily joined back together by a ligase. Since different restriction endonucleases usually create different overhangs, it is possible to cut a piece of DNA with two different enzymes and then join it with another DNA molecule with ends created by the same enzymes. Since the overhangs have to be complementary in order for the ligase to work, the two molecules can only join in one orientation.

The ligating step (i) is carried out under conditions adequate for the ligation of the adaptor and/or pairing molecules (hairpin and/or barcode sequences) to the DNA molecules to yield a plurality of adapter-modified DNA molecules.

The term "ligation", as used herein, refers to the formation of a covalent bond or linkage between the termini of two or more nucleic acids. The nature of the bond or linkage may vary widely and the ligation may be carried out enzymatically or chemically. As used herein, ligations are usually carried out enzymatically to form a phosphodiester linkage between a 5' carbon terminal nucleotide of one nucleic acid with a 3' carbon of another nucleic acid. Conditions adequate for the ligation are any conditions that allow obtaining a double-stranded DNA molecule linked to one or two adapters. Preferred conditions are the use of a DNA ligase although procedures for ligation without the use of DNA ligase are also known.

The pairing can be performed either before or after ligation, or simultaneously with the ligation of the adaptors and/or hairpin sequences. Preferably, the pairing is performed simultaneously with the ligation of the adaptors and/or hairpin sequences.

The result of the first step of the method of the invention (step (i)) is a plurality of DNA molecules.

In the context of the method of the invention, if the pairing step of step (i) of the method of the invention is achieved by the presence of a hairpin sequence (e.g. by the presence of a hairpin sequence on its own or by the presence of a hairpin sequence and one or more barcode sequences), the DNA molecules obtained in step (i) may be (see FIG. 1):

A) double stranded DNA molecules ligated to one adapter molecule (optionally including at least one barcode sequence) on one end and to a second molecule on the other end, wherein the second molecule is a hairpin sequence (and optionally including one or more barcode sequences) (these are the so-called paired adapter-modified DNA molecules);

B) double stranded DNA molecules ligated to two adapter molecules, in the absence of a hairpin sequence (at least one at each end);

C) double stranded DNA molecules ligated to two molecules (at least one at each end), which can be a hairpin sequences and/or barcode sequences; and D) double stranded DNA molecules without any molecule ligated to them (the original double stranded DNA molecules, namely non-modified double stranded DNA molecules).

In the context of the method of the invention, if the pairing step of step (i) of the method of the invention is achieved by the presence of (one or more) barcode sequences and in the absence of hairpin sequences, the DNA molecules obtained in step (i) may be:

A) double stranded DNA molecules ligated to one adapter molecule on each of the ends of the double stranded DNA molecule (including at least one barcode sequence) (these are the so-called paired adapter-modified DNA molecules);

B) double stranded DNA molecules ligated to at least one adapter molecule on only one of the ends of the double stranded DNA molecule;

C) if this is the case, double stranded DNA molecules ligated to at least one barcode sequence but in the absence of adaptor molecules on each of the ends of the double-stranded DNA molecule; and D) double stranded DNA molecules without any molecule ligated to them (the original double stranded DNA molecules, namely non-modified double stranded DNA molecules).

If the pairing step of step (i) of the method of the invention is achieved by the presence of (one or more) barcode sequences and in the absence of hairpin sequences, the paired adapter-modified DNA molecules obtained after step (i) should be ligated to one adapter molecule on each of the ends of the double stranded DNA molecule (including at least one barcode sequence for the pairing of both strands).

The population of double stranded DNA molecules may be treated, prior to step (i), with adapter molecules, under conditions adequate for the ligation of the adapter molecules to the DNA molecules thereby introducing cohesive ends in said DNA molecules. Adapter molecules having cohesive ends may be obtained by digestion of double-stranded DNA with a suitable restriction endonuclease enzyme or may be produced synthetically, such as by the annealing of single-stranded oligonucleotides.

After the ligation of adapters and/or pairing molecules (e.g. hairpin sequences and/or barcode sequences) in step (i), a capture step (or "recovering step", or "purification step")) may optionally be performed in order to recover from the reaction mixture those molecules which comprise the adapter(s) and/or hairpin sequences and/or barcode sequences according to options (A) above (depending on the pairing molecules, as described above), namely double stranded DNA molecules ligated to one adapter molecule (optionally including at least one barcode sequence) on one end and to a second molecule on the other end, wherein the second molecule is a hairpin sequence (and optionally including one or more barcode sequences) if the pairing is achieved by the presence of at least a hairpin molecule, and double stranded DNA molecules ligated to one adapter molecule on each of the ends of the double stranded DNA molecule (including at least one barcode sequence), if the pairing is achieved in the absence of hairpin sequences (only by at least one barcode sequence) ("recovering step"). Therefore, the first step (i) of the method of the invention may further involve recovering from the population of DNA molecules obtained in step (i) those molecules which are adapter-modified DNA molecules which comprise the adapter(s) and/or hairpin sequences and/or barcode sequences at one end or at two ends of the paired adapter-modified DNA molecule (molecules according to (A) above.

Said step allows separating the paired adapter-modified DNA molecules obtained in step (i) that comprise the adapter(s) and/or hairpin sequences and/or barcode sequences (according to (A) above) from the rest of DNA molecules generated (e.g. according to B)-D) above) (not according to (A) above). Said capture step may be performed for example by means of a probe or ligand that has affinity for the hairpin sequences and/or barcode sequences but not for the adapter molecule, or by means of a probe or ligand that has only affinity for the adapter molecule.

This provides the advantage that the sample used as a DNA template is preserved during the process and the original DNA template formed by the sense and antisense strands can be recovered, stored and submitted to multiple amplifications with different conditions and sequencings without sample exhaustion (steps iii and/or iv above). A schematic diagram is showed in FIG. 1.

Preferably, the recovering step (which may also be referred to as "capture step" or "purification step" or "separation step") is carried out using a polynucleotide comprising a sequence complementary to at least part of the sequence of the adapter(s) and/or hairpin sequences and/or barcode sequences and a purification tag.

The term "polynucleotide", as used herein, refers to a single-stranded DNA or RNA molecule comprising a number of nucleotide monomers covalently bonded. Preferably, the polynucleotide has 8 or more nucleotide monomers. In a preferred embodiment the polynucleotide is a single-stranded DNA molecule having at least 8, at least 9, at least 10, at least 11, at least 12, at least 13, at least 14, at least 15, at least 16, at least 18, at least 20, at least 25, at least 30, at least 35, at least 40, at least 50, at least 60, at least 70, at least 80, at least 90, at least 100 or more nucleotides long.

The term "purification tag", as used herein, refers to a moiety which enables separation of the polynucleotide and the target sequence. Preferably, the DNA backbone of the polynucleotide contains one or more nucleotides that are conjugated to an affinity purification tag. Preferably, the affinity purification tag may be a member of a binding pair. More preferably, the affinity purification tag is biotin and the double stranded DNA molecules are isolated by affinity purification with avidin or streptavidin. Said step, although not restricted to, can be performed by means of magnetic beads.

Prior to step (ii), the plurality of paired adaptor-modified DNA molecules generated in step (i) (as defined in (A) above, in both cases, depending on the pairing molecules) may be separated from DNA molecules generated in step (i) according to B)-D) as defined above) to generate a library of paired adaptor-modified DNA molecules according to (A) above. Accordingly, the method of the invention allows obtaining double stranded DNA libraries wherein the original sense and antisense strands of a DNA molecule are paired.

The term "DNA library", as used herein, refers to a collection of DNA fragments that have been ligated to adapter molecules in order to identify and isolate the DNA fragments of interest.

The expression "double stranded DNA library", in the present context may refer to a library that contains both strands of a molecule of DNA (i.e. the sense and antisense strands) physically joined by one of their ends (by e.g. a hairpin sequence) and forming part of the same molecule. The double stranded DNA library is not a circular library. The original strands of the DNA molecule may be physically joined by one of their ends by a loop thus forming a duplex between the sense and antisense strand (according to A) above). Each molecule of the double stranded DNA library may also be in linear conformation when complementarity between the sense and antisense strands of the DNA molecule is partially or completely lost. Alternatively, the expression "double stranded DNA library", in the context of the method of the present invention refers to a library wherein both strands of a molecule of DNA are not physically joined by one of their ends, but paired using e.g. at least one barcode sequence (according to A) above).

The ligation step of step (i) of the method of the invention may be referred to as "contacting step".

Step (ii)

DNA methylation typically occurs at CpG sites (cytosine-phosphate-guanine sites, where a cytosine is directly followed by a guanine in the DNA sequence). This methylation results in the conversion of the cytosine to 5-methylcytosine. The formation of Me (methyl)-CpG is catalyzed by the enzyme DNA methyltransferase. Human DNA has about 80-90% of CpG sites methylated, but there are certain areas, known as CpG islands, that are GC-rich (made up of about 65% CG residues), wherein none are methylated. These are associated with the promoters of 56% of mammalian genes, including all ubiquitously expressed genes. One to two percent of the human genome are CpG clusters, and there is an inverse relationship between CpG methylation and transcriptional activity.

The pattern of methylation is important in the study of some diseases. In normal tissue, methylation of a gene is mainly located to the coding region, which is CpG poor; whereas the promoter region of the gene is unmethylated, despite a high density of CpG islands in the region. However, in cancer there is a methylation imbalance where genome-wide hypomethylation is accompanied by localized hypermehylation and an increase in expression of DNA methyltransferase. The methylation state of some genes can be used as a biomarker for tumorigenesis.

In a second step (step (ii)), the population of paired adapter-modified DNA molecules generated after step (i) is treated with a reagent which allows transformation of non-methylated cytosines to a base that is detectably dissimilar to cytosine in terms of hybridization properties (preferably uracil), in order to analyse the methylation pattern of the sample. Preferably, the primers used in steps (iii) (and optionally (iv)) are specific for the adapter molecule after having been treated with said reagent. FIG. 1 shows a schematic diagram showing this embodiment of the method of the invention.

The expression "base that is detectably dissimilar to cytosine in terms of hybridization properties", as used herein, refers to a base that cannot hybridize with a guanine in the complementary strand. Preferably, the base detectably dissimilar to cytosine is thymine or uracil, more preferably is uracil.

The reagent used in this step must be a reagent capable of converting non-methylated cytosines to a base that is detectably dissimilar to cytosine in terms of hybridization properties but incapable of acting on methylated cytosines. Examples of such agents are, without limitation, bisulfite, metabisulfite and cytidine-deaminases such as activation-induced cytidine deaminase (AID). In a preferred embodiment the reagent is bisulfite. As used herein, bisulfite ion has its accustomed meaning of $HSO_3^-$. Typically, bisulfite is used as an aqueous solution of a bisulfite salt, for example sodium bisulfite, which has the formula $NaHSO_3$, or magnesium bisulfite, which has the formula $Mg(HSO_3)_2$. Suitable counter-ions for the bisulfite compound may be monovalent or divalent. Examples of monovalent cations include, without limitation, sodium, lithium, potassium, ammonium, and tetraalkylammonium. Suitable divalent cations include, without limitation, magnesium, manganese, and calcium. Treatment of DNA with bisulfite converts unmethylated cytosine bases to uracil, but leaves 5-methylcytosine bases unaffected. Said conversion is performed by standard procedures (Frommer et al. 1992, Proc Natl Acad Sci USA, 89:1827-31; Olek, 1996, Nucleic Acid Res. 24:5064-6; EP 1394172). Methods to obtain the sample include those used for reduced representation bisulfite sequencing (RRBS).

Preferably, the transformation of (non-methylated) cytosine to uracil in the paired DNA molecules is performed with bisulfite.

When the paired adapter-modified DNA molecules obtained in step (ii) are treated with a reagent capable of converting non-methylated cytosines to a base that is detectably dissimilar to cytosine in terms of hybridization properties (preferably uracil, as described above), complementarity between the sense and antisense strands of the original double-stranded DNA molecules is partially or completely lost. This facilitates the annealing of the primers used in the subsequent steps. This also facilitates the generation of a complementary strand in step (iii), particularly if one of the strands has non-methylated cytosines and no methylated cytosines.

A paired adapter-modified DNA molecule is considered to lose partially complementarity between the regions containing the sense and antisense strands of the original double stranded DNA molecules wherein the nucleotides of one of the regions containing the sense or antisense strand pair with less than the 100% of the other region, less than the 99%, less than the 95%, less than the 90%, less than the 80%, less than the 70%, less than the 60%, less than the 50%, less than the 40%, less than the 30%, less than the 20%, less than the 10%, less than the 5%, less than the 3%, less than the 1%, less than the 0.5%, less than the 0.1%. It is considered that complementarity has been completely lost when the nucleotides of one of the regions containing the sense or antisense strand pair with 0% of the other region.

In the particular case in which the original double-stranded DNA molecule is completely methylated, the complementarity between the sense and antisense strands of the original double-stranded DNA molecules is not lost after the treatment with a reagent capable of converting non-methylated cytosines to a base that is detectably dissimilar to cytosine in terms of hybridization properties (e.g. uracil). In the particular case in which one of the strands has (non-methylated) cytosines and no methylated cytosines, the complementarity is optimally lost.

Step (iii)

In a third step, DNA strands are synthesized using the paired and transformed adapter-modified DNA molecules obtained in step (ii) as template under conditions that allow the strand synthesis to take place and using as primer the sequence of which is complementary to at least a portion of the sequence of the first adapter molecule. Accordingly, step (iii) of the method of the invention provides complementary strands of the paired and transformed adaptor-modified DNA molecules using the nucleotides A, G, C and T, and primers the sequences of which are complementary to at least a portion of the double-stranded adaptors to provide partially transformed paired double-stranded molecules.

After the treatment with e.g. bisulfite, DNA strands are synthesized using the transformed and paired adapter-modified DNA molecule obtained in step (ii) as template and using a primer the sequence of which is complementary to at least a portion of the sequence of the adapter molecule or to at least a portion of the complementary sequence of the adapter molecule (preferably, the primers used in steps (iii) (and optionally (iv)) are specific for the adapter molecule, or its complementary sequence, after having been treated with the reagent used in step (ii), as described previously) and, optionally, the product obtained may be amplified. Uracil is recognized as a thymine by the Taq polymerase and, after the elongation (and optionally the amplification step), the product obtained contains a thymine in the position in which the DNA template has a non-methylated cytosine and contains a cytosine in the position in which the DNA template has a 5-methylcytosine.

The expression "synthesizing DNA strands" refers to the synthesis of a DNA molecule complementary to an adapter-modified DNA molecule used as template that is under conditions that allow the strand synthesis to take place.

The term "template" refers to a strand of DNA which sets the genetic sequence of new strands.

The expression "under conditions that allow the strand synthesis to take place refers to conditions in which the hydrogen bonds between complementary bases in the regions containing the sense and antisense strands of the double stranded DNA molecules used in step (i) are disrupted. Said conditions are conditions adequate for separation of the regions containing the sense and antisense strands of the original double stranded DNA molecules which include, without limitation, conditions that allow the adoption of a linearized form of the adapter-modified DNA molecules obtained after step (i) if the pairing was obtained by a hairpin molecule, or the use of isothermal techniques, such as strand displacement DNA polymerases.

The conditions adequate for separation of said regions are conditions in which denaturation of both regions is achieved, for example by heating the molecules to 94-98° C. for 20 seconds-2 minutes causing the disruption of the hydrogen bonds between complementary bases. The separation of said regions may also be achieved without heating the molecules, by the use of isothermal techniques, for example by using strand displacement DNA polymerases such as, without limitation, Phi29DNA polymerase or the large fragment of *Bacillus stearothermophilus* DNA polymerase.

In addition, when the paired adapter-modified DNA molecules obtained in step (i) are treated with a reagent capable of converting non-methylated cytosines to a base that is detectably dissimilar to cytosine in terms of hybridization properties (preferably uracil), complementarity between the sense and antisense strands of the original double-stranded DNA molecules is partially or completely lost. This may facilitate the synthesis of the complementary strands, particularly if one of the strands has non-methylated cytosine and no methylated cytosine.

The term "primer", as used herein, refers to a short strand of nucleic acid that is complementary to a sequence in another nucleic acid and serves as a starting point for DNA synthesis. Preferably the primer has at least 2, at least 3, at least 4, at least 5, at least 6, at least 7, at least 8, at least 9, at least 10, at least 11, at least 12, at least 13, at least 14, at least 15, at least 16, at least 18, at least 20, at least 25, at least 30 or more bases long.

The term "complementary" refers to the base pairing that allows the formation of a duplex between nucleotides or nucleic acids, such as, for instance, between the two strands of a double-stranded DNA molecule or between an oligonucleotide primer and a primer binding site on a single-stranded nucleic acid or between an oligonucleotide probe and its complementary sequence in a DNA molecule. Complementary nucleotides are, generally, A and T (or A and U), or C and G. Two single-stranded DNA molecules are said to be substantially complementary when the nucleotides of one strand, optimally aligned and compared and with appropriate nucleotide insertions or deletions, pair with about 60% of the other strand, at least 70%, at least 80%, at least 85%, usually at least about 90% to about 95%, and even about 98% to about 100%. The degree of identity between two nucleotide regions is determined using algorithms implemented in a computer and methods which are widely known by the persons skilled in the art. The identity between two nucleotide sequences is preferably determined using the BLASTN algorithm (BLAST Manual, Altschul, S. et al., NCBI NLM NIH Bethesda, Md. 20894, Altschul, S., et al., J., 1990, Mol. Biol. 215:403-410).

The primer may hybridize to the sequence of the adapter molecule (and preferably to the sequence derived from it after the treatment with the reagent in step (ii), preferably bisulfite) under low stringency conditions, preferably medium stringency conditions, most preferably high stringency conditions. The primers used in steps (iii) and, if this is the case, in step (iv) are specific for the adapter molecule after having been treated with a reagent which allows transformation of non-methylated cytosines to a base that is detectably dissimilar to cytosine in terms of hybridization properties (e.g. bisulfite), as described previously.

"Hybridization" refers to the process in which two single-stranded polynucleotides bind non-covalently to form a stable double-stranded polynucleotide. "Hybridization conditions" will typically include salt concentrations of approximately 1 M or less, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the Tm for the specific sequence at a defined ionic strength and pH. Exemplary stringent conditions include a salt concentration of at least 0.01 M to no more than 1 M sodium ion concentration (or other salt) at a pH of about 7.0 to about 8.3 and a temperature of at least 25° C.

Hence, the transformed paired adapter-modified DNA molecules (are converted to double-stranded DNA molecules (one or, as the case may be, two separated single-stranded molecules, depending on the type of pairing (physical or by barcode sequences)) by methods well known in the art (i.e. elongation/extension with DNA polymerase and dNTPs), to provide partially transformed (the original strand has been affected by the treatment with a reagent which allows transformation of non-methylated cytosines to a base that is detectably dissimilar to cytosine in terms of hybridization properties (preferably uracil), but not the newly generated one) paired double-stranded DNA molecules.

Figure 2:
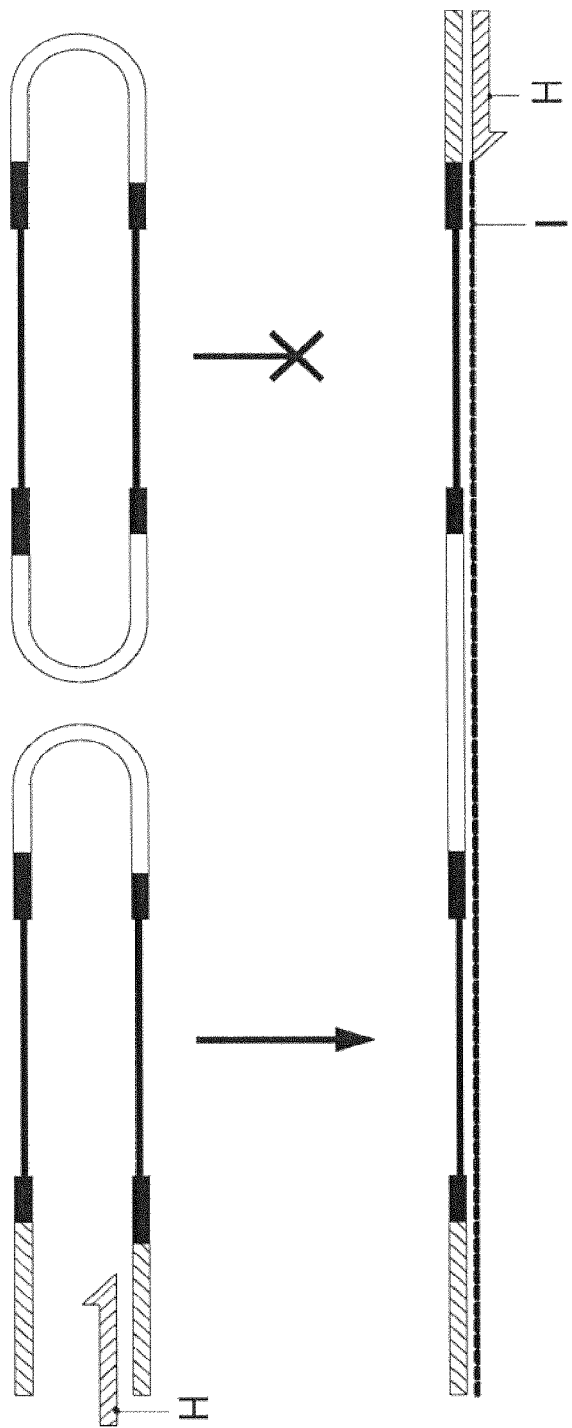
FIG. 2. Schematic diagram showing the elongation step of one embodiment of the method of the invention [step (iii)]. Only ligation products with one first adapter (DBE and EBD, as referred to in FIG. 1) will be extended with the primer (H) to obtain a synthetic strand (I).

The paired and transformed adapter-modified DNA molecules recovered in step (ii) may also include double stranded DNA molecules ligated to two hairpin molecules and/or to two barcode sequences (e.g. if a recovering or purification step did not take place). However, said molecules are not converted to double-stranded DNA molecules since there is no target sequence in the hairpin molecule/barcode sequences for the primer used in step (iii). FIG. 2 shows the elongation step of the method of the invention where only ligation products with one adapter ligated to one end of the double-stranded DNA molecule are elongated and amplified.

The constructs obtained after step (ii), or after step (iii) or after step (iv) form the double stranded DNA libraries of the invention and can be used for sequencing or in other conventional molecular biology techniques.

Step (iii) may also be referred to as "elongation step".

Step (iv) (Also Referred to as "Amplification Step")

Optionally, said constructs can be amplified to increase the amount of material for the following steps. In a preferred embodiment, the double stranded DNA molecules obtained in step (iii) are amplified using primers the sequences of which are complementary to at least a portion of the adapter region (the primers used in (iv) are specific for the adapter molecule after having been treated with the reagent of step (ii), as stated already above).

Accordingly, in an optional fourth step, the method of the invention comprises amplifying the partially transformed paired double stranded DNA molecules obtained in step (iii) to provide amplified paired double stranded DNA molecules.

The DNA amplification allows creating multiple copies of said molecules by in vitro synthesis of double stranded DNA molecules. Any method for DNA amplification may be used. Preferably, it is performed by polymerase chain reaction. In another embodiment it can be performed by real time-PCR using different probes (e.g. LightCycler, Taqman, Escorpio, Sunrise, Molecular Beacon or Eclipse). Different amplification conditions can be used on aliquots of the same sample to overcome any biases that may occur.

The double stranded DNA molecules obtained by the method of the invention may be recovered from the reaction mixture ("recovering step" or "purification step"). Therefore, preferably, the DNA molecules obtained in step (iii) or, as the case may be, in step (iv) are recovered from the reaction mixture. More preferably, said recovery is carried out using a first member of a binding pair, wherein the primer used in step (iii) or, as the case may be, in step (iv) is modified with a second member of said binding pair.

Optionally, the original plurality of double stranded DNA molecules may be recovered. The paired adapter-modified DNA molecules obtained in step (i) act as original template for elongation and amplification steps. Said original template is not destroyed in the processing and can be saved and reused or stored for subsequent processes. In order to achieve this goal, the original template may be tagged with modified adapters/hairpin sequences/barcode sequences. Thus, in a preferred embodiment, the paired adapter-modified DNA molecules obtained in step (i) are recovered from the reaction mixture obtained after step (iii) or, as the case may be, after step (iv). In a more preferred embodiment said recovery is carried out using a first member of a binding pair, wherein the adapters and/or hairpin sequences and/or barcode sequences are modified with a second member of said binding pair.

The term "reaction mixture", as used herein, refers to the mixture obtained after steps (iii) and/or (iv) have taken place. Said reaction mixture is formed by the combination of reagents, paired adapter-modified DNA molecules used as a template, unreactive paired adapter-modified DNA molecules, and reaction products including the molecules that form the double stranded DNA library.

The term "binding pair", as used herein, refers to a pair formed by a first member and a second member and includes any of the class of immune-type binding pairs, such as antigen/antibody (digoxigenin/anti-digoxigenin antibody) or hapten/anti-hapten systems; and also any of the class of nonimmune-type binding pairs which include systems wherein the two components share a natural affinity for each other but are not antibodies, such as biotin/avidin, biotin/streptavidin, folic acid/folate binding protein, complementary nucleic acid segments, protein A or G/immunoglobulins; and covalent binding pairs which form a covalent bond with each other, such as sulfhydryl reactive groups including maleimides and haloacetyl derivatives, and amine reactive groups such as isothiocyanates, succinimidyl esters and sulfonyl halides, etc.

The sequence of the primer used in step (iii) or in step (iv), or the sequence of the adapters and/or hairpin sequences and/or barcode sequences can be designed to incorporate bases labeled with the second member of a binding pair (e.g. digoxigenin, biotin, etc.). The incorporated labeled bases can be used to complex them with a first member of the binding pair, optionally bound to a support.

The primers used in steps (iii) and, if this is the case, in step (iv) are specific for the adapter molecule after having been treated with a reagent which allows transformation of non-methylated cytosines to a base that is detectably dissimilar to cytosine in terms of hybridization properties (e.g. bisulfite). The term "specific", as used herein, means that the primers are capable of hybridizing to the adapter molecule only when said molecule has been treated with a reagent that converts non-methylated cytosines to a base that is detectably dissimilar to cytosine in terms of hybridization properties (e.g. uracil). Preferably said primers are not capable of hybridizing to the adapter molecule before it is submitted to said conversion. If the adapter molecule contains non-methylated cytosines the primers used in step (iii) and/or (iv) have an adenine base instead of a guanine base in the positions that pair with the non-methylated cytosines of the original adapter molecule. The adapter molecule may contain methylated or non-methylated cytosines. Optionally, in order to avoid that a specific portion of the sequence of the adapter molecules, hairpin sequences and/or barcode sequences changes after the treatment with said reagent, the sequence of the first adapter molecule and preferably the combinatorial sequence within the adapter, if this is the case, sequence may contain modified cytosines which are resistant to treatment with the reagent which allows conversion of non-methylated cytosines to a base that is detectably dissimilar to cytosine in terms of hybridization properties.

The term "modified cytosines", as used herein, refers to cytosine bases that have been modified by the replacement or addition of one or more atoms or groups in order to obtain a modified cytosine that cannot be converted to a base that is detectably dissimilar to cytosine in terms of hybridization properties by the treatment with a reagent that converts non-methylated cytosines to a base detectably dissimilar to cytosine. Examples of modified cytosines suitable for the adapter sequence and preferably for the combinatorial sequence of the adapters, hairpin sequences and/or barcode sequences of the invention are, without limitation, methylcytosine and 5-hydroxymethylcytosine. Said modified cytosines are resistant to the treatment with the reagent because they remain unchanged after the treatment (e.g. methylcytosine) or because upon bisulfite treatment they are converted into a base that is complementary to guanine and is read as cytosine in polymerase-base amplification and sequencing (e.g. 5-hydroxymethylcytosine that is converted to cytosine-5-methylsulfonate).

Subsequently, the paired DNA molecules obtained in step (iii) and/or in step (iv) (and/or, optionally and less preferred, the paired DNA molecules obtained in step (ii)) are sequenced (see section "Sequencing step", below in the description).

The presence of methylated cytosine at a given position is determined if a cytosine appears in one of the strands of the paired double stranded DNA molecules obtained in step (iii) and/or in step (iv) and a guanine appears in the corresponding position in the other strand of the paired double stranded DNA molecules, or wherein the presence of an non-methylated cytosine at a given position is determined if a uracil or thymine appears in one of the strands of the paired double stranded DNA molecules obtained in step (iii) or in step (iv) and a guanine appears in the corresponding position in the other strand of the paired double stranded DNA molecules. This is further described in the section "The identification of methylated cytosines" below.

First Embodiment of the Method of the Invention

The method of the invention may be performed on a solid support. Specifically, the double-stranded adaptors, hairpin sequences and/or barcode sequences may be provided immobilized in a support. When a solid support is used high automation with the sequencing machines and higher levels of sample conservation (sample perpetuation) are expected.

The immobilization may be preferably carried out by binding the end of one of the strands of the double-stranded adaptor, hairpin sequences and/or barcode sequences to said support. Preferably, the end of one of the strands of the double-stranded adaptor, hairpin sequences and/or barcode sequences is bound to that support. Accordingly, when the double-stranded adaptor, hairpin sequences and/or barcode sequences are immobilized in a support, the sense of the ligation may be directed, so that specific adapters/hairpin sequences or barcode sequences are ligated to specific ends of the DNA molecules.

If the double-stranded adapter molecules, hairpin sequences and/or barcode sequences are immobilized in a support, the step for recovering the original DNA template as described above is not needed, since the paired adapter-modified DNA molecules obtained in step (i) remain attached to the support.

Additionally, if the adapter molecules are immobilized in a support, all the paired adapter-modified DNA molecules obtained in step (i) are double stranded DNA molecules ligated to an adapter molecule at one end and to hairpin sequences and, optionally, to barcode sequences at the other end, if the pairing occurs by the presence of hairpin molecules. If the pairing occurs in the absence of hairpin sequences, namely, only by barcode sequences, then the paired adapter-modified DNA molecules obtained in step (i) are double stranded DNA molecules ligated to an adapter molecule at both of its ends, additionally comprising at least one barcode sequence. Therefore, it is not needed to recover the molecules that comprise the adaptor sequence on one end and hairpin sequences and/or barcode sequences and/or adaptor sequences on the other end (molecules according to A), as described above) from the population of molecules obtained in step (i).

In addition, in this embodiment of the invention, wherein the double-stranded adaptors hairpin sequences and/or barcode sequences are provided immobilized to a support, the pairing of step (i) may be performed by allocating the double-stranded adaptors to pre-determined positions on the support.

The term "support", as used herein, refers to any material configured to chemically bond with a nucleic acid including but not limited to plastic, latex, glass, metal (i.e. for example a magnetized metal), nylon, nitrocellulose, quartz, silicon or ceramic. The support is preferably solid and may be roughly spherical (i.e. for example a bead) or may comprise a standard laboratory container such as a microwell plate or a surface.

The term "immobilized", as used herein, refers to the association or binding between the molecule (e.g. adapter, hairpin sequence, barcode sequence) and the support in a manner that provides a stable association under the conditions of elongation, amplification, excision, and other processes as described herein. Such binding can be covalent or non-covalent. Non-covalent binding includes electrostatic, hydrophilic and hydrophobic interactions. Covalent binding is the formation of covalent bonds that are characterized by sharing of pairs of electrons between atoms. Such covalent binding can be directly between the adapter and the support or can be formed by a cross linker or by inclusion of a specific reactive group on either the support or the adapter or both. Covalent attachment of an adapter can be achieved using a binding partner, such as avidin or streptavidin, immobilized to the support and the non-covalent binding of the biotinylated adapter to the avidin or streptavidin. Immobilization may also involve a combination of covalent and non-covalent interactions.

The adapters, hairpin sequences and/or barcode sequences may be synthesized first, with subsequent attachment to the support. Alternatively, the adapters, hairpin sequences and/or barcode sequences may be synthesized directly on the support. Preferably, said immobilization is carried out by covalently binding the end of one of the strands of the adapter, hairpin sequence and/or barcode sequence or a nucleotide of the hairpin loop to said support.

Preferably, the adapter is attached to the support but the hairpin sequences and/or barcode sequences are not attached to said support. In the context of this embodiment, each adapter molecule attached to the support is separated enough from the neighboring adapter molecules to avoid that one double stranded DNA molecule ligates to two of these adapters. According to step (i) of the method of the invention, in an embodiment the plurality of double stranded DNA molecules is contacted with the adapter molecules attached to the support and only one adapter can be ligated to each double stranded DNA molecule. After that, the adaptors and/or hairpin sequences and/or barcode sequences may be ligated to the free end of the double stranded DNA molecule.

Alternatively, the hairpin sequences and/or barcode sequences may be attached to the support but the adapter molecule is not attached to said support. In this context of this embodiment, each hairpin sequences and/or barcode sequences attached to the support is separated enough from the neighboring hairpin sequences and/or barcode sequences to avoid that one double stranded DNA molecule ligates to two of these molecules. For example, the initial plurality of double stranded DNA molecules may be contacted with the hairpin sequences and/or barcode sequences attached to the support and only one hairpin sequence and/or barcode sequence can be ligated to each double stranded DNA molecule. After that, the adapter molecule is ligated to the free end of the double stranded DNA molecule (if the hairpin was attached to the support and ligated to the other end of the double stranded DNA molecule). In the case the pairing is achieved by only barcode sequence(s) (in the absence of hairpin sequences) and the barcode sequence is attached to the support, first an adaptor should be ligated to the attached barcode sequence. Then, the double stranded DNA sequence should be ligated to the adaptor. Finally, the other adapter molecule is ligated to the free end of the double stranded DNA molecule.

Alternatively, the adapter molecule and the hairpin sequences and/or barcode sequences may be attached to the support. Additional measures have thus to be taken in order to avoid that a double stranded DNA molecule ligates to two identical molecules which are not two identical adaptors in the case the pairing is achieved only by the presence of barcode sequences (in the absence of hairpin sequences), in which case the double stranded DNA molecule is ligated to two adaptors, one on each end of the double stranded DNA molecule.

The advantages of performing the method of the invention on a solid support (e.g. by immobilizing the adaptors and/or hairpin sequences and/or barcode sequences in a solid support, as described above) may be the following:

The direction of the ligation can be controlled, so no unwanted ligations (e.g. molecules with two hairpin sequences, etc.) are formed. In addition, since the original plurality of double-stranded DNA molecules is fixed to the solid support, there is no loss of initial material.

In addition, reactions can be performed in a flow cell. After the reactions (e.g. ligation, transformation, generation of the complementary strands) have been performed, the original material can be stored and reused (since it is attached to the support). The flow cell can be integrated into a NGS (next generation sequencing) device (and specific reactions, such as bridge amplification or sequencing reactions can be performed on the flow cell itself), allowing automation and simplifying the process.

After ligation of the double-stranded adaptors and the pairing of the strands of the plurality of double-stranded DNA molecules, which are at the end of the process immobilized in a support, as described above, the (non-methylated) cytosines present in both strands of the paired adaptor-modified DNA molecules are transformed to a base detectably dissimilar to cytosine (preferably to uracil) in the paired adaptor-modified DNA molecules, as described above (step ii).

Subsequently, complementary strands of the paired and transformed adaptor-modified DNA molecules are provided, using the nucleotides A, C, G and T, and primers the sequences of which are complementary to at least a portion of the double-stranded adaptors (preferably, the primers are specific for the adapter molecule after having been treated with the reagent of step (ii), as stated already above), to provide partially transformed paired double-stranded molecules (step iii).

This step of providing complementary strands (step iii) in this embodiment of the invention may be performed with the paired and transformed adapter-modified DNA molecules attached to the support, and it is performed under conditions that allow the strand synthesis to take place.

Figure 3:
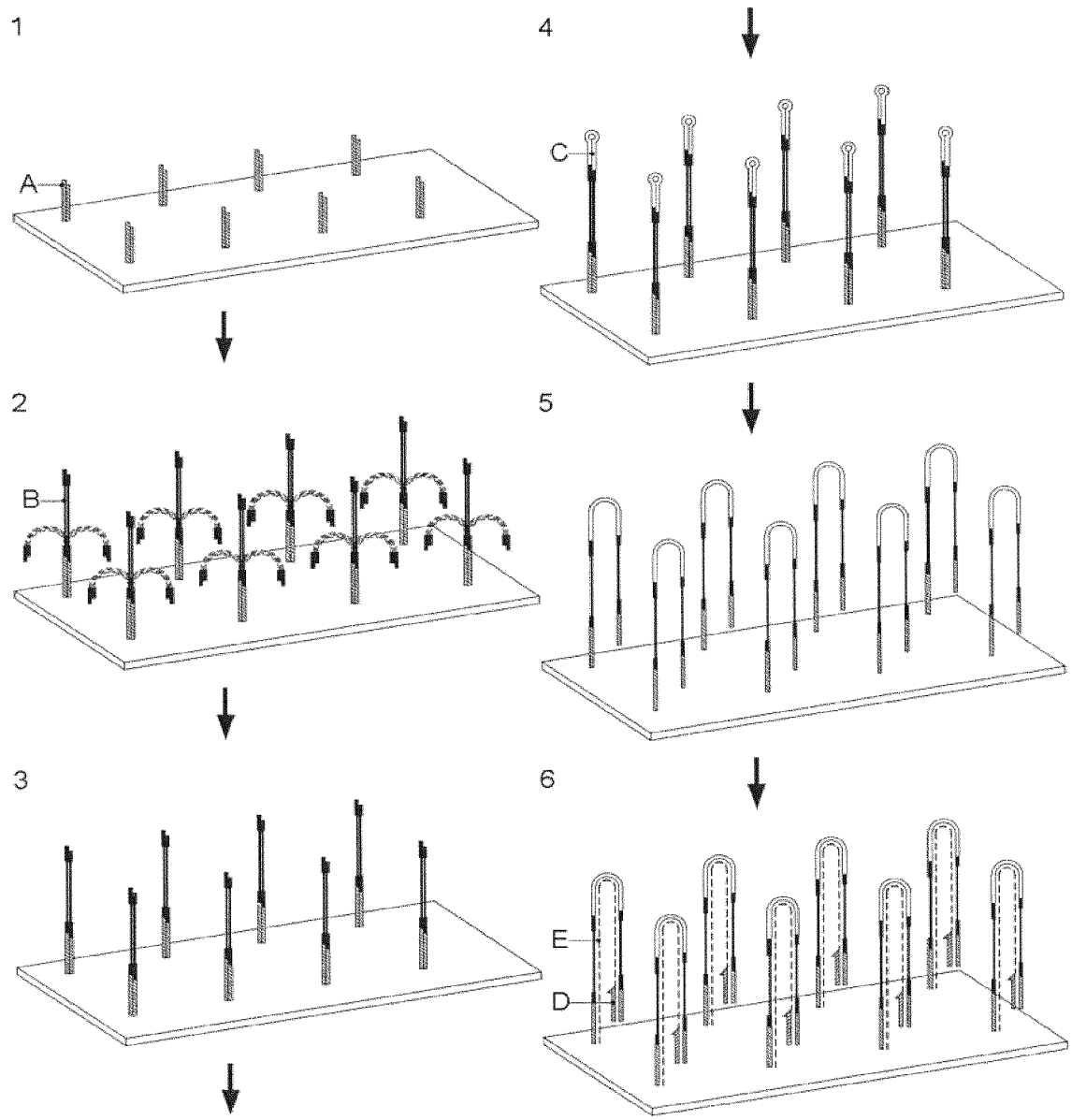
FIG. 3. Schematic diagram showing one embodiment of the method of the invention wherein the adapter molecules are provided immobilized in a support. 1. Distribution of the adapter (A) over the solid surface. 2. Ligation of genomic fragments (B). Only one A adapter can be ligated to each genomic fragment. 3. Ligated fragments. 4. The hairpin adapter (C) is ligated to the free end of the genomic fragment. 5. Bisulfite conversion and loss of complementarity. 6. Elongation step (step iii). The first polymerase elongation with the primer (D) is shown in order to obtain a synthetic strand (E).
Figure 4:
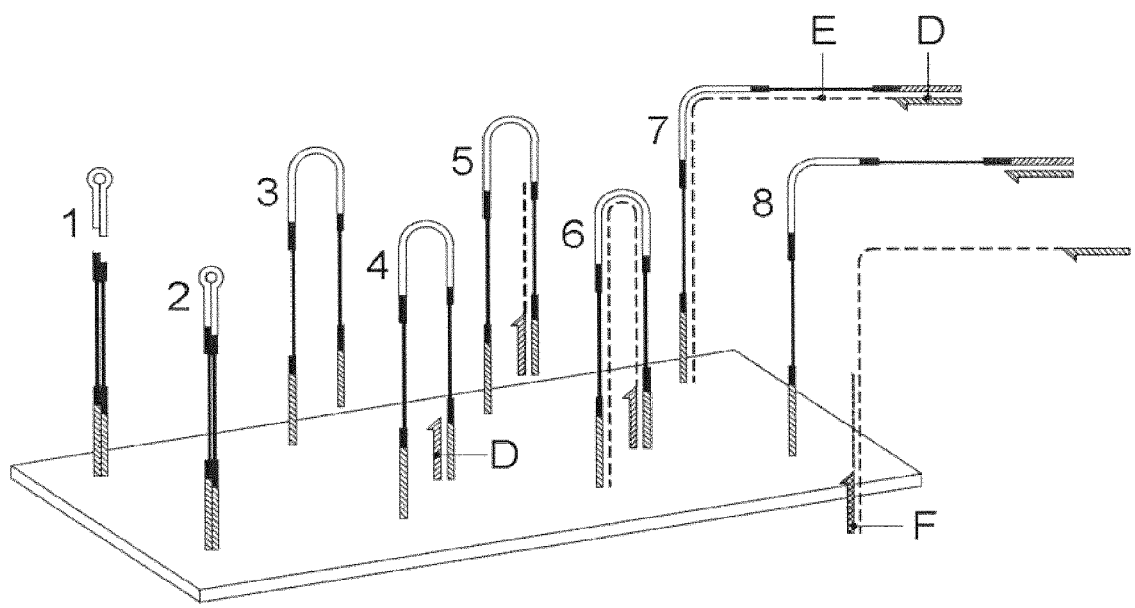
FIG. 4. Schematic diagram showing one embodiment of the method of the invention wherein the adapter molecules are provided immobilized in a support. 1. Genomic fragments (B) ligated to the first adapter molecules (A). 2. The hairpin adapter (C) is ligated to the free end of the genomic fragment. 3. Bisulfite conversion and loss of complementarity. 4. The primer (D) hybridizes to a portion of the sequence of the adapter molecule. 5, 6, 7. Elongation step (step iii). The first polymerase extension with the primer (D) is shown in order to obtain a synthetic strand (E). 8. The template remains attached to the solid surface and the extension product is released to the supernatant. The released molecules may be amplified with a primer (F) (step iv). The references of the letters A, B and C are the same as in FIG. 3.

Preferably, the primer used in the present embodiment (step iii) is not attached to the support. A schematic diagram showing this embodiment wherein the population of adapter molecules is provided immobilized in a support is depicted in FIGS. 3 and 4. The template strand remains attached to the support and the elongation product is released to the supernatant. Therefore, in this embodiment, a double stranded DNA library is released to the supernatant. Optionally, step (iv) (optionally amplifying the partially transformed paired double-stranded molecules) can be performed over the molecules that are on the supernatant, before or after being recovered from the reaction mixture. Such adapters or the adapter-modified DNA molecules attached to the support can be released from the support at various stages of the method.

Optionally, the primer used in step (iii) may also be attached to the support. In this case, the template and the elongation product remain attached to the support. Therefore, in this case, the double stranded DNA library is attached to the support. The adapters, the primers and/or the adapter-modified DNA molecules attached to the support can be released from the support at various stages of the present embodiment of the method.

Optionally, step (iv) can be performed over the molecules that are attached to the support or over the molecules that are on the supernatant after having been released from the support.

The primers used in the optional step of amplification (iv) are preferably not attached to the support. However, one or both primers used in step (iv) may be attached to the support. When both primers used in step (iv) are attached to the support, a bridge amplification (which can be isothermal) may take place. This bridge amplification may give rise to polonies, i.e. clonally clustered amplicons, amenable for sequencing protocols, particularly for NGS (next generation sequencing).

This embodiment allows recovering the template bound to the support, thus increasing sample perpetuation. Said support attached to the template may be used for storage of the sample. The template can be used in different amplifications with different conditions to overcome any biases that may occur. Said recovery of the original template does not need a recapture step based on binding pairs. Therefore, this embodiment is especially suitable for samples with limited amount of material. Although a recapture step is not needed, the DNA molecules obtained in step (i) or (ii) may be released from the support and recovered from the reaction mixture obtained after step (iii) or, as the case may be, after step (iv). Preferably, said recovery from the reaction mixture is carried out using a first member of a binding pair, wherein the adapter and/or hairpin sequences and/or barcode sequences are modified with a second member of said binding pair.

The DNA molecules obtained in step (i) may also be used for sequencing.

Preferably, the double stranded DNA molecules used in step (i) are fragments of genomic DNA. Optionally, the double stranded DNA molecules used in step (i) are end-repaired prior to said step (i), preferably further comprising a step of dA-tailing the DNA molecules after the end-repairing step. The adapter molecules and/or hairpin molecules and/or barcode molecules may be provided as libraries of molecules, wherein each member in the library is distinguishable from the others by a combinatorial sequence within the molecule sequence. After step (i), the population of adapter-modified DNA molecules is treated with a reagent which allows conversion of non-methylated cytosines to a base that is detectably dissimilar to cytosine in terms of hybridization properties and wherein the primers used in steps (iii) and, optionally step (vi) of the method of the invention are specific for the adapter molecule after having been treated with said reagent (step (ii) of the method of the invention). The combinatorial sequence within the adapter sequence and/or hairpin sequence and/or barcode sequence may contain modified cytosines which are resistant to treatment with the reagent which allows conversion of non-methylated cytosines to a base that is detectably dissimilar to cytosine in terms of hybridization properties. They may not contain non-methylated cytosines. Optionally, the DNA molecules obtained in step (iii) or, as the case may be, in step (iv) of the second method of the invention are recovered from the reaction mixture, preferably using a first member of a binding pair, wherein the primer used in step (iii) or, as the case may be, in step (iv) of the method of the invention is modified with a second member of said binding pair. The population of double stranded DNA molecules may be treated, prior to step (i) with adapter molecules, under conditions adequate for the ligation of the adapter molecules to the DNA molecules thereby introducing cohesive ends in said DNA molecules.

Second Embodiment of the Method of the Invention

In the second embodiment of the method of the invention, the double-stranded DNA adapters which are ligated to at least one end of the strands of a plurality of double-stranded DNA molecules (step (i) of the method of the invention), have a "Y" form, and are referred to as "Y adapters".

The terms "Y-adapter" and "Y-adaptor" are used interchangeably and, in the context of the present embodiment, refer to an adapter formed by two DNA strands wherein the 3' region of the first DNA strand and the 5' region of the second DNA strand form a double stranded region by sequence complementarity, wherein the ends of said double stranded region formed by the 3' region of the first DNA strand and the 5' region of the second DNA strand of the Y-adapter are compatible with the ends of the double stranded DNA molecules. The expression "3' region", as used herein, refers to a region of a nucleotide strand that includes the 3' end of said strand.

The term "3' end", as used herein, designates the end of a nucleotide strand that has the hydroxyl group of the third carbon in the sugar-ring of the deoxyribose at its terminus.

The expression "5' region", as used herein, refers to a region of a nucleotide strand that includes the 5' end of said strand.

The term "5' end", as used herein, designates the end of a nucleotide strand that has the fifth carbon in the sugar-ring of the deoxyribose at its terminus.

The expression "sequence complementarity", as used herein, refers to a property shared between two nucleic acid sequences, such that when they are aligned antiparallel to each other, the nucleotide bases at each position will be complementary.

The plurality of paired adaptor-modified DNA molecules obtained according to step (i) of the method of the invention according to this second embodiment are obtained by:
  (a) Ligating a DNA Y-adapter to each end of the strands of a plurality of double-stranded DNA molecules, said adapter comprising a first DNA strand and a second DNA strand, wherein the 3' region of the first DNA strand and the 5' region of the second DNA strand form a double stranded region by sequence complementarity, wherein the ends of said double stranded region formed by the 3' region of the first DNA strand and the 5' region of the second DNA strand of the Y-adapter are compatible with the ends of the double stranded DNA molecules;
  (b) Synthesizing, for each of the strands of the DNA molecules obtained in step (a) a complementary strand by polymerase elongation from the 3' end of the second DNA strand in the Y-adapter molecule using each of the strands of the DNA molecules obtained in step (a) as template, thereby pairing each of the strands of the DNA molecules obtained in step (a) with its synthetic complementary strand to provide a plurality of paired adaptor-modified DNA molecules.

Preferably, the 3' region of the second DNA strand of the Y-adapter forms a hairpin loop by hybridization between a first and a second segment within said 3' region, the first segment being located at the 3' end of the 3' region and the second segment being located in the vicinity of the 5' region of the second DNA strand.

Optionally, the 3' region of the second DNA strand of the Y-adapter does not form a hairpin loop by hybridization between a first and a second segment within said 3' region.

The pairing step of step (i) of the method of the invention according to the present embodiment may take place physically (by the presence of a hairpin sequence in the Y adaptor, which allows the original DNA strand its synthetic complementary strand be physically paired) or by the presence of barcode sequences in the Y adaptors (either in the double-stranded region and/or in any of the single stranded regions, or in all three regions), and in the absence of hairpin sequence, which allows the original DNA strand its synthetic complementary strand be not physically bound but paired by the presence of at least one barcode sequence, or by both (hairpin sequence and one or more barcode sequences).

Accordingly, in one aspect, the 3' region of the second DNA strand of the Y-adapter may form a hairpin loop by hybridization between a first and a second segment within said 3' region, the first segment being located at the 3' end of the 3' region and the second segment being located in the vicinity of the 5' region of the second DNA strand. In this aspect, each of the strands of the DNA molecules obtained in step (a) is physically paired (by means of at least one hairpin molecule) with its synthetic complementary strand to provide paired adaptor-modified DNA molecules. Of course, barcode sequences may also be present in the Y adaptors.

The term "hairpin loop", as used herein, refers to a region of DNA formed by unpaired bases that is created when a DNA strand folds and forms base pairs with another section or segment of the same strand.

The term "hybridization", as used herein, refers to the process in which two single-stranded polynucleotides or two regions of the same strand bind non-covalently to form a stable double-stranded polynucleotide.

Accordingly, the present aspect allows obtaining double stranded DNA libraries wherein the original sense and antisense strands of a DNA molecule are physically bound to each other. Each original strand of a DNA molecule is physically bound to a complementary strand obtained by synthetic extension. A schematic diagram of this embodiment is showed in FIG. 5 and FIG. 6.

The term "DNA library", as used herein, refers to a collection of DNA fragments that have been ligated to adapter molecules in order to identify and isolate the DNA fragments of interest.

The expression "double stranded DNA library", in the context of the present aspect, refers to a library that contains one of the original strands of a DNA molecule physically joined by one of their ends to a complementary strand obtained by synthetic extension. The double stranded DNA library of the third method of the invention is not a circular library. The original DNA strand of a DNA molecule and its synthetic complementary strand are physically joined by one of their ends by a loop thus forming a duplex between them (see FIG. 12). In the present aspect of the second embodiment of the method of the invention, each original DNA strand of a DNA molecule and its synthetic complementary strand are paired by the hairpin loop, thus physically paired. Each molecule of the double stranded DNA library may also be in linear conformation when complementarity between both strands is partially or completely lost.

In another aspect of the second embodiment of the method of the invention, the pairing is performed by the presence of at least one barcode sequence in the Y adaptor (either in any of its single stranded region, and/or in the double stranded region, or in both). According to this aspect, the 3' region of the second DNA strand of the Y-adapter does not form a hairpin loop by hybridization between a first and a second segment within said 3' region. In this case, each original DNA strand of a DNA molecule and its synthetic complementary strand are paired by the presence of barcode sequences in the double-stranded region of the Y adapter, or in the single-stranded region of the Y adapter, or by the presence of barcode sequences anywhere else on the original DNA strand.

Of course, the pairing of the original DNA strand of a DNA molecule and its synthetic complementary strand may be performed both physically (by the presence of a hairpin loop in the Y adapter, as described above) and by the presence of one or more barcode sequences.

The Y adapter may contain one or more barcode sequences in its double-stranded DNA region. This will provide at least for the pairing between each original DNA strand of the original double-stranded DNA molecule.

In this case, the original sense and antisense strands of a DNA molecule are identified by combinatorial labeling ("barcode sequence" or "combinatorial barcodes"), particularly each of the sense and antisense strands will be linked to two combinatorial sequences. Since both combinatorial sequences are the same for the sense and antisense strands, both strands may be followed during the process. After the whole process, those complementary strands that were originally together will share the same two combinatorial sequences. This allows keeping track of both strands of each double stranded DNA fragment originally used in step (i) of the method of the invention. FIG. 13 shows an embodiment of the method of the invention wherein combinatorial labeling is used Alternatively or in addition, the Y adapter may contain one or more barcode sequences in the 5' region of the first DNA strand and/or in the 3' region of the second DNA strand of the Y adapter formed by two DNA strands (and/or in the double stranded region). The barcode sequences may thus be located in the single-stranded region of the Y-adapter molecule and/or in the double stranded region of the Y-adapter. In this case, each original DNA strand and its synthetic complementary strand would then be paired.

Preferably, the DNA Y adaptor has a first barcode sequence in the double stranded region and/or a second barcode sequence in the 3' region of the second DNA strand of the Y-adapter. Optionally, the DNA Y adaptor has a first barcode sequence in the double stranded region and/or a second barcode sequence in the 5' region of the first DNA strand of the Y-adapter. Optionally, the DNA Y adaptor has a first barcode sequence in the double stranded region and/or a second barcode sequence in the 3' region of the second DNA strand of the Y-adapter and/or a third barcode sequence in the 5' region of the first DNA strand of the Y-adapter.

Preferably, the DNA Y-adaptor has a restriction site in the 5' region of the first DNA strand of the Y adapter.

When each original DNA strand of a double-stranded DNA molecule and each original DNA strand and its synthetic complementary strand are paired, this is referred to as "double pairing" (namely, a strand paired with its original complementary strand and with its synthetic complementary strand, at the same time). The double pairing provides intrinsic validation of each nucleotide reading by allowing the comparison of four different molecular sources of information (the top and bottom strands of a given dsDNA molecule and their respective synthetic complementary strands), which further increases the reliability of the results. In addition, this allows to assess both top and bottom strands of the original double-stranded DNA molecule and, consequently, to analyze the hemimethylation at the genome scale. Preferably, the plurality of paired adaptor-modified DNA molecules obtained after step (i) according to this embodiment are double-paired, as described above.

The double stranded DNA molecules used in step (a) are preferably fragments of genomic DNA. Preferably, the fragments of genomic DNA used in step (a) are paired to provide a plurality of paired genomic DNA fragments. This pairing is, as described above, preferably performed by the use of barcode sequences.

Preferably, the double stranded DNA molecules used in step (a) are end-repaired prior to said step (a), preferably further comprising a step of dA-tailing the DNA molecules after the end-repairing step.

The ligating step (a) is carried out under conditions adequate for the ligation of the Y-adapter to both ends of the double stranded DNA molecules.

The result of said step (a) is a plurality of Y-adapter-containing DNA molecules. Said molecules are paired (by hairpin sequences and/or by barcode sequences) double stranded DNA molecules that have one Y-adapter ligated to each end of the molecule.

Preferably, in the present embodiment, the Y-adapter-containing DNA molecules obtained in step (a) are treated prior to step (b) under conditions adequate for separation of the strands of the Y-adapter-containing DNA molecules.

The conditions adequate for separation of the strands of the Y-adapter-containing DNA molecules may be, without limitation, conditions in which denaturation of both strands is achieved, for example by heating the molecules to 94-98° C. for 20 seconds-2 minutes causing the disruption of the hydrogen bonds between complementary bases and yielding single-stranded DNA molecules. The separation of the strands may also be achieved without heating the molecules by the use of isothermal techniques, for example by using strand displacement DNA polymerases such as, without limitation, Phi29DNA polymerase or the large fragment of *Bacillus stearothermophilus* DNA polymerase.

After the ligation of adapters in step (a), each of the strands of the DNA molecules obtained in step (a) are converted into paired double-stranded DNA molecules by polymerase elongation from the 3' end of the second DNA strand in the Y-adapter molecule using each of the strands of the DNA molecules obtained in step (a) as template (step (b) above).

The expression "converting each of the strands into a paired double-stranded DNA molecule", in the context of the present embodiment, refers to the synthesis of a DNA strand complementary to each of the strands, wherein both strands are paired. The pairing may be achieved physically (namely when the 3' region of the second DNA strand of the Y-adapter forms a hairpin loop by hybridization between a first and a second segment within said 3' region, the first segment being located at the 3' end of the 3' region and the second segment being located in the vicinity of the 5' region of the second DNA strand), resulting in a double-stranded DNA conformation wherein a single DNA strand is folded over itself.

Optionally, when the 3' region of the second DNA strand of the Y-adapter does not form a hairpin loop by hybridization between a first and a second segment within said 3' region, the pairing may be achieved by introducing barcode sequences in at least one strand of the Y-adapter, either in the double-stranded region or in the single-stranded region, preferably in the single-stranded region.

As described above, the pairing may be achieved by both, physical ligation of the original DNA strand and its synthetic complementary strand and by the presence of one or more barcode sequences.

The expression "polymerase elongation", as used herein, refers to the synthesis of a complementary strand by a DNA polymerase that adds free nucleotides to the 3' end of the second DNA strand in the Y-adapter molecule. Said Y-adapter molecule may act as a primer for the elongation step. During this step the temperature is chosen depending on the optimal temperature for the specific DNA polymerase used.

Preferably, step (b) is performed using the nucleotides A, G, C and T. Optionally, methylated cytosines may be used for the elongation step, but the use of non-methylated cytosine instead resolves critical problems:

1—Control for bisulfite transformation. Bisulfite transformation efficiency is variable, this means that not all cytosines are successfully transformed (preferably into uracil (U)). Moreover, assessing this efficiency in each experiment, and even in each molecule in a given experiment, is important.

Using methylated cytosine (C) for the new strand will not allow to assess (or control) the degree of C>U transformation, since every C will be methylated and hence be read as a C. In contrast, when non-methylated C are used the bisulfite transformation efficiency of each individual molecule can be determined.

2—Facilitation of amplification by decreasing the complementarity of the two strands paired by the hairpin.

After step (i) according to the present embodiment, two double-stranded DNA molecules are obtained from each Y-adapter-containing DNA molecule, and each of said double-stranded DNA molecules is formed by an original DNA strand of a DNA molecule and its synthetic complementary strand that are paired (they may be physically joined by one of their ends by a hairpin molecule, or they may contain a barcode sequence, or both, as described above).

The pairing between both strands of the original double-stranded DNA molecules allows keeping track of both strands of each double stranded DNA fragment originally used.

Therefore, each Y-adapter may include unique and combinatorial barcodes that allow sample identification and multiplexing as well as quantitative analysis. In a preferred embodiment the Y-adapter is provided as a library of adapters wherein each member of the library is distinguishable from the others by a combinatorial sequence located within the double stranded region formed by the 3' region of the first DNA strand and the 5' region of the second DNA strand of the adapter. The present invention thus provides a Y hairpin adapter comprising at least one barcode sequence, inter alia for use in the method of the present invention.

When a library of Y-adapters having a combinatorial sequence is used in step (i) of the method of the invention each Y-adapter containing DNA molecule obtained after step (i) will have two different combinatorial sequences, each of them located at one of the Y-adapters ligated to each end of the DNA molecule. The two identifiers are associated with an individual molecule in the starting sample, thus giving the ability to differentiate between constructs. Said identifiers allow identification of a specific construct comprising said identifiers and its descendants since after step (b) of the present embodiment the original sense and antisense strand of a double-stranded DNA molecule will remain in different molecules, but each of these molecules will contain both combinatorial sequences. Any amplification products of said initial individual molecules bearing said identifiers are assumed to be identical by descent. The combinatorial barcodes also allow quantifying the percentage of individual sequences within a sample and are useful for monitoring biases and error control during the amplification steps.

Optionally, the Y-adapter incorporates bases labeled with the second member of a binding pair that allows the recovery of the original DNA template after the elongation or amplification steps. This provides the advantage that the sample used as a DNA template may be identified, preserved during the process and recovered, stored and submitted to multiple amplifications with different conditions and sequencings without sample exhaustion.

The constructs obtained after step (i) according to the present embodiment form a double stranded DNA library, which can be used for sequencing or in other conventional molecular biology techniques.

Optionally, the Y-adaptors may contain "sites for cutting", as described above. The "sites for cutting" add a way to adapt the final elements of the library to the needs of the different sequencing platforms. Although this adaptation can be achieved through the specific design of the Y-adaptors (by introducing sequences that are compatible with the platform reagents, such as sequencing primers), the cutting sites allow modularity, to add barcodes or adapters for multiplexing (mixing sample from different origins) or for the needs of any of the platforms for massive sequencing (or also to eliminate possibly unnecessary nucleotides). The "sites for cutting" are specific sequences that allow the presence of a known target in the edges of the plurality of paired adaptor-modified DNA molecules (library of paired adaptor-modified DNA molecules obtained in step (i), or a library of paired and transformed adaptor-modified DNA molecules as obtained in step (iii) (and optionally in step (iv)). The "sites for cutting" may be ligated to the plurality of double-stranded DNA molecules before or after the step of ligating the Y-adapters. As stated above, the "sites for cutting" may be already included in the Y-adapters. This way, all fragments can be cut and adapters can be ligated properly (this way sequences of the adaptors that are no longer required may be removed to increase sequencing efficiency).

Subsequently, step (ii) of the method of the invention is performed, namely the (non-methylated) cytosines present in the plurality of paired adaptor-modified DNA molecules obtained in step (i) of the present embodiment of the method of the present invention are transformed (preferably to uracil) in the plurality of paired adaptor-modified DNA molecules, as previously described.

Figure 5:
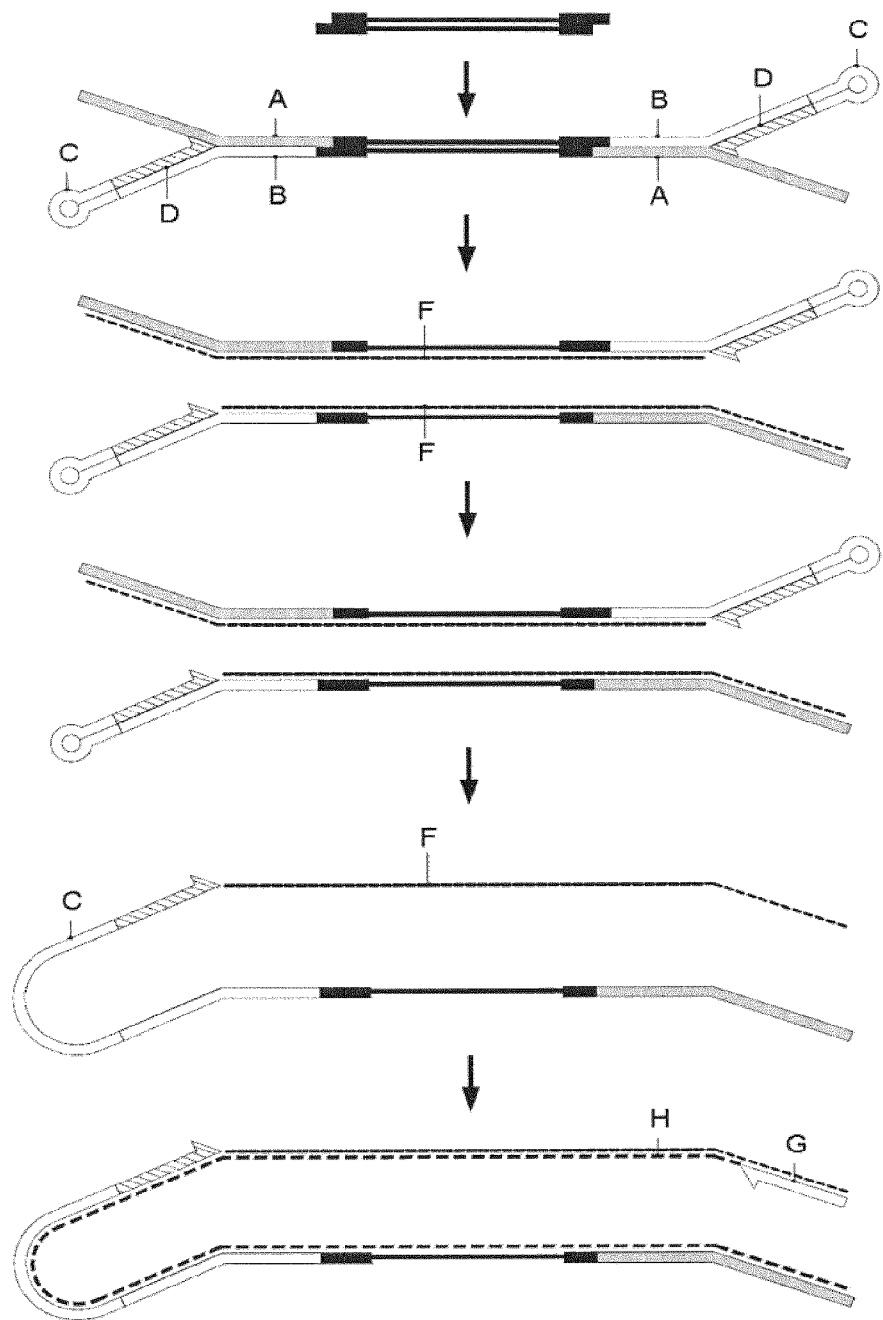
FIG. 5. Schematic diagram showing an embodiment of the method of the invention. Ligation step [step (i)]. Genomic fragments (black line) from the sample preparation step are ligated to two Y-adapters, each formed by a first DNA strand (A) and a second DNA strand (B), the second DNA strand being formed by a hairpin loop (C) and a first segment being located at the 3' end of the 3' region (D). Extension step. The synthetic sequence (dashed line, F) is generated using the hairpin as a primer for the polymerase. Bisulfite (step ii). The molecules obtained after the elongation step are bisulfite treated and the complementarity of the strands is lost. Complementary strand generation step (elongation step) [step (iii)]. Primer (G) is added for the first round of amplification (dotted line; H).
Figure 6:
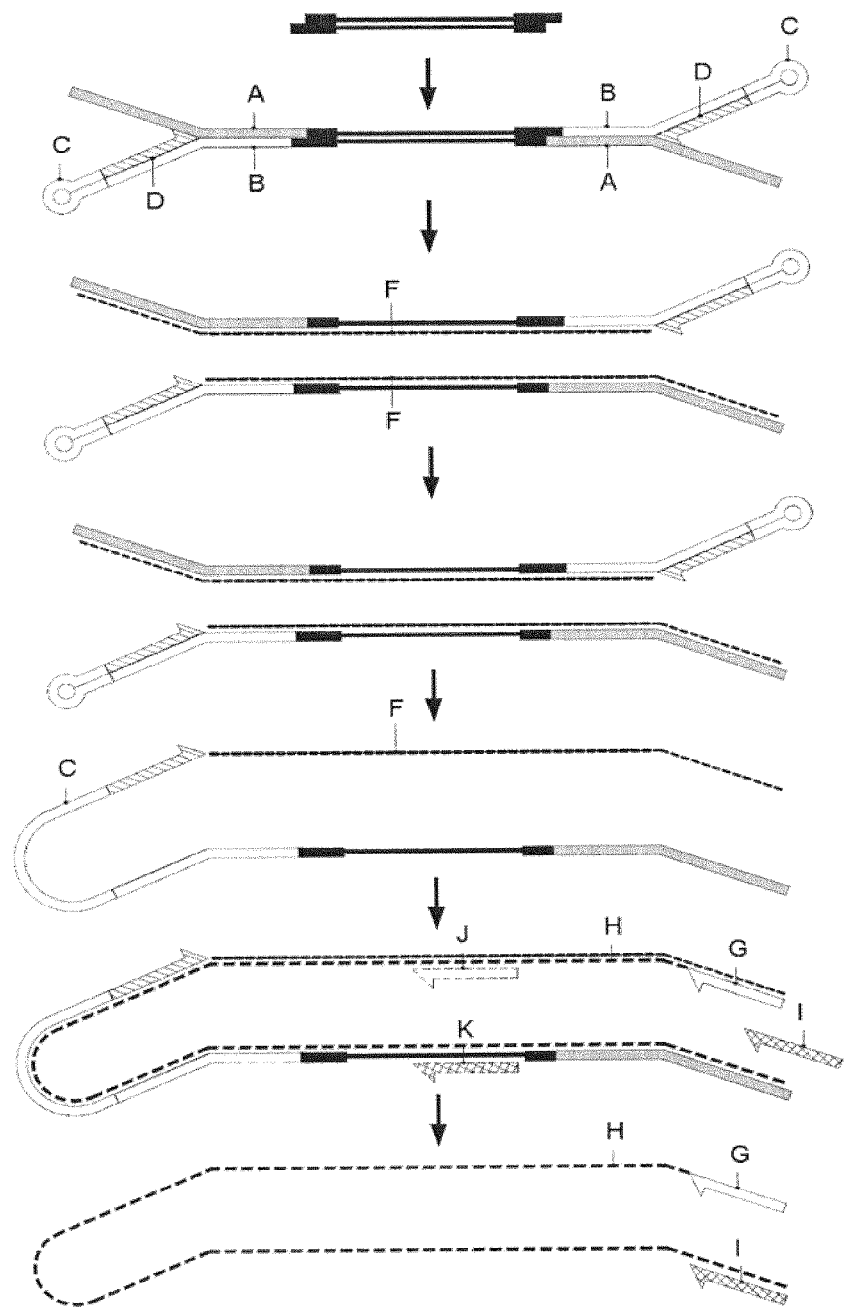
FIG. 6. Schematic diagram showing a further embodiment of the method of the invention. Ligation step [step (i)] and elongation step [step (iii)] are as described above. The first round of amplification step [step (iv)] is showed wherein a primer complementary to a portion of the complementary sequence of the first DNA strand of the adapter molecule (G) or a primer complementary to a specific sequence complementary to the sequence of the genomic fragment used for generating the library of the invention (J) is used. A pair of primers (G, I) or (J, K) may be used for the second and subsequent rounds of amplification.

Accordingly, the plurality of paired adapter-containing DNA molecules are treated with a reagent which allows conversion of non-methylated cytosines to a base that is detectably dissimilar to cytosine in terms of hybridization properties (preferably uracil) and wherein the primers used in step (iii) (and optionally step (iv)) are complementary to at least a portion of the sequence resulting from the treatment with said reagent of the double stranded DNA molecules obtained in step (ii). This treatment renders an adapter-containing DNA molecule wherein complementarity between the original and the synthetic strand is partially or completely lost, thus facilitating the annealing of the primer used in the subsequent step. FIGS. 5 and 6 show a schematic diagram showing this.

In a preferred embodiment the reagent is bisulfite which converts all non-methylated cytosines to uracils, which will be read as thymines in the molecules amplified in step (iii).

When the paired adapter-modified DNA molecules obtained in step (i) are treated with a reagent capable of converting non-methylated cytosines to a base that is detectably dissimilar to cytosine in terms of hybridization properties, complementarity between the sense and antisense strands of the original double-stranded DNA molecules is partially or completely lost. This may facilitate the synthesis of the complementary strands The Y-adapter-containing DNA molecules obtained in step (ii) of the method of the invention may be further treated prior to step (iii) under conditions adequate for separation of the strands of the Y-adapter-containing DNA molecules.

The conditions adequate for separation of the strands of the Y-adapter-containing DNA molecules may be, without limitation, conditions in which denaturation of both strands is achieved, for example by heating the molecules to 94-98° C. for 20 seconds-2 minutes causing the disruption of the hydrogen bonds between complementary bases and yielding single-stranded DNA molecules. The separation of the strands may also be achieved without heating the molecules by the use of isothermal techniques, for example by using strand displacement DNA polymerases such as, without limitation, Phi29DNA polymerase or the large fragment of *Bacillus stearothermophilus* DNA polymerase. Subsequently, step (iii) of the method of the invention is performed, namely providing complementary strands of the paired and transformed plurality of adaptor-modified DNA molecules.

Optionally, said constructs can be amplified (step (iv)) to increase the amount of material for the following steps. Preferably, the double stranded DNA molecules obtained in step (iii) are amplified using at least a primer the sequence of which is complementary to at least a portion of the double stranded DNA molecules obtained in step (iii).

Preferably, the double stranded DNA molecules obtained in step (iii) may be amplified in a first amplification step using a primer the sequence of which is complementary to at least a portion of the complementary sequence of the 5' region of the first DNA strand of the adapter molecule. The primers used in step (iii) (and optionally step (iv)) are preferably complementary to at least a portion of the sequence resulting from the treatment with the reagent of the double stranded DNA molecules obtained in step (ii). This embodiment is showed in FIGS. 5 and 6 and allows obtaining amplification for the whole sequence of the population of double stranded DNA molecules used for generating a double stranded DNA library.

Alternatively, the double stranded DNA molecules obtained in step (iii) may be amplified in a first amplification step using a primer the sequence of which is complementary to at least a portion of the complementary sequence of the population of double stranded DNA molecules used for generating the double stranded DNA library. The primers used in step (iii) (and optionally step (iv)) are preferably complementary to at least a portion of the sequence resulting from the treatment with the reagent of the double stranded DNA molecules obtained in step (ii). This embodiment is showed in FIG. 6.

Subsequent amplification steps with a pair of primers may also be possible. Any combination of primers is encompassed by the present invention. For example, the first primer may be complementary to at least a portion of the complementary sequence of the 5' region of the first DNA strand of the adapter molecule and the second primer may be complementary to the 3' region of the molecule obtained after the first amplification step (FIG. 6).

Figure 12:
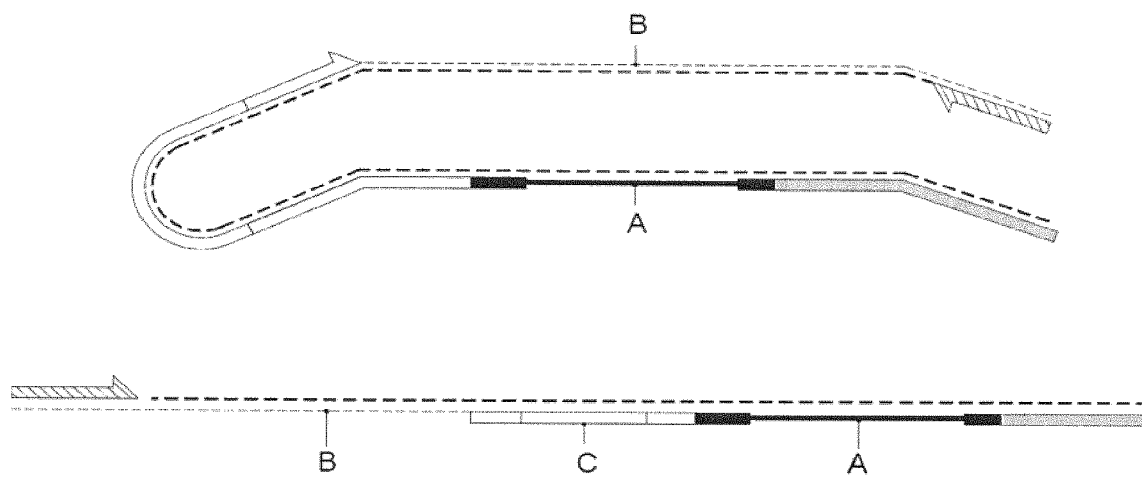
FIG. 12. Schematic diagram showing the amplification step of the products of several embodiments of the method of the invention. Distribution of the original sequence (A)

FIG. 12 shows the arrangement of the different elements in the double stranded DNA library obtained by the present embodiment. Of note, different amplifications with different conditions can be performed on aliquots of the same sample, in a way that any biases (TA or CG biases) can be assessed and considered in the analysis phase.

Optionally, the molecules obtained after steps (iii) and/or (iv) of the method of the invention may be recovered from the reaction mixture. Therefore, the molecules obtained in steps (iii) and/or (iv) may be recovered from the reaction mixture, preferably using a first member of a binding pair, wherein the primers used in steps (iii) and/or (iv) are modified with a second member of said binding pair.

Optionally, the combinatorial sequence may contain modified cytosines which are resistant to treatment with a reagent which allows conversion of non-methylated cytosines to a base that is detectably dissimilar to cytosine in terms of hybridization properties. The combinatorial sequence may alternatively or in addition contain non-modified cytosines (which are not resistant to treatment with a reagent which allows conversion of non-methylated cytosines to a base that is detectably dissimilar to cytosine in terms of hybridization properties).

The expressions "population of double stranded DNA molecules", "ends", "compatible", "ligation", "template", "primer", "complementary", "library of adapters", "combinatorial sequence" or "combinatorial barcode", "reaction mixture", "binding pair", "first member of a binding pair", "second member of a binding pair" and "base that is detectably dissimilar to cytosine in terms of hybridization properties" are defined in the context of the method of the invention.

The Y-adapter may be provided immobilized in a support. Preferably said immobilization is carried out by binding the 5' end of the first DNA strand or a nucleotide of the hairpin loop of the second DNA strand of the Y-adapter, should this be present, to said support. The primers used in step (iii) may also be attached to the support. The binding of the adapter and/or the primers to the support may preferably be a covalent binding.

The terms "immobilized", "support" and "covalent binding" have been defined above. For example, the plurality of paired adaptor-modified DNA molecules of step (i) of the method of the present invention is obtained by:
(a) contacting the population of double stranded DNA molecules with a DNA Y-adapter, said adapter comprising a first DNA strand and a second DNA strand, wherein the 3' region of the first DNA strand and the 5' region of the second DNA strand form a double stranded region by sequence complementarity and wherein the ends of said double stranded region are compatible with the ends of the double stranded DNA molecules,
wherein said contacting is carried out under conditions adequate for the ligation of the Y-adapter to both ends of the double stranded DNA molecules, thereby obtaining a plurality of Y-adapter-containing DNA molecules,
(b) contacting each strand of said Y-adapter-containing DNA molecules with an elongation primer which comprises a 3' region which is complementary to the second DNA strand of the Y-adapter molecule under conditions adequate for the hybridization of the elongation primer to the second strand of the Y-adapter and which, after hybridization with the second DNA strand of the Y-adapter molecule creates overhanging ends,
(c) contacting the molecules generated in step (b) with a hairpin adapter, said hairpin adapter comprising a hairpin loop region and overhanging ends which are compatible with the overhanging ends in the molecules generated in step (b) under conditions adequate for the ligation of the hairpin adapter to the molecules generated in step (b),
(d) converting each of the strands of the DNA molecules obtained in step (c) into a double-stranded DNA molecule by polymerase elongation from the elongation primer used in step (b),
wherein the step of ligation to the hairpin adapter (c) and the elongation step (d) can be carried out in any order or simultaneously.

The terms "Y-adapter" and "Y-adaptor" are used interchangeably and, similarly as above, refer to an adapter formed by two DNA strands wherein the 3' region of the first DNA strand and the 5' region of the second DNA strand form a double stranded region by sequence complementarity and wherein the ends of said double stranded region are compatible with the ends of the double stranded DNA molecules. In this case, the Y-adapter does not comprise a hairpin loop, namely the 3' region of the second DNA strand of the Y-adapter does not form a hairpin loop by hybridization between a first and a second segment within said 3' region.

Preferably, the double stranded DNA molecules used in step (a) are fragments of genomic DNA. Preferably, the double stranded DNA molecules used in step (a) are end-repaired prior to said step (a), preferably further comprising a step of dA-tailing the DNA molecules after the end-repairing step.

The contacting step (a) is carried out under conditions adequate for the ligation of the Y-adapter to both ends of the double stranded DNA molecules.

The result of said step is a plurality of Y-adapter containing DNA molecules that are double stranded DNA molecules having one Y-adapter ligated to each end of the molecule.

The second step (b) involves contacting each strand of the Y-adapter-containing DNA molecules with an elongation primer.

The term "elongation primer", as used herein, refers to a primer used for elongation in the next step of the method that comprises a 3' region which is complementary to the second strand of the Y-adapter molecule creating overhanging ends. The terms "primer" and "overhanging ends" are defined above.

The third step (c) involves contacting the molecules generated in step (b) with a hairpin adapter under conditions adequate for the ligation of the hairpin adapter to the molecules generated in step (b).

The term "hairpin adapter", as used herein, refers to a duplex formed by a single-stranded nucleic acid that doubles back on itself to form a double stranded region maintained by base-pairing between complementary base sequences of the same strand, a hairpin loop region formed by unpaired bases and overhanging ends which are compatible with the overhanging ends in the molecules generated in step (b).

Figure 7:
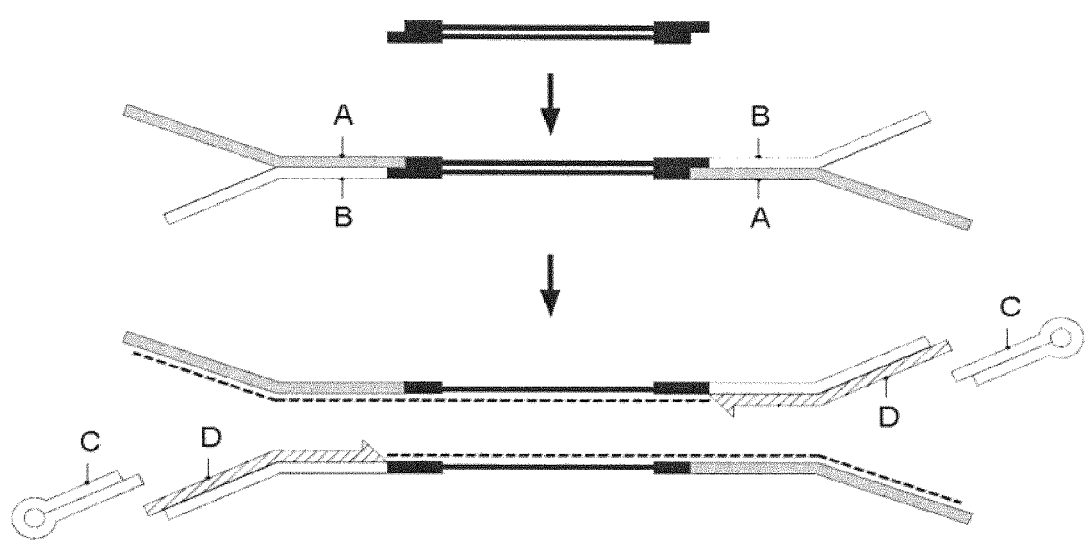
FIG. 7. Schematic diagram showing one embodiment of the method of the invention. Ligation step [step (i)]. Genomic fragments (black line) from the sample preparation step are ligated to two Y-adapters, each formed by a first DNA strand (A) and a second DNA strand (B). An elongation primer (D) hybridizes to the second strand of the Y-adapter molecule creating overhanging ends compatible with a hairpin adapter (C). The elongation primer (D) is used for polymerase elongation to obtain a synthetic strand (dashed line).

FIG. 7 shows an embodiment of the method of the invention wherein the hairpin adapter and the elongation primer are provided separately.

Alternatively, step (b) of contacting each strand of said Y-adapter-containing DNA molecules with an elongation primer and step (c) of contacting the molecules generated in step (b) with a hairpin adapter are carried out in a single step by providing the hairpin adapter and the elongation primer as a complex.

Figure 8:
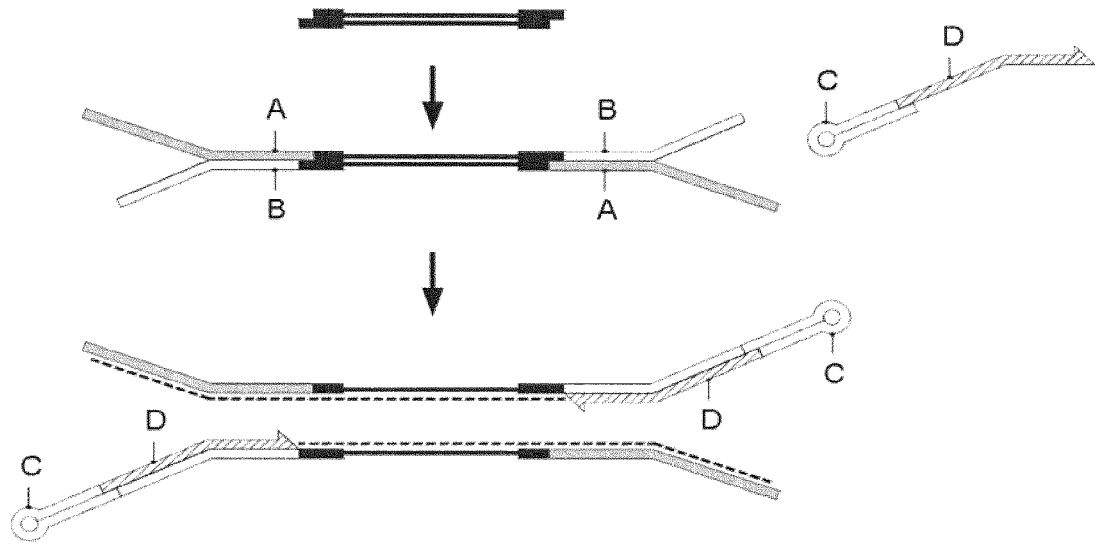
FIG. 8. Schematic diagram showing an embodiment of the method of the invention wherein the hairpin adapter (C) and the elongation primer (D) are provided as a complex. Ligation step [step (i)]. Genomic fragments (black line) from the sample preparation step are ligated to two Y-adapters, each formed by a first DNA strand (A) and a second DNA strand (B). A complex formed by the hairpin adapter (C) and the elongation primer (D) hybridizes to the second strand of the Y-adapter molecule and is used for polymerase elongation to obtain a synthetic strand (dashed line).
Figure 9:
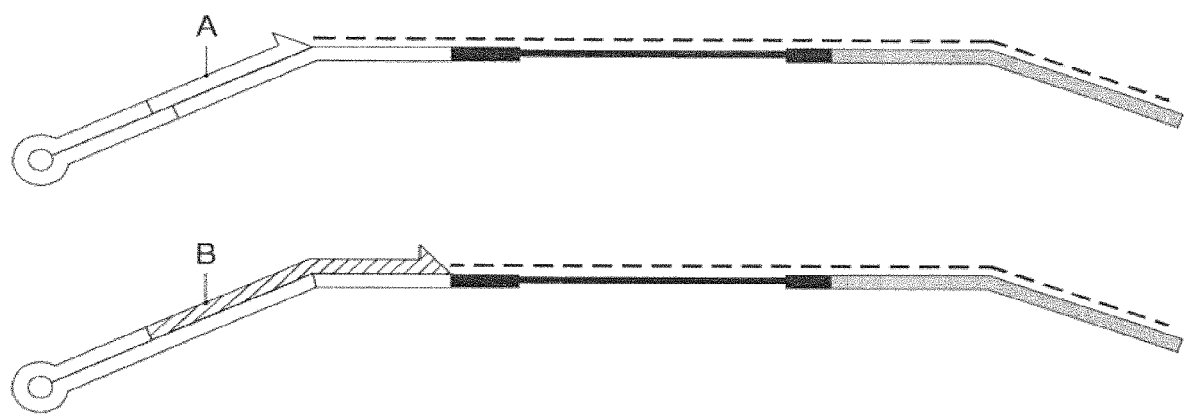
FIG. 9. Schematic diagram showing two further embodiments of the method of the invention wherein the hairpin adapter and the elongation primer (A or B) are provided as a complex.

The term "complex", as used herein, refers to a unique molecule formed by the hairpin adapter and the elongation primer. FIGS. 8 and 9 show different embodiments according to the method of the invention wherein the elongation primer and the hairpin adapter are provided as a complex in different conformations. In this case, after the ligation of the Y-adapter, the elongation primer contained in the complex is annealed and a ligation is carried out between the 3' end of the second strand of the Y-adapter and the 5' end of the hairpin adapter.

The step of ligation to the hairpin adapter (c) and the elongation step (d) can be carried out in any order or simultaneously. In an embodiment, step (c) is carried out before step (d). In another embodiment step (d) is carried out before step (c) (i.e. the elongation is performed before the hairpin adapter is ligated to the construct). In another embodiment steps (c) and (d) are carried out simultaneously.

Preferably, the Y-adapter-containing DNA molecules obtained in step (a) or in step (c) are placed under conditions adequate for separating the strands of said Y-adapter-containing DNA molecules.

The constructs obtained after step (d) form a double stranded DNA library, and can be used for sequencing or in other conventional molecular biology techniques.

The Y-adapter is provided as a library of adapters wherein each member of the library is distinguishable from the others by a combinatorial sequence (also referred to as barcode sequence) located within the double stranded region formed by the 3' region of the first DNA strand and the 5' region of the second DNA strand of the adapter, in order to pair the plurality of fragments of double-stranded DNA molecules (the original strand and its complementary original strand).

Optionally, the Y-adapter, the elongation primer and/or the hairpin adapter incorporate bases labeled with the second member of a binding pair that allows the recovery of the original DNA template after the elongation or amplification steps.

Optionally, the molecules obtained after step (d) may be recovered from the reaction mixture. Therefore, the molecules obtained in step (d) may be recovered from the reaction mixture, preferably using a first member of a binding pair, wherein the primer used in step (e) is modified with a second member of said binding pair.

Once the plurality of paired adaptor-modified DNA molecules have been provided (step (i) of the method of the invention), the paired adapter-containing DNA molecules are treated with a reagent which allows conversion of non-methylated cytosines to a base that is detectably dissimilar to cytosine in terms of hybridization properties (preferably uracil) and wherein the primers used in step (i) (b) above are complementary to at least a portion of the sequence resulting from the treatment with said reagent of the double stranded DNA molecules (step (ii) of the method of the invention).

Preferably, the reagent is bisulfite.

Optionally, in order to avoid that a specific portion of the sequence of the combinatorial sequences (barcode sequences) changes after the treatment with said reagent, the sequence of the combinatorial sequence may contain modified cytosines which are resistant to treatment with the reagent which allows conversion of non-methylated cytosines to a base that is detectably dissimilar to cytosine in terms of hybridization properties For example, the hairpin adapter and/or the Y-adapter may be provided immobilized in a support, as previously described. Preferably said immobilization is carried out by binding a nucleotide of the hairpin loop of the hairpin adapter and/or the 5' end of the first DNA strand of the Y-adapter to said support.

In another embodiment the primer used in step (i)(d) as described above for the present embodiment, and optionally in steps (iii) and, optionally, (iv) of the method of the invention (for optionally amplifying the partially transformed paired double-stranded DNA molecules is also attached to the support. Preferably, the binding between the adapter and/or the primer to the support is a covalent binding.

Third Embodiment of the Method of the Invention

In the third embodiment of the method of the invention, the plurality of paired adaptor-modified DNA molecules of step (i) of the method of the present invention is obtainable by:

(a) fragmenting a plurality of double stranded DNA molecules under conditions adequate for generating a plurality of fragments of the double stranded DNA molecules with overhanging ends wherein each end of each fragment is bound to an hemiadapter molecule, said hemiadapter molecule comprising a first DNA strand and, optionally, a second DNA strand, wherein the second strand forms a double stranded region with the first strand through complementarity with a central region of the first strand and wherein the hemiadapter molecules are bound to the fragments of the double stranded DNA molecules between the 3' end of the first strand of the hemiadapter and the overhanging ends of the fragments of the double stranded DNA molecules, (b) adding an alternative second strand or replacing the second DNA strand of the hemiadapter molecule with an alternative second strand, wherein the 5' region of said alternative second strand is complementary to the 3' region of the first strand of the hemiadapter molecule, said alternative second strand containing a region which is not complementary to the first strand of the hemiadapter molecule, thereby generating a plurality of Y-adapter-modified DNA molecules, (c) optionally, filling gaps existing between the 5' end of the alternative second strand of the Y-adapter and the 3' end of each DNA fragment, (d) contacting each strand of said Y-adapter-containing DNA molecules with an elongation primer which comprises a 3' region which is complementary to the alternative second DNA strand of the Y-adapter molecule and a 5' region which does not hybridize with the alternative second DNA strand of the Y-adapter, under conditions adequate for the hybridization of the elongation primer to the alternative second strand of the Y-adapter, (e) pairing the molecules generated in step (d). The pairing may preferably be achieved by contacting the molecules generated in step (d) with a hairpin molecule, said hairpin molecule comprising a hairpin loop region and ends which are compatible with the ends in the molecules generated in step (d) under conditions adequate for the ligation of the hairpin adapter to the molecules generated in step (d); optionally, the pairing may be achieved by the presence of barcode sequences (in the absence of hairpin molecule), either added after step (d), or already present in the Y-adapter and/or elongation primer;

(f) converting each of the strands of the DNA molecules obtained in step (e) into a double-stranded DNA molecule by polymerase elongation from the elongation primer used in step (d), obtaining a plurality of paired adaptor-modified DNA molecules, wherein the step of ligation to the hairpin adapter (e) and the elongation step (f) can be carried out in any order or simultaneously.

This third embodiment of the invention is adapted for different fragmentation systems.

In a first step, the method for generating a double stranded DNA library according to the third embodiment of the invention involves fragmenting the plurality of double stranded DNA molecules under conditions adequate for generating a plurality of fragments of the double stranded DNA molecules with overhanging ends wherein each end of each fragment is bound to an hemiadapter molecule between the 3' end of the first strand of the hemiadapter and the overhanging ends of the fragments of the double stranded DNA molecules.

The terms "hemiadapter" and "hemiadaptor" are used interchangeably and refer to an incomplete adapter formed by a first DNA strand and, optionally, a second DNA strand, wherein the second strand forms a double stranded region with the first strand through complementarity with a central region of the first strand. The hemiadapter of the present embodiment does not comprise a hairpin loop. For example, the hemiadapter does not comprise a second DNA strand. For example, the hemiadapter comprises a first and a second DNA strand.

Preferably, the double stranded DNA molecules used in step (a) are fragments of genomic DNA.

The first step of the present embodiment comprising fragmentation and ligation of the hemiadapter to the double stranded DNA molecules may be performed, for example, by in vitro transposition wherein a transposable element is introduced from a donor DNA (the hemiadapter molecules) into a target DNA (the population of double stranded DNA molecules).

Preferably, the fragmenting step (a) is carried out by a method which comprises contacting the population of double stranded DNA molecules with a transposase dimer loaded with double stranded adapter molecules, wherein the adapter molecules comprise a double stranded region comprising a Tn5 inverted repeat and a 5' overhang of one of the strands, wherein the cytosine nucleotides in the double stranded region which does not form part of the Tn5 inverted repeat and in the single stranded region are optionally methylated and wherein the contacting is carried out under conditions adequate for fragmentation of the DNA and for the attachment of the hemiadapter molecules to both ends of each DNA fragment.

The term "transposase", as used herein, refers to an enzyme (E.C number 3.1.-.-) that can recognize specific DNA sequences, cleave two duplex DNA molecules in four places and ligate strands. The transposase forms a complex with a nucleic acid that is capable of transposition, i.e. catalyzes the insertion of the nucleic acid into a target DNA sequence.

The expression "transposase dimer", as used herein, refers to a dimer of two chemically identical monomers of a number of residues. Any transposase dimer from any species may be used in the present invention, either natural or mutant. Of particular interest are, without limitation, transposases Tn5, Tn3, Tn7 and its mutants, and also retroviral integrases. In a preferred embodiment the transposase dimer is Tn5 transposase. The term "Tn5 transposase" refers to a member of the RNAse superfamily of proteins which includes retroviral integrases. The Tn5 transposase of the present invention is found in *Escherichia coli* and is defined by the sequence Q46731 of UniProt database, version of Apr. 3, 2013. The invention includes also functional equivalent variants of said Tn5 transposase comprising natural variants that appear in other species (for example in *Shewanella*) and artificial variants obtained by molecular biology techniques (for example the mutant Tn5 transposase disclosed in U.S. Pat. No. 5,965,443).

The term "loaded", as used herein, means that the transposase dimer is bound to a fragment of duplex DNA.

The expression "double stranded adapter molecule", in the context of the present embodiment, refers to an adapter molecule comprising a double stranded region comprising a Tn5 inverted repeat and a 5' overhang of one of the strands.

The expression "Tn5 inverted repeat", as used herein, refers to a transposable element. Said Tn5 inverted repeat is generally thought to be 18 or 19 bases in length and is inverted repeat relative to another Tn5 inverted repeat (Johnson R. C. and Reznikoff W. S. 1983. Nature, 304:280). The Tn5 inverted repeat sequences are well known in the state of the art.

The cytosine nucleotides in the double stranded region which does not form part of the Tn5 inverted repeat and in the single stranded region may be methylated or not methylated. In a particular embodiment said cytosine nucleotides are methylated. The expression "conditions adequate for fragmentation of the DNA and for the attachment of the hemiadapter molecules to both ends of each DNA fragment", as used in the context of the present embodiment, refers to the adequate conditions of time, temperature and buffer composition for the loaded transposase dimer enzyme to work properly. Said conditions are well known by the person skilled in the art. Exemplary conditions can be those disclosed in Adey A. and Shendure J. 2012. Genome Research, 22:1139-1143 and in Adey A. et al. 2010. Genome Biology, 11: R119.

Suitable kits for the first step (a) of the present embodiment are, for example, Nextera™ DNA sample preparation kits (Illumina).

The in vitro transposition may be carried out by using tagmentation ("Ultra-low-input, tagmentation-based-whole-genome bisulfite sequencing" Adey A. and Shendure J. 2012. Genome Research, 22:1139-1143; "Rapid, low-input, low-bias construction of shotgun fragment libraries by high-density in vitro transposition" Adey A. et al. 2010. Genome Biology, 11: R119) or a modification of the tagmentation method disclosed in patent U.S. Pat. No. 5,965,443. Other methods that may be used in the present invention include, without limitation, those disclosed in EP2527438A1, US2003143740A, U.S. Pat. No. 7,160,682B and WO9925817A.

The result of said step (a) is a plurality of hemiadapter-containing DNA molecules that are double stranded DNA molecules having one hemiadapter ligated to each end of the molecule.

The second step (b) of the present embodiment involves adding an alternative second strand or replacing the second DNA strand of the hemiadapter molecule with an alternative second strand obtaining a plurality of Y-adapter-containing DNA molecules.

The expression "replacing" as used herein, means that the second DNA strand of the hemiadapter is substituted by an alternative second strand. The replacement occurs under conditions where the initial second DNA strand of the hemiadapter loses affinity with respect to the alternative second strand, by controlling the temperature, strand concentration and strand melting temperature in the reaction. Briefly, the initial second DNA strand loses hybridization with the first strand of the hemiadapter by increasing the temperature, for example to 50° C. during 2 minutes, in a suitable buffer. Then, the mixture is cooled and the alternative second strand replaces the initial second DNA strand. Exemplary conditions for replacing the second DNA strand of the hemiadapter are disclosed in Adey A. and Shendure J. 2012. Genome Research, 22:1139-1143.

The expression "alternative second strand", as used herein, refers to a strand having a 5' region complementary to the 3' region of the first strand of the hemiadapter molecule and containing a region which is not complementary to the first strand of the hemiadapter. In an embodiment the 5' region of the alternative second strand complementary to the 3' region of the first strand of the hemiadapter molecule does not have any gap between the 5' end of the alternative second strand and the 3' end of the DNA fragment. In another embodiment a gap is present between the 5' end of the alternative second strand and the 3' end of the DNA fragment.

The expression "Y-adapter", in the context of the present embodiment, refers to an adapter formed by two DNA strands wherein the 3' region and/or the central region of the first DNA strand and the 5' region of the alternative second strand form a double stranded region by sequence complementarity and wherein the 5' region of the first strand and the 3' region of the alternative second strand are not complementary.

In some cases, the 5' end of the alternative second strand of the Y-adapter and the 3' end of each DNA fragment are not ligated since gaps may exist between the ends.

Optionally, present embodiment involves step (c) of filling gaps existing between the 5' end of the alternative second strand of the Y-adapter and the 3' end of each DNA fragment.

The term "gap", as used herein, refers to a discontinuity in one of the two DNA strands due to the loss of one or more nucleotides.

The expression "filling gaps", as used herein, refers to adding the missing nucleotides in a strand. A DNA polymerase inserts the correct nucleotide into the gap and links it to the nucleotide on the 3' end of the strand by recognizing which base is opposite to the gap on the complementary DNA strand. Since there is a nick at the gap, the DNA strands on both sides of the nick are ligated by using a DNA ligase.

When the first DNA strand of the hemiadapter contains a combinatorial sequence the step (c) of the present embodiment generates a complementary copy of said combinatorial sequence by gap filling.

Step (d) of the present embodiment involves contacting each strand of the Y-adapter-containing DNA molecules with an elongation primer under conditions adequate for the hybridization of the elongation primer to the alternative second strand of the Y-adapter.

The term "elongation primer", as used in the context of the present embodiment, refers to a primer used for elongation in subsequent steps of the method that comprises a 3' region which is complementary to the alternative second DNA strand of the Y-adapter and a 5' region which preferably does not hybridize with the alternative second DNA strand of the Y-adapter.

Step (d) of the present embodiment may generate blunt ends or overhanging ends, preferably overhanging ends.

Step (e) of the present embodiment involves pairing the molecules generated in step (d), preferably by contacting the molecules generated in step (d) with a hairpin adapter under conditions adequate for the ligation of the hairpin adapter to the molecules generated in step (d). Optionally, the pairing may be achieved by the presence of barcode sequences (in the absence of hairpin molecule), either added after step (d), or already present in the Y-adapter and/or elongation primer.

The term "hairpin adapter", "hairpin sequence" and/or "hairpin molecule", in the context of the present embodiment refers to a duplex formed by a single-stranded nucleic acid that doubles back on itself to form a double stranded region maintained by base-pairing between complementary base sequences of the same strand, a hairpin loop region formed by unpaired bases and ends which are compatible with the ends in the molecules generated in step (d). The hairpin adapter may contain blunt ends or overhanging ends, preferably overhanging ends.

In another case of the present embodiment step (d) of contacting each strand of said Y-adapter-containing DNA molecules with an elongation primer and step (e) of contacting the molecules generated in step (d) with a hairpin molecule, are carried out in a single step by providing the hairpin adapter and the elongation primer as a complex.

Figure 10:
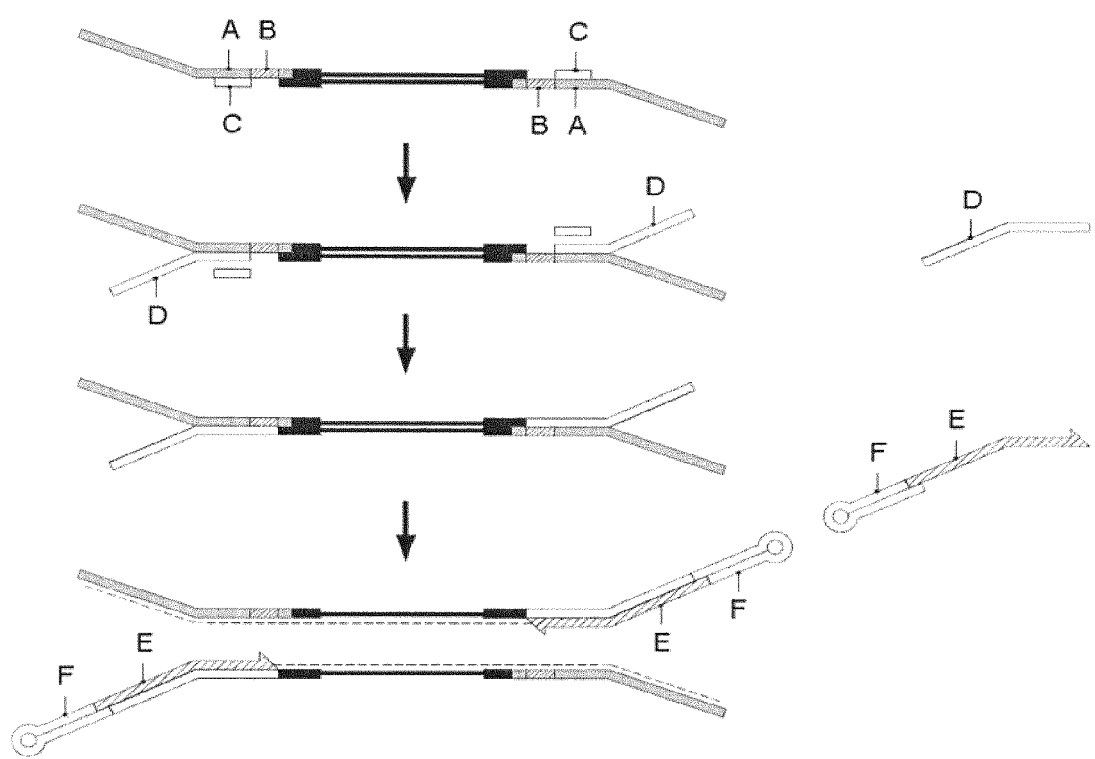
FIG. 10. Schematic diagram showing an embodiment of the method of the invention wherein the hairpin adapter (hairpin sequence or hairpin molecule) (F) and the elongation primer (E) are provided as a complex. Fragmenting and ligation step. Genomic fragments (black line) are bound to a hemiadapter molecule comprising a first DNA strand (A) and a second DNA strand (C) and having a combinatorial sequence (B) in the first DNA strand. Replacing step. The second DNA strand (C) of the hemiadapter is replaced by an alternative second strand (D). Gap filling step. Gaps existing between the 5' end of the alternative second strand and the 3' end of the DNA fragment are filled. A complex formed by the hairpin adapter (F) and the elongation primer (E) hybridizes to the alternative second strand of the Y-adapter molecule and is used for polymerase elongation to obtain a synthetic strand (dashed line).

The term "complex", as used herein, refers to a unique molecule formed by the hairpin adapter and the elongation primer. FIG. 10 shows an example according to the present embodiment wherein the elongation primer and the hairpin adapter are provided as a complex. In this case, the elongation primer contained in the complex is annealed and a ligation is carried out between the 3' end of the alternative second strand of the Y-adapter and the 5' end of the hairpin adapter.

In another case of the present embodiment step (b) of adding an alternative second strand or replacing the second DNA strand of the hemiadapter molecule with an alternative second strand, step (d) of contacting each strand of said Y-adapter-containing DNA molecules with an elongation primer and step (e) of contacting the molecules generated in step (d) with a hairpin molecule, are carried out in a single step by providing the alternative second strand, the hairpin adapter and the elongation primer as a complex.

Figure 11:
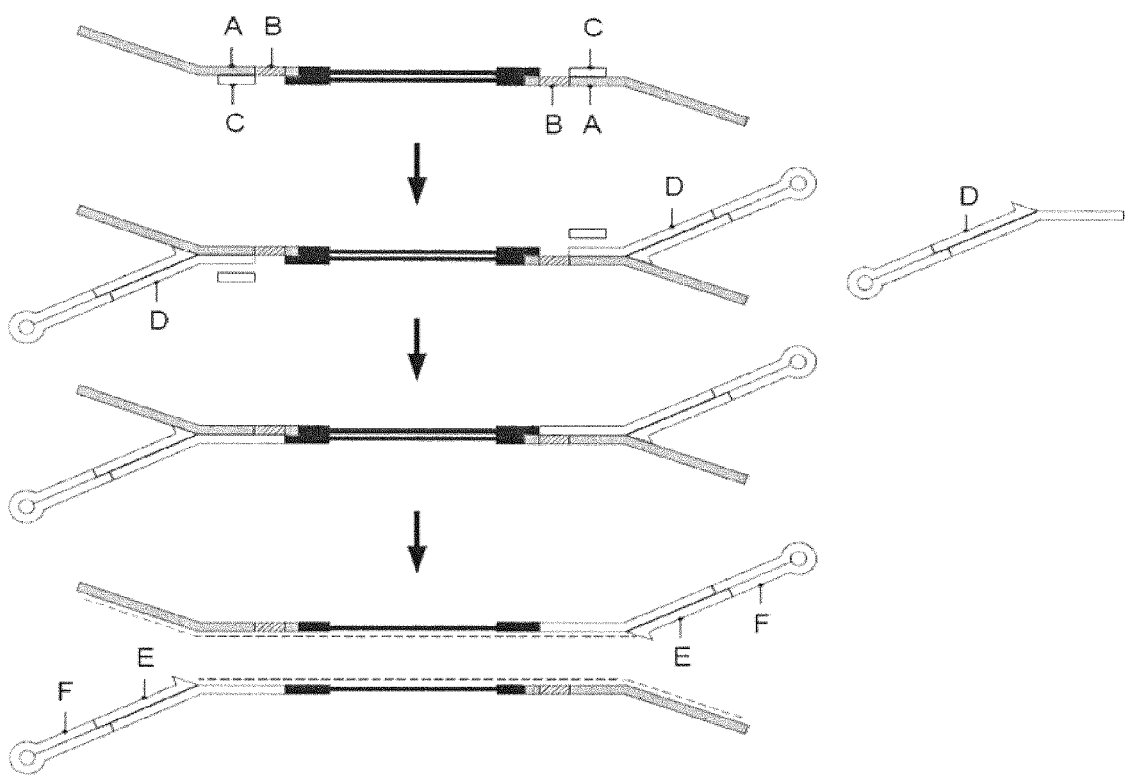
FIG. 11. Schematic diagram showing a further embodiment of the method of the invention wherein the alternative second strand (D), the hairpin adapter (F) and the elongation primer (E) are provided as a complex.

The term "complex", as used herein, refers to a unique molecule formed by the alternative second strand, the hairpin adapter and the elongation primer. FIG. 11 shows an embodiment according to the present embodiment, wherein the alternative second strand, the elongation primer and the hairpin molecule are provided as a complex. In this case, the alternative second strand contained in the complex is annealed to the first DNA strand of the hemiadapter molecule. Step (c) of gap filling and step (f) of elongation may be carried out at the same time when a DNA polymerase and a DNA ligase are added; or they may be carried out separately when the 3' end of the elongation primer is reversibly blocked. Preferably, steps (b) to (f) are carried out simultaneously.

In the present embodiment, the step of ligation to the hairpin molecule (e) and the elongation step (f) can be carried out in any order or simultaneously.

In a preferred embodiment the Y-adapter containing DNA molecules obtained in step (b) or, as the case may be, in step (c) or the paired adapter-containing DNA molecules obtained in step (e) or, as the case may be, in step (f) are placed under conditions adequate for separating the strands of said molecules.

The constructs obtained after step (f) of the present embodiment form a double stranded DNA library and can be used for sequencing or in other conventional molecular biology techniques.

Preferably, the hemiadapter used in step (a) is provided as a library of hemiadapters, each member of the library being distinguishable from the others by a combinatorial sequence in the 3' region of the first strand of the hemiadapter. For example, the second strand of the hemiadapter or the alternative second strand used in step (b) does not show any substantial overlap with said combinatorial region. In another example, the second strand of the hemiadapter or the alternative second strand used in step (b) show a substantial overlap with said combinatorial region.

The expression "does not show any substantial overlap", as used herein, means that the second strand of the hemiadapter or the alternative second strand used in step (b) does not extend and cover the combinatorial region. The expression "show a substantial overlap", as used herein, means that the second strand of the hemiadapter or the alternative second strand used in step (b) extends and covers partially or completely the combinatorial region.

Optionally, the Y-adapter, the elongation primer and/or the hairpin adapter and/or the barcode sequences, if present, incorporate bases labeled with the second member of a binding pair that allows the recovery of the original DNA template after the elongation or amplification steps.

Optionally, the molecules obtained after step (f) of the present embodiment may be recovered from the reaction mixture. Therefore, in an embodiment of the present embodiment of the invention the molecules obtained in step (f) are recovered from the reaction mixture, preferably because the Y-adapter, the elongation primer and/or the hairpin molecule and/or, if the case is this, the barcode sequence(s) incorporate bases labeled with the second member of a binding pair that allows the recovery of the original DNA template after the elongation or amplification steps.

Once the plurality of paired adaptor-modified DNA molecules have been provided (step (i) of the method of the invention) according to the present embodiment, the (non-methylated) cytosine present in both strands of the paired adaptor-modified DNA molecules are transformed to e.g. uracil in the paired adaptor-modified DNA molecules (step (ii) of the method of the invention).

Accordingly, the plurality of paired adaptor-modified DNA molecules are treated with a reagent which allows conversion of non-methylated cytosines to a base that is detectably dissimilar to cytosine in terms of hybridization properties and wherein the primers used in step (g) are complementary to at least a portion of the sequence resulting from the treatment with said reagent of the double stranded DNA molecules obtained in step (f).

Preferably the reagent is bisulfite.

Optionally, the combinatorial sequence (barcode sequence), if present, may contain one or more modified cytosines which are resistant to treatment with a reagent which allows conversion of non-methylated cytosines to a base that is detectably dissimilar to cytosine in terms of hybridization properties. The combinatorial sequence may alternatively or in addition contain non-modified cytosines (which are not resistant to treatment with a reagent which allows conversion of non-methylated cytosines to a base that is detectably dissimilar to cytosine in terms of hybridization properties).

Once the plurality of paired and transformed adaptor-modified DNA molecules have been generated (step (ii) of the method of the invention), complementary strands of the paired and transformed adaptor-modified DNA molecules are provided (step (iii) of the method of the invention).

Preferably, step (iii) of the method of the invention is performed using a primer the sequence of which is complementary to at least a portion of the complementary sequence of the 5' region of the first DNA strand of the hemiadapter molecule (preferably resulting from the treatment with the reagent of the double stranded DNA molecules (step (ii) of the method of the invention)).

Preferably, step (iii) of the method of the invention is performed using a primer the sequence of which is complementary to at least a portion of the complementary sequence of the population of double stranded DNA molecules used for generating the paired and transformed adaptor-modified DNA molecules (preferably complementary to the sequence resulting from the treatment with the reagent of the double stranded DNA molecules (step (ii) of the method of the invention, as described above).

Subsequent amplification steps with a pair of primers may also be possible (step (iv) of the method of the invention). Any combination of primers is encompassed by the present invention. For example, in a particular embodiment the primer of step (iii) is complementary to at least a portion of the complementary sequence of the 5' region of the first DNA strand of the hemiadapter molecule and the primer of step (iv) is complementary to the 3' region of the molecule obtained after the first amplification step.

Optionally, the molecules obtained after step (iii) and/or step (iv) may be recovered from the reaction mixture. Therefore, the molecules obtained in step (iii) and/or step (iv) are recovered from the reaction mixture, preferably using a first member of a binding pair, wherein the primer used in step (iii) and/or step (iv) is modified with a second member of said binding pair.

In the present embodiment, the hairpin adapter and/or the first DNA strand of the hemiadapter may be provided immobilized in a support. Preferably said immobilization is carried out by binding a nucleotide of the hairpin loop of the hairpin adapter and/or the 5' end of the first DNA strand of the hemiadapter to said support. In the present embodiment, the primer used in step (iii) and/or step (iv) may also be attached to the support. Preferably, the binding between the adapter and/or the primer to the support is a covalent binding.

Further Embodiments of the Method of the Invention

1. Method of the Invention Wherein the Pairing of the Strands of the Plurality of Double-Stranded DNA Molecules is Achieved by the Presence of Barcode Sequences For example, the plurality of paired adaptor-modified DNA molecules of step (i) of the method of the present invention may be obtainable by ligating the population of double stranded DNA molecules with a population of DNA adapters, each adapter comprising a first DNA strand and a second DNA strand, wherein the 3' region of the first DNA strand and the 5' region of the second DNA strand form a double stranded region by sequence complementarity and wherein the ends of said double stranded region are compatible with the ends of the double stranded DNA molecules, wherein each adapter of the population is distinguishable from the others by a combinatorial sequence located within the double stranded region formed between the 3' region of the first DNA strand and the 5' region of the second DNA strand, wherein said ligating is carried out under conditions adequate for the ligation of an adapter to each end of the double stranded DNA molecules, thereby obtaining a plurality of adapter-containing DNA molecules.

Accordingly, double stranded DNA libraries particularly useful for analysing the methylation of the sample are obtained, wherein the original sense and antisense strands of a DNA molecule are not physically bound to each other by a linker, but they may be identified by combinatorial labelling (combinatorial sequences or barcode sequences). Particularly, each of the sense and antisense strands is linked to two combinatorial sequences.

The term "DNA library" as used herein, refers to a collection of DNA fragments that have been ligated to adapter molecules in order to identify and isolate the DNA fragments of interest.

The expression "double stranded DNA library", as used herein, refers to a library that contains both strands of a molecule of DNA (i.e. the sense and antisense strands), but wherein said strands are not physically joined by a linker. The sense and antisense strands of an original molecule are identified by combinatorial labelling (combinatorial sequences or barcode sequences) since the sense strand contains two unique combinatorial barcodes that are also present in the antisense strand. Each original strand of a DNA molecule is bound at one end to the first strand of an adapter having a unique combinatorial sequence and at the other end to the second strand of a different adapter having a unique different combinatorial sequence.

The terms "adapter" and "adaptor" are used interchangeably and refer to an oligonucleotide or nucleic acid fragment or segment that can be ligated to a nucleic acid molecule of interest.

The "DNA adapter" as used herein comprises a first DNA strand and a second DNA strand, wherein the 3' region of the first DNA strand and the 5' region of the second DNA strand form a double stranded region by sequence complementarity and wherein the ends of said double stranded region are compatible with the ends of the plurality of double stranded DNA molecules, and wherein each adapter is distinguishable from the others by a combinatorial sequence located within the double stranded region formed between the 3' region of the first DNA strand and the 5' region of the second DNA strand. The DNA adapter may be formed by a first DNA strand and a second DNA strand that are substantially complementary. Therefore, the 5' region of the first DNA strand and the 3' region of the second DNA strand may be complementary. The DNA adapter can be a Y-adapter. Therefore, the DNA adapter may be a Y-adapter wherein the 3' region of the first DNA strand and the 5' region of the second DNA strand may form a double stranded region by sequence complementarity and wherein the 5' region of the first DNA strand and the 3' region of the second DNA strand may not be complementary. FIG. 14 shows a schematic diagram showing this aspect of the method of the invention. Optionally, the DNA adapter may be an adapter according to the adapters disclosed in section "Libraries of Y-adapters of the invention, methods and kits for synthesizing them" of the present description. Any of the embodiments disclosed in said section are applicable to the adapter as used herein. Preferably, the 3' end of the second DNA strand in each adapter is reversibly blocked by a linker that links the 5' end of the first DNA strand and the 3' end of the second DNA strand.

Preferably, the double stranded DNA molecules used in step (i) are fragments of genomic DNA. Optionally, the double stranded DNA molecules used in step (i) are end-repaired prior to said step (i), preferably further comprising a step of dA-tailing the DNA molecules after the end-repairing step, as described above.

Optionally, the plurality of double stranded DNA molecules is treated, prior to step (i) with adapter molecules, under conditions adequate for the ligation of the adapter molecules to the DNA molecules thereby introducing cohesive ends in said DNA molecules.

The ligation step (i) is carried out under conditions adequate for the ligation of an adapter to each end of the double stranded DNA molecules, to yield a plurality of adapter-containing DNA molecules.

The result of said step is a plurality of paired adapter-containing DNA molecules. Each paired adapter-modified DNA molecule will have two different combinatorial sequences, each of them located at one of the adapters ligated to each end of the DNA molecule.

The constructs obtained after step (i) form a double stranded library of the invention, and can be used for sequencing or in other conventional molecular biology techniques. The advantage of these libraries is that the combinatorial sequences allow crossing the sequence information obtained from the sense and antisense strands that were originally together for obtaining a more reliable result.

The adapter-containing DNA molecules obtained in step (i) are treated with a reagent which allows conversion of non-methylated cytosines to a base that is detectably dissimilar to cytosine in terms of hybridization properties (step (ii)).

In a preferred embodiment, the reagent is bisulfite which converts all non-methylated cytosines to uraciles, which will be read as thymines in the molecules amplified in step (iii).

After the treatment of step (ii), complementarity between the sense and antisense strands of the original double-stranded DNA molecules is partially or completely lost. This facilitates the annealing of the primers used in the subsequent steps.

The constructs obtained after step (ii) can also be used for sequencing or in other conventional molecular biology techniques, particularly for analyzing the methylation of a sample.

In the third step of the method of the invention (step (iii)), complementary strands of the paired and transformed adapter-modified DNA molecules obtained in step (ii) are provided. In this step, a primer the sequence of which is complementary to at least a portion of the second DNA strand of the adapter (resulting from the treatment with said reagent of the double stranded DNA molecules (step (ii) of the method of the invention)) is used. This is showed in FIG. 14 and allows obtaining complementary strands for the whole sequence of the population of paired and transformed adaptor-modified double stranded DNA molecules used for generating a double stranded DNA library.

After step (ii) has taken place, the primers used in step (iii) are capable of hybridizing to the paired and transformed adapter-modified DNA molecule when said molecule has been treated with a reagent that converts non-methylated cytosines to a base that is detectably dissimilar to cytosine in terms of hybridization properties. For example, said primers may not be capable of hybridizing to the adapter molecule before it is submitted to said conversion. If the adapter molecule contains non-methylated cytosines, the primers used in step (iii) have an adenine base instead of a guanine base in the positions that pair with the non-methylated cytosines of the original adapter molecule. The adapter molecule may contain methylated or non-methylated cytosines. Optionally, in order to avoid that a specific portion of the sequence of the adapter molecules, hairpin sequences and/or barcode sequences changes after the treatment with said reagent, the sequence of the first adapter molecule and preferably the combinatorial sequence within the adapter sequence may contain modified cytosines which are resistant to treatment with the reagent which allows conversion of non-methylated cytosines to a base that is detectably dissimilar to cytosine in terms of hybridization properties. Adapters may contain non-methylated (non-modified) cytosines.

Of note, different amplifications with different conditions can be performed on aliquots of the same sample, in a way that any biases (TA or CG biases) can be assessed and considered in the analysis phase.

Optionally, the DNA adapter incorporates bases labelled with the second member of a binding pair that allows the recovery of the original DNA template after steps (i), (ii), (iii) or (iv).

Optionally, the DNA molecules obtained in step (i) or in step (ii) of the method of the invention are recovered from the reaction mixture obtained after step (i), step (ii) or, as the case may be, after step (iii) and/or after step (iv), preferably by using a first member of a binding pair, wherein the adapter is modified with a second member of said binding pair, as described above.

Optionally, the DNA molecules obtained in step (iii) and/or after step (iv) are recovered from the reaction mixture, preferably by using a first member of a binding pair, wherein the primers used in step (iii) and/or after step (iv) are modified with a second member of said binding pair.

The combinatorial barcodes allow sample identification, multiplexing, pairing as well as quantitative analysis, and are useful for monitoring biases and error control during the amplification steps. The constructs obtained in this case, have two different identifiers associated to the sense strand that are the same two identifiers associated to the antisense strand. Since both combinatorial sequences are the same for the sense and antisense strands, both strands may be followed during the process. After the whole process, those complementary strands that were originally together will share the same two combinatorial sequences. Two unique identifiers are associated with each individual molecule in the starting sample, thus giving the ability to differentiate between constructs. Said unique identifiers allow identification of a specific construct comprising said identifiers and its descendants since after step (ii) the original sense and antisense strand of a double stranded DNA molecule can be separated, but each of these strands will contain both combinatorial sequences. Therefore, any amplification products of said initial individual molecule bearing the two unique identifiers are assumed to be identical by descent.

This provides the advantage that the sample used as a DNA template may be identified, preserved during the process and recovered, stored and submitted to multiple amplifications with different conditions and sequencings without sample exhaustion.

The expressions "population of double stranded DNA molecules", "combinatorial sequence", "ends", "compatible", "ligation", "template", "primer", "complementary", "amplification", "binding pair", "first member of a binding pair", "second member of a binding pair", "base that is detectably dissimilar to cytosine in terms of hybridization properties" and "modified cytosines" have been defined in the context of the method of the invention.

All the embodiments and definitions used in the method of the invention are applicable to the present example.

2. Method of the Invention Wherein the Pairing of the Strands of the Plurality of Double-Stranded DNA Molecules is Achieved by the Presence of Barcode Sequences For example, the plurality of paired adaptor-modified DNA molecules of step (i) of the method of the present invention may be obtainable by (a) fragmenting the plurality of double stranded DNA molecules under conditions adequate for generating a plurality of fragments of the double stranded DNA molecules with overhanging ends wherein each end of each fragment is bound to an hemiadapter molecule, said hemiadapter molecule comprising a first DNA strand and, optionally, a second DNA strand, wherein each hemiadapter is distinguishable from the others by a combinatorial sequence located within the 3' region of the first DNA strand, wherein the second strand forms a double stranded region with the first strand through complementarity with a central region of the first strand and wherein the hemiadapter molecules are bound to the fragments of the double stranded DNA molecules between the 3' end of the first strand of the hemiadapter and the overhanging ends of the fragments of the double stranded DNA molecules, (b) adding an alternative second strand or replacing the second DNA strand of the hemiadapter molecule with an alternative second strand, wherein the 5' region of said alternative second strand is complementary to the 3' region of the first strand of the hemiadapter molecule, said alternative second strand containing a region which is not complementary to the first strand of the hemiadapter molecule, thereby generating a plurality of Y-adapter-modified DNA molecules, (c) optionally, filling gaps existing between the 5' end of the alternative second strand of the Y-adapter and the 3' end of each DNA fragment, In this case, the plurality of paired-adaptor modified DNA molecules obtained after step (i) of the method of the invention is adapted for different fragmentation systems.

In a first step, the plurality of double stranded DNA molecules are fragmented under conditions adequate for generating a population of fragments of the double stranded DNA molecules with overhanging ends wherein each end of each fragment is bound to an hemiadapter molecule between the 3' end of the first strand of the hemiadapter and the overhanging ends of the fragments of the double stranded DNA molecules.

The term "hemiadapter", as used herein refers to an incomplete adapter formed by a first DNA strand and, optionally, a second DNA strand, wherein the second strand forms a double stranded region with the first strand through complementarity with a central region of the first strand and wherein each hemiadapter is distinguishable from the others by a combinatorial sequence located within the 3' region of the first DNA strand. In an embodiment the hemiadapter does not comprise a second DNA strand. The hemiadapter may comprise a first and a second DNA strand.

Preferably, the second strand of the hemiadapter does not show any substantial overlap with said combinatorial sequence.

Preferably, the double stranded DNA molecules used in step (i) are fragments of genomic DNA.

Optionally, the double stranded DNA molecules used in step (i) are end-repaired prior to said step (i), preferably further comprising a step of dA-tailing the DNA molecules after the end-repairing step.

Optionally, the population of double stranded DNA molecules is treated, prior to step (i) with adapter molecules, under conditions adequate for the ligation of the adapter molecules to the DNA molecules thereby introducing cohesive ends in said DNA molecules.

The first step comprising fragmentation and ligation of the hemiadapter to the double stranded DNA molecules may be performed, for example, by in vitro transposition wherein a transposable element is introduced from a donor DNA (the hemiadapter molecules) into a target DNA (the population of double stranded DNA molecules).

Preferably, the fragmenting step (i) is carried out by a method which comprises contacting the population of double stranded DNA molecules with a transposase dimer loaded with double stranded adapter molecules, wherein the adapter molecules comprise a double stranded region comprising a Tn5 inverted repeat and a 5' overhang of one of the strands, wherein the cytosine nucleotides in the double stranded region which does not form part of the Tn5 inverted repeat and in the single stranded region are optionally methylated and wherein the contacting is carried out under conditions adequate for fragmentation of the DNA and for the attachment of the hemiadapter molecules to both ends of each DNA fragment.

The expression "double stranded adapter molecule", as used herein refers to an adapter molecule comprising a double stranded region comprising a Tn5 inverted repeat and a 5' overhang of one of the strands.

The result of said step is a plurality of hemiadapter-containing DNA molecules that are double stranded DNA molecules having one hemiadapter ligated to each end of the molecule. Each hemiadapter-containing DNA molecule will have two different combinatorial sequences, each of them located within the 3' region of the first DNA strand of the hemiadapter ligated to each end of the DNA molecule.

The second step (b) involves adding an alternative second strand or replacing the second DNA strand of the hemiadapter molecule with an alternative second strand obtaining a plurality of Y-adapter-containing DNA molecules.

The expression "alternative second strand", as used herein, refers to a strand having a 5' region complementary to the 3' region of the first strand of the hemiadapter molecule and containing a region which is not complementary to the first strand of the hemiadapter. Optionally, the 5' region of the alternative second strand complementary to the 3' region of the first strand of the hemiadapter molecule does not have any gap between the 5' end of the alternative second strand of the hemiadapter and the 3' end of the DNA fragment. In another embodiment a gap is present between the 5' end of the alternative second strand of the hemiadapter and the 3' end of the DNA fragment.

Preferably, the alternative second strand does not show any substantial overlap with the combinatorial region of the first DNA strand of the hemiadapter.

The expression "Y-adapter" as used herein refers to an adapter formed by two DNA strands wherein the 3' region and/or the central region of the first DNA strand and the 5' region of the alternative second strand form a double stranded region by sequence complementarity and wherein the 5' region of the first strand and the 3' region of the alternative second strand are not complementary.

In some embodiments the 5' end of the alternative second strand of the Y-adapter and the 3' end of each DNA fragment are not ligated since gaps may exist between the ends.

The constructs obtained after step (b) form the double stranded library of the invention, and can be used for sequencing or in other conventional molecular biology techniques. The advantage of these libraries is that the combinatorial sequences allow crossing the sequence information obtained from the sense and antisense strands that were originally together for obtaining a more reliable result.

Optionally, step (c) involves filling gaps existing between the 5' end of the alternative second strand of the Y-adapter and the 3' end of each DNA fragment.

This step generates a complementary copy of the combinatorial sequence of the first DNA strand of the hemiadapter by gap filling.

Afterwards, the plurality of paired adaptor-modified DNA molecules obtained proceed to steps (ii) and (iii) (and, optionally, to step (iv)) of the method of the present invention, as described above.

Optionally, the Y-adapter incorporates bases labelled with the second member of a binding pair that allows the recovery of the original DNA template. The Y-adapter may comprise methylated cytosines and/or non-methylated cytosines. The expressions "population of double stranded DNA molecules", "combinatorial sequence", "ends", "compatible", "ligation", "template", "primer", "complementary", "amplification", "binding pair", "first member of a binding pair", "second member of a binding pair", "base that is detectably dissimilar to cytosine in terms of hybridization properties" and "modified cytosines" have been defined above.

The expressions "transposase", "transposase dimer", "loaded", "Tn5 inverted repeat", "conditions adequate for fragmentation of the DNA and for the attachment of the hemiadapter molecules to both ends of each DNA fragment", "replacing", "gap", "filling gaps" and "does not show any substantial overlap" have been defined above. The terms "DNA library" and "double stranded DNA library" have been defined above.

Sequencing Step (Step (v) of the Method of the Invention)

The paired DNA molecules (also referred to as double-stranded DNA libraries or DNA libraries) generated in steps (ii), (iii) and/or in step (iv) of the method of the present invention are suitable for sequencing techniques (preferably the paired DNA molecules generated in step (iii) and/or step (iv) are sequenced).

The design of the DNA libraries generated in the method of the present invention allows monitoring any biases produced during the previous steps as well as detecting sequencing and conversion errors better than the currently used methods.

When amplification occurs, some fragments may become selectively amplified for a number of reasons. This undesirable effect is a major problem for quantification purposes, which is critical in many applications for sequencing, specially for the analysis of methylation status of the DNA (since each allele in each cell can have different methylation status, and even samples can have heterogeneous compositions, which make the quantification and bias control a must for most applications).

The double stranded DNA libraries generated in the method of the invention have the advantage that both strands of every double stranded DNA molecule are simultaneously read during sequencing. Said double reading increases the confidence of the method since the systematic potential sequencing errors produced in every individual sequence read can be detected and corrected.

Currently, sequencing machines have error rates that need to be assumed. Most of these errors cannot be depicted and remain hidden in the final results. This has negative consequences on the subsequent processing and analysing of the results. The method of the invention provides up to four sources of information for each nucleotide (the top and bottom strands of a given dsDNA and, as the case may be, their respective synthetic complementary strands) allowing the validation of the reading of each nucleotide, as all readings must be consistent. Thus, the method of invention allows detection and even correction, of errors of the sequence determination (both for primary sequence determination and for methylation of cytosines analysis).

A sequencing error is detected if it only occurs in one of the strands. This error can be correctable if it cannot be confused with asymmetrical methylation and the nucleotide detection confidence is high and the reference genome sequence allows discernment.

Genetic variants (i.e. mutations and SNPs) cannot be confused with sequencing errors, since the alteration must occur in both strands to be considered as actual genetic variant. The double detection of the methods of the invention is, in fact, a validation of the alteration detection. Moreover, since the primary sequence and the methylation information are assessed concurrently, thymines coming from non-methylated cytosines are distinguishable from those thymines coming from mutations or SNPs.

In addition, when combinatorial sequences (barcode sequences) are included within the adapters it is possible to track amplification biases and count unique double stranded DNA molecules initially present in the sample. The quantification is also possible during the sequencing methods of the invention.

The double stranded DNA libraries can be used in any conventional sequencing method including Next Generation Sequencing (NGS) approaches. The methods for generating a double stranded DNA library according to the invention can be integrated in the current and forthcoming pipelines for DNA sequencing, i.e. NGS technologies and others. NGS of the library can be performed with most of the available platforms. Paired-end sequencing may also be used, although it is not required. Paired-end sequencing will allow longer fragments to be studied. Even when the sequencing does not cover the whole molecule, the information based on the pairing of the two strands can be obtained provided the sequenced region includes the complementary regions, and the barcodes, when necessary (see e.g. FIG. 13).

Alternatively, locus specific sequencing can be performed as well.

The libraries obtained according to the method of the invention may be used for sequencing directly from the reaction mixture in which they have been obtained or they may be purified before the sequencing process.

In an aspect, the invention relates to a method for determining the sequence of a population of double stranded DNA molecules comprising generating a library from said population of double stranded DNA molecules using the method of the invention in any of its embodiments, and sequencing the DNA molecules obtained in steps ((ii)), (iii) or, as the case may be, in step (iv) of the method of the invention (step (v) of the method of the invention).

The term "sequencing" or the expressions "determining the sequence" or "sequence determination" and the like means determination of information relating to the nucleotide base sequence of a nucleic acid, particularly involving determination and ordering of a plurality of contiguous nucleotides in a nucleic acid. Said information may include the identification or determination of partial as well as full sequence information of the nucleic acid. Said information refers to the primary sequence of the double stranded DNA library, the epigenetic modifications (for example methylations or hydroximetilations) or both. The sequence information may be determined with varying degrees of statistical reliability or confidence. As explained above, the method of the invention allows obtaining a high confidence when a double stranded DNA molecule is sequenced.

The method of the invention may be further used for sequencing the primary sequence of the double stranded DNA libraries.

The determination of the primary sequence includes the detection of mutations or genetic variants such as polymorphisms (SNPs, etc.).

Preferably, the method of the invention allows determining simultaneously in the same read, both the primary sequence and the methylation of cytosines. By analyzing the output of the sequencing, each read will have the information of the primary sequence (including mutations and SNPs) and the methylation sequence of both strands as well as the combinatorial sequences included in the adapters.

The Identification of Methylated Cytosines

The method of the invention allows for the identification of methylated cytosines in a population of double stranded DNA molecules.

The double stranded DNA molecules (also referred as to double stranded DNA libraries) generated according to the method of the invention (steps (iii) or (iv)) are suitable for the identification of methylated cytosines, as described above.

The presence of methylated cytosine at a given position is determined if a cytosine appears in one of the strands and a guanine appears in the corresponding position in the opposite strand or wherein the presence of an non-methylated cytosine at a given position is determined if a uracil or thymine appears in one of the strands and a guanine appears in the corresponding position in the opposite strand.

The expression "strand", as used herein refers to each chain of a double stranded DNA molecule. If the pairing of two strands occurs via the presence of a hairpin molecule, both strands of the DNA molecule are linked together forming a unique molecule. If the pairing occurs without the presence of a hairpin molecule, the strands of the DNA molecule are in different molecules, namely they are not physically linked together, but may be identified by the combinatorial sequence(s).

The expression "opposite strand", as used herein, in reference to a first strand, may refer to the strand that was complementary to the first strand before the treatment with a reagent that allows the conversion of non-methylated cytosines to a base that is detectably dissimilar to cytosine in terms of hybridization properties. For example, the antisense strand of a DNA molecule is the opposite strand of the sense strand. The term "opposite strand" may be broader than the term "complementary strand" since after the treatment with the reagent the complementarity between the strands may be partially or completely lost.

The expression "corresponding position", as used herein, refers to the same position in the opposite strand (i.e. to the nucleotide position that pairs with a given nucleotide position in the opposite strand although said pairing does not need to be complementary).

The expressions "population of double stranded DNA molecules", "library", "adapter-modified DNA molecules", "reagent", "base that is detectably dissimilar to cytosine in terms of hybridization properties", "primer", "specific" have been defined above.

The term "sequencing" has been defined in the context of the sequencing method of the invention. Therefore, the sequencing step (v) of the method of the invention (for the identification of methylated cytosines) allows obtaining the primary sequence and the methylation information concurrently.

Preferably, the reagent that allows conversion of non-methylated cytosines to a base that is detectably dissimilar to cytosine is bisulfite. Preferably, the base detectably dissimilar to cytosine is thymine or uracil, more preferably is uracil.

The treatment with a reagent (e.g. bisulfite) that allows conversion of non-methylated cytosines to a base that is detectably dissimilar to cytosine in terms of hybridization properties converts all non-methylated cytosines of the molecules obtained in step (i) of the method of the invention to uracil. When said treated molecules are submitted to step (iii) of the method of the invention the complementary DNA molecule that is synthesized will have an adenine in the position where the template molecule has uracil. The molecules (optionally amplified in step (iv) of the method) will have a thymine where there was a uracil in the first molecule (provided thymines and not uracils are used for the amplification). Therefore, the non-methylated cytosines will be read as uracil or thymines at the end of the process.

Upon elongation or PCR amplification, uracil is amplified as thymine while 5-methylcytosine residues remain as cytosines, allowing methylated cytosines to be distinguished from non-methylated cytosines in the original double stranded DNA molecule. A methylated cytosine in the original double stranded DNA molecule can be inferred by the presence of a cytosine in a given position versus a guanine in the corresponding position of the opposite strand when a molecule of the double stranded DNA library is sequenced. A non-methylated cytosine in the original double stranded DNA molecule can be inferred by the presence of a uracil or thymine in a given position versus a guanine in the corresponding position of the opposite strand when a molecule of the double stranded DNA library is sequenced.

When the paired double-stranded DNA molecules (also referred to as DNA libraries) obtained in steps (iii) or (iv) of the method of the invention are used, each read has the reagent converted sequence of both strands of the double stranded DNA molecules. The strands that were originally complementary may be deducted from the combinatorial sequences (barcode sequences or combinatorial barcodes) of each strand if the pairing was achieved by the use of barcodes.

With this information the original sequences of both strands (before conversion with the reagent) may be inferred. Therefore, for each read, the information of the primary sequence (for mapping into the reference genome and assessing polymorphisms) and the methylation status of both strands of the original double stranded DNA molecules are obtained. The combinatorial labeling of the molecules allows the assessment of the reagent converted sequences of both original strands of the double stranded DNA molecules.

The process that allows inferring the sequence of the original double stranded DNA molecule is performed by means of software that processes the output sequence in order to obtain the sequence before the treatment with the reagent and the sequence after the treatment with said reagent for each molecule of the double stranded DNA library. After that, the software crosses the information from each strand and its authentic complementary strand considering that the authentic complementary strand is the strand that was originally bound to the first strand. This information can be obtained directly for the libraries obtained by the method of the invention where both strands are physically joined. This information may be obtained indirectly if the original strands were paired by combinatorial sequences.

The software developed is capable of: (i) integrating the primary sequence and the methylation information, (ii) detecting mutations, SNPs, and CNV (losses and gains), and (iii) detecting sequencing errors and biases.

Since the methylation information of both strands of the original double stranded DNA molecule is determined this allows assessing the hemimethylation or methylation symmetry in each strand.

The terms "hemimethylated" and "asymmetrically methylated" are used interchangeably and refer to a sequence in a duplex DNA, e.g. a CpG, where only one of the two strands is methylated.

Libraries of y-Adapters, Methods and Kits for Synthesizing them

The invention also provides methods and kits for synthesizing the Y-adapters that are used in the method of the invention. The invention also provides kits containing a library of Y-adapters.

The invention also relates to a library of Y-adapters, wherein each Y-adapter comprises a first DNA strand and a second DNA strand, wherein the 3' region of the first DNA strand and the 5' region of the second DNA strand form a double stranded region by sequence complementarity, wherein the 3' region of the second DNA strand may form a hairpin loop by hybridization between a first and a second segment within said 3' region, the first segment being located at the 3' end of the 3' region and the second segment being located in the vicinity of the region of the second DNA strand which forms a double stranded region with the 3' region of the first DNA strand and wherein each member of the library is distinguishable from the others by one or more (preferably one) combinatorial sequence(s) located within the double stranded region formed between the 3' region of the first DNA strand and the 5' region of the second DNA strand, and/or by one or more combinatorial sequence(s) located in the single-stranded region of the Y-adapter. Preferably, the Y-adapter comprises one barcode sequence in the double-stranded region of the Y-adapter and one barcode sequence in the single-stranded region of the Y-adapter. Optionally, the Y-adapter additionally comprises a "site for cut" as described above in the Y-adapter. Preferably, the "site for cut" is located in the single-stranded region of the Y-adapter.

In a preferred embodiment of the library of Y-adapters the combinatorial sequence contains one or more modified cytosines which are resistant to treatment with the reagent which allows conversion of non-methylated cytosines to a base that is detectably dissimilar to cytosine in terms of hybridization properties.

In another embodiment of the library of Y-adapters the 3' end of the second polynucleotide in each adapter is reversibly blocked.

The expression "reversibly blocked", as used herein, refers without limitation to a reversible modification with a reversible blocking group that prevents the polynucleotide from priming for synthesis. Since said modification is reversible, the blocking group may be removed in further steps.

The term "reversible blocking group", as used herein, refers to a group that replaces the 3' OH-group of the 3' end of the polynucleotide to prevent polymerase extension. Exemplary reversible blocking groups are, without limitation, 3'-p; 3'-amino; 3'-inverted 3-3' deoxynucleoside (idN), inosine, 3'-O ethers such as 3'-O-allyl (Intelligent Bio-Systems), 3'-O-methoxymethyl, 3'-O-nitrobenzyl and 3'-O-azidomethyl (Illumina/Solexa); 3'-aminoalkoxyl and 3'-O-amino. Exemplary reversible blocking groups are also those disclosed in Gardner A. F. et al. 2012. Nucleic Acids Research, 40(15):7404-7415 and called Lightning Terminators™ (Lasergen, Inc.). In the context of the present invention, an entire dideoxynucleotide (ddCMP, ddAMP, ddTMP, ddGMP) can also be considered as a "reversible blocking group".

The term "reversible blocking group", as used herein, also includes a linker that links the 5' end of the first DNA strand and the 3' end of the second DNA strand and that can be removed. Said linker may be, without limitation, a typical nucleotide, a modified nucleotide, or a sequence of nucleotides either typical or modified. When the linker is removed, the first and the second DNA strand of the adapter are separated. The adapter may be used for ligation to the population of double stranded DNA molecules in the methods of the invention before or after the linker has been removed. The linker may be linked to a support.

Therefore, in another embodiment of the library of Y-adapters the 3' end of the second polynucleotide in each adapter is reversibly blocked by a linker that links the 5' end of the first DNA strand and the 3' end of the second DNA strand.

In another embodiment of the library of Y-adapters the end segment of the double stranded region formed between the 3' region of the first DNA strand and the 5' region of the second DNA strand in each adapter contains a target site for a restriction endonuclease.

The term "restriction endonuclease" refers to an enzyme that cuts DNA at or near specific recognition nucleotide sequences known as restriction sites or target sites (sequences of oligonucleotides that are recognized by restriction enzymes). Exemplary restriction endonucleases are well known in the state of the art. Restriction endonucleases include, but are not limited to, type I enzymes, type II enzymes, type IIS enzymes, type III enzymes and type IV enzyme. The REBASE database provides a comprehensive database of information about restriction endonucleases (Roberts R. J. et al. 2010. Nucleic Acids Research, 38: D234-D236).

The term "target site", as used herein, refers to the nucleotide sequence specifically recognized by a restriction endonuclease.

In another aspect, the invention relates to a method for producing a DNA Y-adapter comprising the steps of:
  (i) contacting a first single stranded polynucleotide with a second single stranded polynucleotide wherein the 3' region of the first single stranded polynucleotide is complementary to at least a portion of the 5' region of the second polynucleotide,
    wherein the 3' region of the second single stranded polynucleotide forms a hairpin loop by hybridization of a first and a second segment within said 3' region, the first segment being located at the 3' end of the 3' region and the second segment being located in the vicinity of the 5' region of the second polynucleotide and wherein the 3' end of the second polynucleotide is reversibly blocked,
    said contacting being carried out under conditions adequate for the hybridization of the 3' region of the first single stranded polynucleotide and the complementary region within the 5' region of second single stranded polynucleotide, thereby producing a duplex DNA molecule,
  (ii) elongating the 3' end of the first polynucleotide so as to generate within said first single stranded polynucleotide a sequence which is complementary to the 5' region of the second polynucleotide and
  (iii) optionally, unblocking the 3' end of the second polynucleotide.

Step (i) is carried out under conditions adequate for the hybridization of the 3' region of the first single stranded polynucleotide and the complementary region within the 5' region of the members of the population of second single stranded polynucleotide. Conditions adequate for the hybridization have been defined in the context of the first method of the invention.

Step (ii) involves elongation. Suitable conditions for elongation are well known by the person skilled in the art.

Step (iii) involves unblocking the 3' end of the second polynucleotide. The term "unblocking" refers to removing the blocking group from the 3' end of the polynucleotide and restore the 3'-OH group. Suitable conditions for unblocking are conditions that neither destroy the duplex nor damage the DNA and depend on the specific blocking group that is to be removed. For example, the 3'-O-allyl group is cleaved by transition metal catalysis, the 3'-0-methoxymethyl group is cleaved by acid, the 3'-O-nitrobenzyl group is cleaved by light and the 3'-oazidomethylene group is cleaved by phosphines. When the reversible blocking group is a dideoxynucleotide the entire dideoxynucleotide is removed from the 3' end of the second polynucleotide without destroying the duplex (i.e. the pairing between the 3' region of the first single stranded polynucleotide and the complementary region within the 5' region of the second single stranded polynucleotide is maintained). The term "unblocking" also refers to removing the linker that joins the 5' end of the first single stranded polynucleotide and the 3' end of the second single stranded polynucleotide.

In a preferred embodiment of the method for producing a DNA Y-adapter, the elongation carried out in step (ii) is carried out in the presence of modified cytosines which are resistant to treatment with the reagent which allows conversion of non-methylated cytosines to a base that is detectably dissimilar to cytosine in terms of hybridization properties.

In another embodiment the first single stranded polynucleotide and/or the second single stranded polynucleotide used in step (i) also contain modified cytosines.

In another preferred embodiment the method for producing a DNA Y-adapter according to the third method of the invention further comprises treating the Y-adapter with a reagent which allows conversion of non-methylated cytosines to a base that is detectably dissimilar to cytosine in terms of hybridization properties.

In another preferred embodiment the at least one position within the 3' end of the first polynucleotide is guanine and wherein the positions within the 5' region of the second polynucleotide which hybridize with said position or positions within the 3' end of the first polynucleotide are cytosine or methyl-cytosine.

In another preferred embodiment the 5' end of the second single stranded polynucleotide comprises a sequence which, when the complementary strand is formed during elongation step (ii), is replicated onto the complementary strand forming a target site for a restriction endonuclease.

The second single stranded polynucleotide comprises a sequence that may or may not be a palindromic sequence. A palindromic sequence is a nucleic acid sequence that is the same whether read 5' to 3' on one strand or 5' to 3' on the complementary strand.

The expression "replicated onto the complementary strand" means that the complementary strand synthesized contains the complementary and antiparallel sequence of the second single stranded polynucleotide.

The Y-adapters may contain combinatorial barcodes that allow tracking the products of the methods of the invention.

The second single stranded polynucleotide is provided as a library of polynucleotides, wherein each member of the library is distinguishable from the others by a combinatorial sequence (also referred to as barcode sequences or combinatorial barcodes) located within the 5' region of said polynucleotide and wherein said combinatorial sequence is located upstream with respect to the region showing sequence complementarity with the first single stranded polynucleotide, thereby producing a library of DNA Y-adapter molecules. In a more preferred embodiment, the combinatorial sequence contains one or more cytosines which are resistant to treatment with the reagent which allows conversion of non-methylated cytosines to a base that is detectably dissimilar to cytosine in terms of hybridization properties. FIG. 15 shows an embodiment of the method for producing a DNA Y-adapter containing a combinatorial sequence according to the third method of the invention.

The combinatorial sequence is formed by a number of degenerated nucleotides (being each degenerate nucleotide a mix of two or more nucleotides). If X is the number of different degenerated nucleotides in the combinatorial sequence and Y is the length in nucleotides of the combinatorial sequence, the number of different adapters that may be obtained is $X^Y$. For example, if the combinatorial sequence has a length of four nucleotides that may be A, T or G, the number of different adapters is $3^4=81$, and the number of combinations of two adapters in a Y-adapter-containing-DNA molecule is $81^2=6561$. If the combinatorial sequence has a length of five nucleotides that may be A, T or G, the number of different adapters is 243 and the number of combinations of two adapters in a Y-adapter-containing-DNA molecule is 59049.

The expression "upstream", as used herein, refers to the region towards the 5' end of the strand.

In another embodiment the first single stranded polynucleotide and/or the second single stranded polynucleotide are provided immobilized in a support, wherein said immobilization is carried out by binding the 5' end of the first single stranded polynucleotide or a nucleotide of the hairpin loop of the second single stranded polynucleotide to said support. Preferably, said binding is a covalent binding.

In another embodiment, the first single stranded polynucleotide and the second single stranded polynucleotide are joined by a linker between the 5' end of the first single stranded polynucleotide and the 3' end of the second single stranded polynucleotide and said linker is immobilized in a support. The binding of the linker to the support facilitates the elongation step. The binding between the linker and the support may be broken after the synthesis of the Y-adapter has been finished in order to release the adapter. The adapter linked to the support by the linker may also be used for ligating molecules.

The invention also provides kits comprising polynucleotides for obtaining Y-adapters of the method of the invention.

In another aspect, the invention relates to a kit comprising
(i) a first single stranded polynucleotide comprising a 5' region and a 3' region,
(ii) a second polynucleotide comprising a 5' region and a 3' region, wherein the 3' region forms a hairpin loop by hybridization between a first and a second segment within said 3' region, the first segment being located at the 3' end of the 3' region and the second segment being located in the vicinity of the 5' region and wherein the 3' end of the second polynucleotide is reversibly blocked,
wherein the 3' region of the first single stranded polynucleotide is complementary to at least a portion of the 5' region of the second polynucleotide.

The expression "kit", as used herein, refers to a combination of two or more elements or components including other types of biochemical reagents, containers, packages such as packaging intended for commercial sale, electronic hardware components, etc.

Suitable kits include various reagents for use in accordance with the present invention in suitable containers and packaging materials, including tubes, vials, and shrink-wrapped and blow-molded packages. Additionally, the kits of the invention can contain instructions for the simultaneous, sequential or separate use of the different components which are in the kit. Said instructions can be in the form of printed material or in the form of an electronic support capable of storing instructions such that they can be read by a subject, such as electronic storage media (magnetic disks, tapes and the like), optical media (CD-ROM, DVD) and the like. Additionally or alternatively, the media can contain Internet addresses that provide said instructions.

In a preferred embodiment of the kit of the invention the second polynucleotide is provided as a library of polynucleotides, wherein each member is distinguishable from the others by a combinatorial sequence located within the 5' region of the second polynucleotide and upstream with respect to the region showing sequence complementarity with the first single stranded polynucleotide. In a more preferred embodiment the combinatorial sequence contains one or more modified cytosines which are resistant to treatment with the reagent which allows conversion of unmethylated cytosines to a base that is detectably dissimilar to cytosine in terms of hybridization properties.

In another embodiment the first single stranded polynucleotide and/or the second polynucleotide also contain modified cytosines.

In another embodiment the 5' region of the second polynucleotide contains a sequence which, when converted into a double stranded region, creates a target site for a restriction endonuclease.

Optionally, the kit may comprise one or more additional components.

In another embodiment the kit further comprises one or more components selected from the group consisting of:
(i) a DNA polymerase,
(ii) one or more nucleotides selected from A, G, C and T,
(iii) one or more modified cytosines which are resistant to treatment with the reagent which allows conversion of non-methylated cytosines to a base that is detectably dissimilar to cytosine in terms of hybridization properties,
(iv) a reagent capable of removing the blocking group from the 3' end of the second polynucleotide,
(v) a reagent which allows conversion of non-methylated cytosines to a base that is detectably dissimilar to cytosine in terms of hybridization properties and
(vi) a restriction endonuclease specific for the target site formed by the sequence within the 5' end of the second polynucleotide.

The expression "DNA polymerase", as used herein, refers to an enzyme that synthesizes a DNA strand de novo using a nucleic acid strand as a template and adding free nucleotides only to the 3'-hydroxil end of the newly forming strand. This results in elongation of the new strand in a 5'-3' direction. The DNA polymerase may be a naturally occurring DNA polymerase or a variant of natural enzyme having the above-mentioned activity.

The nucleotides provided in the kit may be modified nucleotides. Examples of modified nucleotides are modified cytosines such as methyl cytosine and hydroxymethylcytosine.

The expression "a reagent capable of removing the blocking group from the 3' end of the second polynucleotide", as used herein, refers to a reagent that unblocks the 3' end of the second polynucleotide. Said reagent depends on the specific blocking group used. Suitable reagents have been disclosed above (for example an acid, a phosphine, etc).

A restriction endonuclease specific for a target site is a restriction endonuclease capable of specifically recognizing and cleaving at or near a target sequence.

In a preferred embodiment the one or more modified cytosines are selected from the group consisting of methyl cytosine, hydroxymethylcytosine and a combination thereof.

The invention also provides kits comprising the library of Y-adapters of the method of the invention and further components.

In another aspect, the invention relates to a kit comprising:
(i) a library of Y-adapters, wherein each Y-adapter comprises a first DNA strand and a second DNA strand, wherein the 3' region of the first DNA strand and the 5' region of the second DNA strand form a double stranded region by sequence complementarity, wherein the 3' region of the second DNA strand forms a hairpin loop by hybridization between a first and a second segment within said 3' region, the first segment being located at the 3' end of the 3' region and the second segment being located in the vicinity of the region of the second DNA strand which forms a double stranded region with the 3' region of the first DNA strand and wherein each member of the library is distinguishable from the others by a combinatorial sequence located within the double stranded region formed between the 3' region of the first DNA strand and the 5' region of the second DNA strand and
(ii) one or more components selected from the group consisting of:
a) a DNA polymerase,
b) one or more nucleotides selected from A, G, C and T,
c) one or more modified cytosines which are resistant to treatment with the reagent which allows conversion of unmethylated cytosines to a base that is detectably dissimilar to cytosine in terms of hybridization properties,
d) a reagent capable of removing the blocking group from the 3' end of the second polynucleotide,
e) a reagent which allows conversion of unmethylated cytosines to a base that is detectably dissimilar to cytosine in terms of hybridization properties and
f) a restriction endonuclease specific for the target site formed by the sequence within the 5' end of the second polynucleotide.

All the particular embodiments disclosed previously for the library of Y-adapters and for the additional components of the kits for obtaining the Y-adapters are applicable to the kits comprising the library of Y-adapters of the method of the invention.

Other terms and expressions have also been defined previously.

Libraries of Double Stranded DNA Adapters Containing a Combinatorial Sequence and Methods for Obtaining Thereof The invention also provides a method for synthesizing any library of double stranded DNA adapters having a combinatorial sequence ("barcode sequences" or "combinatorial barcodes") that may be used in the method of the invention or in any other methodology that needs combinatorial barcodes.

In order to synthesize an adapter a precursor can be used consisting on two partially complementary oligonucleotides one of which bears a combinatorial region. This combinatorial region is single stranded DNA in the precursor form. After incubating this precursor form with the adequate enzymes, the incomplete oligonucleotide is completed and the combinatorial region becomes double stranded DNA.

In an aspect, the invention relates to a method for obtaining a library of double stranded DNA adapters, wherein each adapter comprises a first DNA strand and a second DNA strand and wherein each adapter is distinguishable from the others by a combinatorial sequence located within the double stranded region formed between the 3' region of the first DNA strand and the 5' region of the second DNA strand, said method comprising the steps of
- (i) providing a population of single stranded DNA molecules comprising a constant region and a combinatorial region, wherein said single stranded DNA molecules are distinguishable from the others by the sequence in the combinatorial region, wherein the constant region is located 3' with respect to the combinatorial region and wherein the 3' end is reversibly blocked and
- (ii) generating a double stranded DNA by using the single stranded DNA molecule of step (i) as a template and using an elongation primer which completely or partially hybridizes with the constant region of the single stranded DNA molecule, thereby replicating the combinatorial region onto the newly generated strand, thereby creating a double stranded combinatorial sequence.

The expression "constant region", as used herein, refers to a region in a single stranded DNA molecule wherein the sequence is the same for each member of the population of single stranded DNA molecules.

The expression "reversibly blocked", as used in the context of this aspect of the invention, refers without limitation to a reversible modification with a reversible blocking group that prevents the polynucleotide from priming for synthesis. Since said modification is reversible, the blocking group may be removed in further steps. Exemplary reversible blocking groups have been disclosed in the context of the "libraries of Y-adapters of the invention, methods and kits for synthesizing thereof".

The expression "reversibly blocked" also includes a linker that links the 5' end of the first DNA strand and the 3' end of the second DNA strand and that can be removed.

The expression "reversibly blocked" also encompasses the immobilization in a support of the single stranded DNA molecule by binding its 3' end to said support. Since the blocking is reversible, said link between the 3' end of the single stranded DNA molecule and the support may be broken in further steps.

The expression "completely or partially hybridizes with the constant region of the single stranded DNA molecule", as used herein, means that the totality or part of the elongation primer binds non-covalently to form a stable double-stranded polynucleotide with the constant region of the single stranded DNA molecule. The expressions "hybridization" and "hybridization conditions" have been defined in the context of the first method of the invention.

The elongation primer hybridizes completely with the constant region of the single stranded DNA molecule when 100% of the primer hybridizes with said region. The elongation primer hybridizes partially with the constant region of the single stranded DNA molecule, when less than 100% of the primer hybridizes with said region. Preferably, at least 0.1% of the elongation primer, at least 0.5%, at least 1%, at least 2%, at least 5%, at least 10%, at least 20%, at least 30%, at least 40%, at least 50%, at least 60%, at least 70%, at least 80%, at least 90%, at least 95% do not hybridize with the constant region of the single stranded DNA molecule.

The expression "combinatorial region", as used herein, refers to a variable region in a single stranded DNA molecule wherein the sequence is different for each member of the population of single stranded DNA molecules. The term combinatorial sequence has been defined previously.

The expression "replicating the combinatorial region onto the newly generated strand", as used herein, means that the newly generated strand contains the complementary and antiparallel sequence of the combinatorial region of the single stranded DNA molecule.

In a preferred embodiment the method further comprises removing the blocking group from the 3' end of the single stranded DNA molecules.

In another embodiment the elongation primer comprises an overhanging 5' region which does not hybridize with the constant region of the single stranded DNA molecules.

In another embodiment the constant region of the single stranded DNA molecules comprises an overhanging 3' region which does not hybridize with the elongation primer.

In another embodiment the constant region of the single stranded DNA molecules forms a hairpin loop by hybridization between a first and a second segment within said constant region.

The combinatorial sequence may be generated separately and then added to another adapter in order to generate combinatorial adapters. Therefore, the adapters of the library can be used as modules attachable to other incomplete adapters to obtain higher complexity adapters. For example, a combinatorial adapter of the library formed by two complementary strands can be ligated to a non-combinatorial Y-adapter to obtain a collection of Y-adapters with the combinatorial region.

In another embodiment the method further comprises ligating the adapters of the library to a second DNA molecule, said second DNA molecule having a double stranded region, the ends of which are compatible with the ends of the adapter molecules. Preferably, said second DNA molecule comprises overhanging regions in the 5' region of the first strand and/or in the 3' region of the second strand which do not hybridize to each other. In a more preferred embodiment the 3' overhanging region in the second strand forms a hairpin loop by hybridization between a first and a second segment within said region.

In another embodiment each single stranded DNA molecule of step (i) is provided immobilized in a support. In a more preferred embodiment said immobilization is carried out by binding the 5' end of the single stranded DNA molecule to said support, preferably by covalent binding. In another embodiment said immobilization is carried out by binding the 3' end of the single stranded DNA molecule to said support, preferably by covalent binding. In another preferred embodiment if the constant region of the single stranded DNA molecule forms a hairpin loop by hybridization between a first and a second segment within said constant region, said immobilization is carried out by binding a nucleotide of the hairpin loop of the single stranded DNA molecule to said support, preferably by covalent binding.

In another embodiment, the first DNA strand and the second DNA strand are joined by a linker between the 5' end of the first DNA strand and the 3' end of the second DNA strand and said linker is immobilized in a support. The binding of the linker to the support facilitates the elongation step. The binding between the linker and the support may be broken after the synthesis of the adapter has been finished in order to release the adapter. The adapter linked to the support by the linker may also be used for ligating molecules.

The invention also relates to the libraries of double stranded DNA adapter molecules obtained by said methods.

In another aspect, the invention relates to a library of double stranded DNA adapter molecules, wherein each DNA adapter molecule comprises a constant region and a variable region, wherein each double stranded DNA adapter comprises a first DNA strand and a second DNA strand and wherein each adapter is distinguishable from the others by a combinatorial sequence in the variable region located within the double stranded region formed between the 3' region of the first DNA strand and the 5' region of the second DNA strand.

In a preferred embodiment the 3' end of at least one of the strands is reversibly blocked.

In another embodiment one or both strands comprises an overhanging region which does not hybridize with the opposite strand. Preferably the constant region of one of the strands forms a hairpin loop by hybridization between a first and a second segment within said constant region.

FIG. 16 shows different embodiments of said aspect of the invention wherein Y-adapters comprising a hairpin according to the third method of the invention, Y-adapters according to the fourth, sixth and seventh method of the invention, hemiadapters and plain adapters are obtained.

While the foregoing invention has been described in some detail for purposes of clarity and understanding, it will be appreciated by one skilled in the art from a reading of this disclosure that various changes in form and detail can be made without departing from the true scope of the invention and appended claims.

The invention is described below by means of the following examples which must be considered as merely illustrative and in no case limiting to the scope of the present invention.

EXAMPLES

Example 1: A Protocol for the Method in which the Two Original Strands are Physically Paired and Only Desired Intermediate Products are Selectively Filtered, Bisulfite Transformed, Amplified and Sequenced Adapters Preparation.

Hairpin adapters were prepared from 10 µM oligonucleotide c15_Hairp01-5'P (SEQ ID NO: 1). Double stranded adapters were prepared from 20 µM oligonucleotide c14_Hang04 5'P (SEQ ID NO: 2) and 20 µM oligonucleotide c14_BIO05noB (SEQ ID NO: 3). Adapters were hybridized by initial denaturation followed by progressive cooling, in a termocycler (95° 2'; 80° 2'; 65° 10'; 37° 10'; 25° 5'; 4°-').

Ligation Process.

4 pmol of dsDNA fragments (30 mer) were mixed to a final concentration of 0.2 µM, with 3 µM hairpin adapters and 3 µM double stranded adapters, in the presence of T4DNA ligase and T4 buffer in a final volume of 20 µL, for 15 minutes at 23° C. The reaction product was purified with G50 columns Ligation Product Capture.

Proper reaction products were captured by means of the biotinylated oligonucleotide complementary to the hairpin adapter: 3 µL of 20 µM c14_BIO04-5'B (SEQ ID NO: 4) were added to 10 µL of ligation reaction in the presence of SSC. The reaction tube was gently mixed and incubated in a termocycler (90° 2'; 65° 5'; 60° 5'; 55° 5'; 25°-'). 30 µL of M-270 beads were resuspended and prepared following manufacturer's instructions to a final volume of 90 µL of BW1×. M-270 beads were added to the capture reaction and incubated at round temperature for 15 minutes. The reaction was washed and ligation products were released from the M-270 beads. Beads were resuspended in SCC1× and incubated in a heating block 2 min at 95° C. Supernatant containing the ligation products of interest was recovered.

Bisulfite.

50 µL of the Ligation product capture were treated with Sodium Bisulfite according to standard procedures, or according to manufacturer's instructions. Final product was eluted in 30 µL of Elution Buffer.

Amplification.

1 µL of previous step product was amplified with primers c14_amp02F (SEQ ID NO: 5) and c14_amp02R (SEQ ID NO: 6), by using polymerases such as, Zymotag or TurboPfu. 1 µL of 20 µM of each primer was used for 30 µL of final volume reaction. 20 PCR cycles (95° 2'; 62° 30"; 72° 1') were performed. Products were purified with G50 column and assessed by PAGE electrophoresis.

Sequencing.

Resulting products from the previous step were processed according to Ion Torrent's protocol and visualized using Integrative Genomics Viewer.

Example 2: A Protocol for the Method in which Complementary Strands are Generated and Physically Paired to their Template, and the Whole Resulting Intermediate Product is Bisulfite Converted, Amplified and Sequenced Adapters Preparation.

Y-adapters were prepared from 20 µM oligonucleotide c15_YA4 (SEQ ID NO: 7) and 20 µM oligonucleotide c15_Hairp06 (SEQ ID NO: 8). Adapters were hybridized by initial denaturation followed by progressive cooling, in a termocycler (95° 2'; 80° 2'; 65° 10'; 37° 10'; 25° 5'; 4°-').

Ligation Process.

4 pmol of dsDNA fragments (30 mer) were mixed to a final concentration of 0.2 µM, with 2.5 µM Y-adapters, in the presence of T4DNA ligase and T4 buffer in a final volume of 20 µL, for 15 minutes at 23° C. The reaction product was purified with G50 columns.

Ligation Product Extension.

Ligation products were elongated by adding polymerase to the reaction under optimal buffer with dNTPs in a volume reaction of 30 µL. The reaction tube was gently mixed and incubated in a termocycler (25° 2'; 72° 10'; 4°-').

Bisulfite.

20 µL of the Ligation product capture were treated with Sodium Bisulfite according to standard procedures, or according to manufacturer's instructions. Final product was eluted in 20 µL of Elution Buffer.

Amplification.

1 µL of previous step product was amplified with primers c14_amp02F (SEQ ID NO: 5) and c14_amp02R (SEQ ID NO: 6), by using polymerases such as, Zymotag or TurboPfu. 1 µL of 20 µM of each primer was used for 30 µL of final volume reaction. 20 PCR cycles (95° 2'; 62° 30"; 72° 1') were performed. Products were purified with G50 column and assessed by PAGE electrophoresis.

Sequencing.

Resulting products from the previous step were processed according to Ion Torrent's protocol and visualized using Integrative Genomics Viewer.

TABLE I

Sequence of the oligonucleotides used in the Examples of the present invention

| Oligonucleotide | Sequence |
|---|---|
| c15_Hairp01-5'P | 5'-pho-GCTCCGATCGAGGGAGGTAGGATGGAGGAATGGCTCGATCGGAGCT-3' (SEQ ID NO: 1) |
| c14_Hang04_5'P | 5'-pho-GCAAGCAACGACGGTAACGGGCGGCTC-3' (SEQ ID NO: 2) |
| c14_BI005noB | 5'-CCGAGCCGCCCGTTACCGTCGTTGCTTGCT-3' (SEQ ID NO: 3) |
| c14_BI004-5'B | 5'-bio-AAAAAAAAACATTCCTCCATCCTACCTC-3' (SEQ ID NO: 4) |
| c14_amp02F | 5'-ACCCATTACCATCATTACTTAC-3' (SEQ ID NO: 5) |
| c14_amp02R | 5'-GAGTTGTTTGTTATTGTTGTTGTTTGT-3' (SEQ ID NO: 6) |
| c15_YA4 | 5'-GAGCCGCCCGTTACCGTCGTTGCTTGCTTCGGCTTCCTGAGTGT-3' (SEQ ID NO: 7) |
| c15_Hairp06 | 5'-pho-CACTCAGGAAGCCGAAGCGCTCCGATCGAGTGTTGTCTCGATCGGAGC-3' (SEQ ID NO: 8) | pho: phosphate; bio: biotin

Items of the Present Invention

The present invention provides the following items.

[1]. A method for generating a double stranded DNA library from a population of double stranded DNA molecules comprising the steps of
(i) contacting the population of double stranded DNA molecules with a first adapter molecule and a second adapter molecule,
  wherein said first adapter molecule is a double stranded DNA molecule having ends at one end which are compatible with the ends of the double stranded DNA
  wherein the second adapter molecule is a hairpin adapter which comprises a hairpin loop region and a double stranded region, wherein said double stranded region contains ends which are compatible with the ends of the double stranded DNA molecules, and
  wherein said contacting step is carried out under conditions adequate for the ligation of the first and/or second adapter molecules to the DNA molecules to yield a plurality of adapter-modified DNA molecules,
(ii) recovering from the population of adapter-modified DNA molecules obtained in step (i) those molecules which comprise the second adapter molecule at one end or at two ends of the adapter-modified DNA molecule,
(iii) synthesizing DNA strands using the adapter-modified DNA molecules obtained in step (ii) as template under conditions that allow the strand synthesis to take place and using a primer the sequence of which is complementary to at least a portion of the sequence of the first adapter molecule and
(iv) optionally, amplifying the double stranded DNA molecules obtained in step (iii) using primers the sequences of which are complementary to at least a portion of the first adapter region.

[2]. The method according to [1] wherein the recovering step (ii) is carried out using a polynucleotide comprising a sequence complementary to at least part of the sequence of the second adapter and a purification tag.

[3]. The method according to [1] or [2] wherein the DNA molecules obtained in step (ii) are recovered from the reaction mixture obtained after step (iii) or, as the case may be, after step (iv).

[4]. The method according to [3] wherein said recovery from the reaction mixture is carried out using a first member of a binding pair, wherein the first and/or second adapter are modified with a second member of said binding pair.

[5]. A method for generating a double stranded DNA library from a population of double stranded DNA molecules comprising the steps of
(i) contacting the population of double stranded DNA molecules with a first adapter molecule and a second adapter molecule,
  wherein said first adapter molecule is a double stranded DNA molecule having ends at one end which are compatible with the ends of the double stranded DNA
  wherein the second adapter molecule is a hairpin adapter which comprises a hairpin loop region and a double stranded region, wherein said double stranded region contains ends which are compatible with the ends of the double stranded DNA molecules,
  wherein the first adapter molecule or the second adapter molecule or both are provided immobilized in a support, wherein said immobilization is carried out by binding the end of one of the strands of the first adapter molecule or a nucleotide of the hairpin loop of the second adapter molecule to said support, and
  wherein said contacting step is carried out under conditions adequate for the ligation of the first and/or second adapter molecules to the DNA molecules to yield a plurality of adapter-modified DNA molecules,
(ii) synthesizing DNA strands using the adapter-modified DNA molecules obtained in step (i) as template and using a primer the sequence of which is complementary to at least a portion of the sequence of the first adapter molecule and
(iii) optionally, amplifying the double stranded DNA molecules obtained in step (ii) using primers the sequences of which are complementary to at least a portion of the first adapter region.

[6]. The method according to [1] to [5] wherein the double stranded DNA molecules used in step (i) are fragments of genomic DNA.

[7]. The method according to [1] to [6] wherein the double stranded DNA molecules used in step (i) are end-repaired prior to said step (i).

[8]. The method according to [7] further comprising a step of dA-tailing the DNA molecules after the end-repairing step.

[9]. The method according to [1] to [8] wherein the first and/or second adapter molecules are provided, respectively, as a first and second library of adapter molecules, wherein each member in the library is distinguishable from the others by a combinatorial sequence within the adapter sequence.

[10]. The method according to [1] to [9] wherein the population of adapter-modified DNA molecules is treated prior to step (iii) if the library has been obtained by a method according to [1] or prior to step (ii) if the library has been obtained by a method according to [5] with a reagent which allows conversion of unmethylated cytosines to a base that is detectably dissimilar to cytosine in terms of hybridization properties and wherein the primers used in steps (iii) and (iv) of [1] or, as the case may be, in steps (ii) and (iii) of [5] are specific for the first adapter molecule after having been treated with said reagent.

[11]. The method according to [10] wherein the combinatorial sequence within the adapter sequence contains modified cytosines which are resistant to treatment with the reagent which allows conversion of unmethylated cytosines to a base that is detectably dissimilar to cytosine in terms of hybridization properties.

[12]. The method according to [1] to [11] wherein the DNA molecules obtained in step (iii) or, as the case may be, in step (iv) if the library has been obtained by a method according to [1] or in step (ii) or, as the case may be, in step (iii) if the library has been obtained by a method according to [5] are recovered from the reaction mixture.

[13]. The method according to [12] wherein said recovery from the reaction mixture is carried out using a first member of a binding pair, wherein the primer used in step (iii) or, as the case may be, in step (iv) of [1] or in step (ii) or, as the case may be, in step (iii) of [5] is modified with a second member of said binding pair.

[14]. The method according to [1] to [13] wherein the population of double stranded DNA molecules is treated, prior to step (i) with adapter molecules, under conditions adequate for the ligation of the adapter molecules to the DNA molecules thereby introducing cohesive ends in said DNA molecules.

[15]. A method for determining the sequence of a population of double stranded DNA molecules comprising generating a library from said population of double stranded DNA molecules using a method according to [1] to [14] and sequencing the DNA molecules obtained in step (iii) or, as the case may be, in step (iv) if the library has been obtained by a method according to [1] or the DNA molecules obtained in step (i), or in step (ii) or, as the case may be, in step (iii) if the library has been obtained by a method according to [5]. [16]. A method for the identification of methylated cytosines in a population of double stranded DNA molecules comprising the steps of (i) generating a library from said population of double stranded DNA molecules using a method according to [1] to [14], wherein the population of adapter-modified DNA molecules is treated prior to step (iii) if the library has been obtained by a method according to [1] or prior to step (ii) if the library has been obtained by a method according to [5] with a reagent which allows conversion of unmethylated cytosines to a base that is detectably dissimilar to cytosine in terms of hybridization properties and wherein the primers used in steps (iii) and (iv) if the library has been obtained by a method according to [1] or in steps (ii) and (iii) if the library has been obtained by a method according to [5] are specific for the first adapter molecule after having been treated with said reagent and (ii) sequencing the DNA molecules obtained in step (ii) or in step (iii) or, as the case may be, in step (iv) if the library has been obtained by a method according to [1] or the DNA molecules obtained in step (i) or in step (ii) or, as the case may be, in step (iii) if the library has been obtained by a method according to [5] that have been treated prior to step (iii) if the library has been obtained by a method according to [1] or prior to step (ii) if the library has been obtained by a method according to [5] with a reagent which allows conversion of unmethylated cytosines to a base that is detectably dissimilar to cytosine in terms of hybridization properties, wherein the presence of methylated cytosine at a given position is determined if a cytosine appears in one of the strands and a guanine appears in the corresponding position in the opposite strand or wherein the presence of an unmethylated cytosine at a given position is determined if a uracil or thymine appears in one of the strands and a guanine appears in the corresponding position in the opposite strand.

[17]. A method for generating a double stranded DNA library from a population of double stranded DNA molecules comprising the steps of (i) contacting the population of double stranded DNA molecules with a DNA Y-adapter, said adapter comprising a first DNA strand and a second DNA strand, wherein the 3' region of the first DNA strand and the 5' region of the second DNA strand form a double stranded region by sequence complementarity, wherein the ends of said double stranded region formed by the 3' region of the first DNA strand and the 5' region of the second DNA strand of the Y-adapter are compatible with the ends of the double stranded DNA molecules, wherein the 3' region of the second DNA strand of the Y-adapter forms a hairpin loop by hybridization between a first and a second segment within said 3' region, the first segment being located at the 3' end of the 3' region and the second segment being located in the vicinity of the 5' region of the second DNA strand, wherein said contacting is carried out under conditions adequate for the ligation of the Y-adapter to both ends of the double stranded DNA molecules, thereby obtaining a plurality of Y-adapter-containing DNA molecules, (ii) converting each of the strands of the DNA molecules obtained in step (i) into a double-stranded DNA molecule by polymerase elongation from the 3' end of the second DNA strand in the Y-adapter molecule using each of the strands of the DNA molecules obtained in step (i) as template and (iii) optionally, amplifying the double stranded DNA molecules obtained in step (ii) using at least a primer the sequence of which is complementary to at least a portion of the double stranded DNA molecules obtained in step (ii).

[18]. The method according to [17] wherein the Y-adapter-containing DNA molecules obtained in step (i) are treated prior to step (ii) under conditions adequate for separation of the strands of the Y-adapter-containing DNA molecules.

[19]. A method for generating a double stranded DNA library from a population of double stranded DNA molecules comprising the steps of
  (i) contacting the population of double stranded DNA molecules with a DNA Y-adapter, said adapter comprising a first DNA strand and a second DNA strand, wherein the 3' region of the first DNA strand and the 5' region of the second DNA strand form a double stranded region by sequence complementarity and wherein the ends of said double stranded region are compatible with the ends of the double stranded DNA molecules,
    wherein said contacting is carried out under conditions adequate for the ligation of the Y-adapter to both ends of the double stranded DNA molecules, thereby obtaining a plurality of Y-adapter-containing DNA molecules,
  (ii) contacting each strand of said Y-adapter-containing DNA molecules with an elongation primer which comprises a 3' region which is complementary to the second DNA strand of the Y-adapter molecule under conditions adequate for the hybridization of the elongation primer to the second strand of the Y-adapter and which, after hybridization with the second DNA strand of the Y-adapter molecule creates overhanging ends,
  (iii) contacting the molecules generated in step (ii) with a hairpin adapter, said hairpin adapter comprising a hairpin loop region and overhanging ends which are compatible with the overhanging ends in the molecules generated in step (ii) under conditions adequate for the ligation of the hairpin adapter to the molecules generated in step (ii),
  (iv) converting each of the strands of the DNA molecules obtained in step (iii) into a double-stranded DNA molecule by polymerase elongation from the elongation primer used in step (ii) and
  (v) optionally, amplifying the double stranded DNA molecules obtained in step (iv) using at least a primer the sequence of which is complementary to at least a portion of the double stranded DNA molecules obtained in step (iv)
    wherein the step of ligation to the hairpin adapter (iii) and the elongation step (iv) can be carried out in any order or simultaneously.

[20]. The method according to [19] wherein the Y-adapter-containing DNA molecules obtained in step (i) or in step (iii) are placed under conditions adequate for separating the strands of said Y-adapter-containing DNA molecules.

[21]. The method according to [19] or [20] wherein step (ii) of contacting each strand of said Y-adapter-containing DNA molecules with an elongation primer and step (iii) of contacting the molecules generated in step (ii) with a hairpin adapter, are carried out in a single step by providing the hairpin adapter and the elongation primer as a complex.

[22]. The method according to [17] to [21] wherein the double stranded DNA molecules used in step (i) are fragments of genomic DNA.

[23]. The method according to [17] to [22] wherein the double stranded DNA molecules used in step (i) are end-repaired prior to said step (i).

[24]. The method according to [23] further comprising a step of dA-tailing the DNA molecules after the end-repairing step.

[25]. The method according to [17] to [24] wherein the Y-adapter is provided as a library of adapters wherein each member of the library is distinguishable from the others by a combinatorial sequence located within the double stranded region formed by the 3' region of the first DNA strand and the 5' region of the second DNA strand of the adapter.

[26]. The method according to [25] wherein the combinatorial sequence contains modified cytosines which are resistant to treatment with a reagent which allows conversion of unmethylated cytosines to a base that is detectably dissimilar to cytosine in terms of hybridization properties.

[27]. The method according to [17] to [26] wherein the adapter-containing DNA molecules are treated prior to step (iii) if the library has been obtained by a method according to [17] or prior to step (v) if the library has been obtained by a method according to [19] with a reagent which allows conversion of unmethylated cytosines to a base that is detectably dissimilar to cytosine in terms of hybridization properties and wherein the primers used in step (iii) of [17] or, as the case may be, in step (v) of [19] are complementary to at least a portion of the sequence resulting from the treatment with said reagent of the double stranded DNA molecules obtained in step (ii) of [17] or, as the case may be, in step (iv) of [19].

[28]. The method according to [17] to [27] wherein the hairpin adapter and/or the Y-adapter is provided immobilized in a support, wherein said immobilization is carried out by binding a nucleotide of the hairpin loop of the hairpin adapter and/or a nucleotide of the hairpin loop of the second DNA strand of the Y-adapter and/or the 5' end of the first DNA strand of the Y-adapter to said support.

[29]. A method for determining the sequence of a population of double stranded DNA molecules comprising generating a library from said population of double stranded DNA molecules using a method according to [17] to [28] and sequencing the DNA molecules obtained in step (ii) or, as the case may be, in step (iii) if the library has been obtained by a method according to [17] or the DNA molecules obtained in step (iv) or, as the case may be, in step (v) if the library has been obtained by a method according to [19].

[30]. A method for the identification of methylated cytosines in a population of double stranded DNA molecules comprising the steps of
  (i) generating a library from said population of double stranded DNA molecules using a method according to [17] to [28], wherein the population of adapter-modified DNA molecules is treated prior to step (iii) if the library has been obtained by a method according to [17] or prior to step (v) if the library has been obtained by a method according to [19] with a reagent which allows conversion of unmethylated cytosines to a base that is detectably dissimilar to cytosine in terms of hybridization properties and wherein the primers used in step (iii) if the library has been obtained by a method according to [17] or in step (v) if the library has been obtained by a method according to [19] are specific for the sequence of the double stranded DNA molecules obtained in step (ii) of [17] or in step (iv) of [19] after having been treated with said reagent and
  (ii) sequencing the DNA molecules obtained in step (ii) or, as the case may be, in step (iii) if the library has been obtained by a method according to [17] or the DNA molecules obtained in step (iv) or, as the case may be, in step (v) if the library has been obtained by a method according to [19] that have been treated prior to step (iii) if the library has been obtained by a method according to [17] or prior to step (v) if the library has been obtained by a method according to [19] with a reagent which allows conversion of unmethylated cytosines to a base that is detectably dissimilar to cytosine in terms of hybridization properties, wherein the presence of methylated cytosine at a given position is determined if a cytosine appears in one of the strands and a guanine appears in the corresponding position in the opposite strand or wherein the presence of an unmethylated cytosine at a given position is determined if an uracil or thymine appears in one of the strands and a guanine appears in the corresponding position in the opposite strand.

[31]. A method for generating a double stranded DNA library from a population of double stranded DNA molecules comprising the steps of (i) fragmenting the population of double stranded DNA molecules under conditions adequate for generating a population of fragments of the double stranded DNA molecules with overhanging ends wherein each end of each fragment is bound to an hemiadapter molecule, said hemiadapter molecule comprising a first DNA strand and, optionally, a second DNA strand, wherein the second strand forms a double stranded region with the first strand through complementarity with a central region of the first strand and wherein the hemiadapter molecules are bound to the fragments of the double stranded DNA molecules between the 3' end of the first strand of the hemiadapter and the overhanging ends of the fragments of the double stranded DNA molecules, (ii) adding an alternative second strand or replacing the second DNA strand of the hemiadapter molecule with an alternative second strand, wherein the 5' region of said alternative second strand is complementary to the 3' region of the first strand of the hemiadapter molecule, said alternative second strand containing a region which is not complementary to the first strand of the hemiadapter molecule, thereby generating a plurality of Y-adapter-containing DNA molecules, (iii) optionally, filling gaps existing between the 5' end of the alternative second strand of the Y-adapter and the 3' end of each DNA fragment, (iv) contacting each strand of said Y-adapter-containing DNA molecules with an elongation primer which comprises a 3' region which is complementary to the alternative second DNA strand of the Y-adapter molecule and a 5' region which does not hybridize with the alternative second DNA strand of the Y-adapter, under conditions adequate for the hybridization of the elongation primer to the alternative second strand of the Y-adapter, (v) contacting the molecules generated in step (iv) with a hairpin adapter, said hairpin adapter comprising a hairpin loop region and ends which are compatible with the ends in the molecules generated in step (iv) under conditions adequate for the ligation of the hairpin adapter to the molecules generated in step (iv), (vi) converting each of the strands of the DNA molecules obtained in step (v) into a double-stranded DNA molecule by polymerase elongation from the elongation primer used in step (iv) and (vii) optionally, amplifying the double stranded DNA molecules obtained in step (vi) using at least a primer the sequence of which is complementary to at least a portion of the double stranded DNA molecules obtained in step (vi)

wherein the step of ligation to the hairpin adapter (v) and the elongation step (vi) can be carried out in any order or simultaneously.

[32]. The method according to [31] wherein the fragmenting step (i) is carried out by a method which comprises contacting the population of double stranded DNA molecules with a transposase dimer loaded with double stranded adapter molecules, wherein the adapter molecules comprise a double stranded region comprising a Tn5 inverted repeat and a 5' overhang of one of the strands, wherein the cytosine nucleotides in the double stranded region which does not form part of the Tn5 inverted repeat and in the single stranded region are optionally methylated and wherein the contacting is carried out under conditions adequate for fragmentation of the DNA and for the attachment of the hemiadapter molecules to both ends of each DNA fragment.

[33]. The method according to [31] or [32] wherein the Y-adapter-containing DNA molecules obtained in step (ii) or, as the case may be, in step (iii) or the hairpin adapter-containing DNA molecules obtained in step (v) or, as the case may be, in step (vi) are placed under conditions adequate for separating the strands of said Y-adapter-containing DNA molecules.

[34]. The method according to [31] to [33] wherein step (iv) of contacting each strand of said Y-adapter-containing DNA molecules with an elongation primer and step (v) of contacting the molecules generated in step (iv) with a hairpin adapter, are carried out in a single step by providing the hairpin adapter and the elongation primer as a complex.

[35]. The method according to [31] to [33] wherein step (ii) of adding an alternative second strand or replacing the second DNA strand of the hemiadapter molecule with an alternative second strand, step (iv) of contacting each strand of said Y-adapter-containing DNA molecules with an elongation primer and step (v) of contacting the molecules generated in step (iv) with a hairpin adapter, are carried out in a single step by providing the alternative second strand, the hairpin adapter and the elongation primer as a complex.

[36]. The method according to [35] wherein steps (ii) to (vi) are carried out simultaneously.

[37]. The method according to [31] to [36] wherein the hemiadapter used in step (i) is provided as a library of hemiadapters, each member of the library being distinguishable from the others by a combinatorial sequence in the 3' region of the first strand of the hemiadapter.

[38]. The method according to [37] wherein the second strand of the hemiadapter or the alternative second strand used in step (ii) does not show any substantial overlap with said combinatorial sequence.

[39]. The method according to [37] or [38] wherein the combinatorial sequence contains one or more modified cytosines which are resistant to treatment with a reagent which allows conversion of unmethylated cytosines to a base that is detectably dissimilar to cytosine in terms of hybridization properties.

[40]. The method according to [31] to [39] wherein the adapter-containing DNA molecules are treated prior to step (vii) with a reagent which allows conversion of unmethylated cytosines to a base that is detectably dissimilar to cytosine in terms of hybridization properties and wherein the primers used in step (vii) are complementary to at least a portion of the sequence resulting from the treatment with said reagent of the double stranded DNA molecules obtained in step (vi).

[41]. The method according to [31] to [40] wherein the molecules obtained in step (vi) or, as the case may be, in step (vii) are recovered from the reaction mixture.

[42]. A method for determining the sequence of a population of double stranded DNA molecules comprising generating a library from said population of double stranded DNA molecules using a method according to [31] to [41] and sequencing the DNA molecules obtained in step (vi) or, as the case may be, in step (vii).

[43]. A method for the identification of methylated cytosines in a population of double stranded DNA molecules comprising the steps of
  (i) generating a library from said population of double stranded DNA molecules using a method according to [31] to [41], wherein the population of adapter-modified DNA molecules is treated prior to step (vii) with a reagent which allows conversion of unmethylated cytosines to a base that is detectably dissimilar to cytosine in terms of hybridization properties and wherein the primers used in step (vii) are specific for the sequence of the double stranded DNA molecules obtained in step (vi) after having been treated with said reagent and
  (ii) sequencing the DNA molecules obtained in step (vi) or, as the case may be, in step (vii) that have been treated prior to step (vii) with a reagent which allows conversion of unmethylated cytosines to a base that is detectably dissimilar to cytosine in terms of hybridization properties,
  wherein the presence of methylated cytosine at a given position is determined if a cytosine appears in one of the strands and a guanine appears in the corresponding position in the opposite strand or wherein the presence of an unmethylated cytosine at a given position is determined if an uracil or thymine appears in one of the strands and a guanine appears in the corresponding position in the opposite strand.

[44]. A method for generating a double stranded DNA library from a population of double stranded DNA molecules comprising the steps of
  (i) contacting the population of double stranded DNA molecules with a population of DNA adapters, each adapter comprising a first DNA strand and a second DNA strand,
    wherein the 3' region of the first DNA strand and the 5' region of the second DNA strand form a double stranded region by sequence complementarity and wherein the ends of said double stranded region are compatible with the ends of the double stranded DNA molecules,
    wherein each adapter of the population is distinguishable from the others by a combinatorial sequence located within the double stranded region formed between the 3' region of the first DNA strand and the 5' region of the second DNA strand,
    wherein said contacting is carried out under conditions adequate for the ligation of an adapter to each end of the double stranded DNA molecules, thereby obtaining a plurality of adapter-containing DNA molecules,
  (ii) optionally, treating the adapter-containing DNA molecules obtained in step (i) with a reagent which allows conversion of unmethylated cytosines to a base that is detectably dissimilar to cytosine in terms of hybridization properties, and
  (iii) optionally, amplifying the adapter-containing DNA molecules obtained in step (i) or, as the case may be, in step (ii) using at least a primer the sequence of which is complementary to at least a portion of the adapter-containing DNA molecules obtained in step (i) or in step (ii).

[45]. The method according to [44] wherein the 5' region of the first DNA strand and the 3' region of the second DNA strand are complementary.

[46]. The method according to [44] wherein the adapter is an Y-adapter wherein the 5' region of the first DNA strand and the 3' region of the second DNA strand are not complementary.

[47]. A method for generating a double stranded DNA library from a population of double stranded DNA molecules comprising the steps of
  (i) fragmenting the population of double stranded DNA molecules under conditions adequate for generating a population of fragments of the double stranded DNA molecules with overhanging ends wherein each end of each fragment is bound to an hemiadapter molecule, said hemiadapter molecule comprising a first DNA strand and, optionally, a second DNA strand, wherein each hemiadapter is distinguishable from the others by a combinatorial sequence located within the 3' region of the first DNA strand, wherein the second strand forms a double stranded region with the first strand through complementarity with a central region of the first strand and wherein the hemiadapter molecules are bound to the fragments of the double stranded DNA molecules between the 3' end of the first strand of the hemiadapter and the overhanging ends of the fragments of the double stranded DNA molecules,
  (ii) adding an alternative second strand or replacing the second DNA strand of the hemiadapter molecule with an alternative second strand, wherein the 5' region of said alternative second strand is complementary to the 3' region of the first strand of the hemiadapter molecule, said alternative second strand containing a region which is not complementary to the first strand of the hemiadapter molecule, thereby generating a plurality of Y-adapter-containing DNA molecules,
  (iii) optionally, filling gaps existing between the 5' end of the alternative second strand of the Y-adapter and the 3' end of each DNA fragment,
  (iv) optionally, treating the Y-adapter-containing DNA molecules obtained in step (iii) with a reagent which allows conversion of unmethylated cytosines to a base that is detectably dissimilar to cytosine in terms of hybridization properties, and
  (v) optionally, amplifying the Y-adapter-containing DNA molecules obtained in step (ii) or in step (iii) or, as the case may be, in step (iv) using at least a primer the sequence of which is complementary to at least a portion of the Y-adapter-containing DNA molecules obtained in step (ii) or in step (iii) or, as the case may be, in step (iv).

[48]. The method according to [47] wherein (i) is carried out by a method which comprises contacting the population of double stranded DNA molecules with a transposase dimer loaded with double stranded adapter molecules, wherein the adapter molecules comprise a double stranded region comprising a Tn5 inverted repeat and a 5' overhang of one of the strands, wherein the cytosine nucleotides in the double stranded region which does not form part of the Tn5 inverted repeat and in the single stranded region are optionally methylated and wherein the contacting is carried out under conditions adequate for fragmentation of the DNA and for the attachment of the hemiadapter molecules to both ends of each DNA fragment.

[49]. The method according to [47] or [48] wherein the second strand of the hemiadapter or the alternative second strand used in step (ii) does not show any substantial overlap with said combinatorial region.

[50]. The method according to [44] to [49] wherein the double stranded DNA molecules used in step (i) are fragments of genomic DNA.

[51]. The method according to [44] to [50] wherein the double stranded DNA molecules used in step (i) are end-repaired prior to said step (i).

[52]. The method according to [51] further comprising a step of dA-tailing the DNA molecules after the end-repairing step.

[53]. The method according to [44] to [52] wherein the population of double stranded DNA molecules is treated, prior to step (i) with adapter molecules, under conditions adequate for the ligation of the adapter molecules to the DNA molecules thereby introducing cohesive ends in said DNA molecules.

[54]. The method according to [44] to [53] wherein the combinatorial sequence within the adapter sequence contains one or more modified cytosines which are resistant to treatment with the reagent which allows conversion of unmethylated cytosines to a base that is detectably dissimilar to cytosine in terms of hybridization properties.

[55]. The method according to [44] to [54] wherein the DNA molecules obtained in step (i) or in step (ii) if the library has been obtained by a method according to [44] or the DNA molecules obtained in step (iii) or in step (iv) if the library has been obtained by a method according to [47], are recovered from the reaction mixture obtained after step (i), step (ii) or, as the case may be, after step (iii) of [44] or from the reaction mixture obtained after step (iii), step (iv) or, as the case may be, after step (v) of [47].

[56]. The method according to [55] wherein said recovery from the reaction mixture is carried out using a first member of a binding pair, wherein the adapter is modified with a second member of said binding pair.

[57]. The method according to [44] to [56] wherein the DNA molecules obtained in step (iii) if the library has been obtained by a method according to [44] or the DNA molecules obtained in step (v) if the library has been obtained by a method according to [47], are recovered from the reaction mixture.

[58]. The method according to [57] wherein said recovery from the reaction mixture is carried out using a first member of a binding pair, wherein the primers used in step (iii) of [44] or in step (v) of [47] are modified with a second member of said binding pair.

[59]. A method for determining the sequence of a population of double stranded DNA molecules comprising generating a library from said population of double stranded DNA molecules using a method according to [44] to [58] and sequencing the DNA molecules obtained in step (i) or in step (ii) or, as the case may be, in step (iii) if the library has been obtained by a method according to [44] or sequencing the DNA molecules obtained in step (ii) or in step (iii) or in step (iv) or, as the case may be, in step (v) if the library has been obtained by a method according to [47].

[60]. A method for the identification of methylated cytosines in a population of double stranded DNA molecules comprising the steps of (i) generating a library from said population of double stranded DNA molecules using a method according to [44] to [58] wherein the population of adapter-modified DNA molecules is treated prior to step (iii) if the library has been obtained by a method according to [44] or prior to step (v) if the library has been obtained by a method according to [47] with a reagent which allows conversion of unmethylated cytosines to a base that is detectably dissimilar to cytosine in terms of hybridization properties and wherein the primers used in step (iii) if the library has been obtained by a method according to [44] or in step (v) if the library has been obtained by a method according to [47] are specific for the sequence of the DNA molecules obtained in step (ii) of [44] or in step (iv) of [47], and (ii) sequencing the DNA molecules obtained in step (ii) or, as the case may be, in step (iii) if the library has been obtained by a method according to [44] or sequencing the DNA molecules obtained in step (iv) or, as the case may be, in step (v) if the library has been obtained by a method according to [47], wherein the presence of methylated cytosine at a given position is determined if a cytosine appears in one of the strands and a guanine appears in the corresponding position in the opposite strand or wherein the presence of an unmethylated cytosine at a given position is determined if an uracil or thymine appears in one of the strands and a guanine appears in the corresponding position in the opposite strand.

[61]. A DNA library obtainable with a method according to [1] to [14], [17] to [28], [31] to [41] or [44] to [58].

[62]. A library of Y-adapters
wherein each Y-adapter comprises a first DNA strand and a second DNA strand, wherein the 3' region of the first DNA strand and the 5' region of the second DNA strand form a double stranded region by sequence complementarity,
wherein the 3' region of the second DNA strand forms a hairpin loop by hybridization between a first and a second segment within said 3' region, the first segment being located at the 3' end of the 3' region and the second segment being located in the vicinity of the region of the second DNA strand which forms a double stranded region with the 3' region of the first DNA strand and
wherein each member of the library is distinguishable from the others by a combinatorial sequence located within the double stranded region formed between the 3' region of the first DNA strand and the 5' region of the second DNA strand.

[63]. The library according to [62] wherein the combinatorial sequence contains one or more modified cytosines which are resistant to treatment with the reagent which allows conversion of unmethylated cytosines to a base that is detectably dissimilar to cytosine in terms of hybridization properties.

[64]. The library according to [62] or [63] wherein the 3' end of the second polynucleotide in each adapter is reversibly blocked.

[65]. The library according to [62] to [64] wherein the end segment of the double stranded region formed between the 3' region of the first DNA strand and the 5' region of the second DNA strand in each adapter contains a target site for a restriction endonuclease.

[66]. A method for producing a DNA Y-adapter comprising the steps of:
(i) contacting a first single stranded polynucleotide with a second single stranded polynucleotide wherein the 3' region of the first single stranded polynucleotide is complementary to at least a portion of the 5' region of the second polynucleotide,
  wherein the 3' region of the second single stranded polynucleotide forms a hairpin loop by hybridization of a first and a second segment within said 3' region, the first segment being located at the 3' end of the 3' region and the second segment being located in the vicinity of the 5' region of the second polynucleotide and wherein the 3' end of the second polynucleotide is reversibly blocked,
  said contacting being carried out under conditions adequate for the hybridization of the 3' region of the first single stranded polynucleotide and the complementary region within the 5' region of the second single stranded polynucleotide, thereby producing a duplex DNA molecule,
(ii) elongating the 3' end of the first polynucleotide so as to generate within said first single stranded polynucleotide a sequence which is complementary to the 5' region of the second polynucleotide and
(iii) optionally, unblocking the 3' end of the second polynucleotide.
[67]. The method according to [66] wherein the elongation carried out in step (ii) is carried out in the presence of modified cytosines which are resistant to treatment with the reagent which allows conversion of unmethylated cytosines to a base that is detectably dissimilar to cytosine in terms of hybridization properties.
[68]. The method according to [66] or [67] wherein the at least one position within the 3' end of the first polynucleotide is guanine and wherein the positions within the 5' region of the second polynucleotide which hybridize with said position or positions within the 3' end of the first polynucleotide are cytosine or methyl-cytosine.
[69]. The method according to [66] to [68] wherein the 5' end of the second single stranded polynucleotide comprises a sequence which, when the complementary strand is formed during elongation step (ii), is replicated onto the complementary strand forming a target site for a restriction endonuclease.
[70]. The method according to [66] to [69] wherein the second single stranded polynucleotide is provided as a library of polynucleotides, wherein each member of the library is distinguishable from the others by a combinatorial sequence located within the 5' region of said polynucleotide and wherein said combinatorial sequence is located upstream with respect to the region showing sequence complementarity with the first single stranded polynucleotide, thereby producing a library of DNA Y-adapter molecules.
[71]. The method according to [70] wherein the combinatorial sequence contains one or more cytosines which are resistant to treatment with the reagent which allows conversion of unmethylated cytosines to a base that is detectably dissimilar to cytosine in terms of hybridization properties.
[72]. The method according to [66] to [71] wherein the first single stranded polynucleotide and/or the second single stranded polynucleotide are provided immobilized in a support, wherein said immobilization is carried out by binding the 5' end of the first single stranded polynucleotide or a nucleotide of the hairpin loop of the second single stranded polynucleotide to said support.
[73]. A kit comprising
  (i) a first single stranded polynucleotide comprising a 5' region and a 3' region,
  (ii) a second polynucleotide comprising a 5' region and a 3' region, wherein the 3' region forms a hairpin loop by hybridization between a first and a second segment within said 3' region, the first segment being located at the 3' end of the 3' region and the second segment being located in the vicinity of the 5' region and wherein the 3' end of the second polynucleotide is reversibly blocked,
  wherein the 3' region of the first single stranded polynucleotide is complementary to at least a portion of the 5' region of the second polynucleotide.
[74]. The kit according to [73] wherein the second polynucleotide is provided as a library of polynucleotides, wherein each member is distinguishable from the others by a combinatorial sequence located within the 5' region of the second polynucleotide and upstream with respect to the region showing sequence complementarity with the first single stranded polynucleotide.
[75]. The kit according to [74] wherein the combinatorial sequence contains one or more modified cytosines which are resistant to treatment with the reagent which allows conversion of unmethylated cytosines to a base that is detectably dissimilar to cytosine in terms of hybridization properties.
[76]. The kit according to [73] to [75] wherein the 5' region of the second polynucleotide contains a sequence which, when converted into a double stranded region, creates a target site for a restriction endonuclease.
[77]. The kit according to [73] to [76] further comprising one or more components selected from the group consisting of:
  (i) a DNA polymerase,
  (ii) one or more nucleotides selected from A, G, C and T,
  (iii) one or more modified cytosines which are resistant to treatment with the reagent which allows conversion of unmethylated cytosines to a base that is detectably dissimilar to cytosine in terms of hybridization properties,
  (iv) a reagent capable of removing the blocking group from the 3' end of the second polynucleotide,
  (v) a reagent which allows conversion of unmethylated cytosines to a base that is detectably dissimilar to cytosine in terms of hybridization properties and
  (vi) a restriction endonuclease specific for the target site formed by the sequence within the 5' end of the second polynucleotide.
[78]. A kit comprising:
(i) a library of Y-adapters according to [62] to [65]; and
(ii) one or more components selected from the group consisting of:
  i. a DNA polymerase,
  ii. one or more nucleotides selected from A, G, C and T,
  iii. one or more modified cytosines which are resistant to treatment with the reagent which allows conversion of unmethylated cytosines to a base that is detectably dissimilar to cytosine in terms of hybridization properties,
  iv. a reagent capable of removing the blocking group from the 3' end of the second polynucleotide,
  v. a reagent which allows conversion of unmethylated cytosines to a base that is detectably dissimilar to cytosine in terms of hybridization properties and
  vi. a restriction endonuclease specific for the target site formed by the sequence within the 5' end of the second polynucleotide.

[79]. The kit according to [77] or [78] wherein the one or more modified cytosines are selected from the group consisting of methyl cytosine, hydroxylmethylcytosine and a combination thereof.

[80]. A method for obtaining a library of double stranded DNA adapters, wherein each adapter comprises a first DNA strand and a second DNA strand and wherein each adapter is distinguishable from the others by a combinatorial sequence located within the double stranded region formed between the 3' region of the first DNA strand and the 5' region of the second DNA strand, said method comprising the steps of
  (i) providing a population of single stranded DNA molecules comprising a constant region and a combinatorial region, wherein said single stranded DNA molecules are distinguishable from the others by the sequence in the combinatorial region, wherein the constant region is located 3' with respect to the combinatorial region and wherein the 3' end is reversibly blocked and
  (ii) generating a double stranded DNA using the single stranded DNA molecule of step (i) as a template and using an elongation primer which completely or partially hybridizes with the constant region of the single stranded DNA molecule, thereby replicating the combinatorial region onto the newly generated strand, thereby creating a double stranded combinatorial sequence.

[81]. The method according to [80] further comprising removing the blocking group from the 3' end of the single stranded DNA molecules.

[82]. The method according to [80] or [81] wherein the elongation primer comprises an overhanging 5' region which does not hybridize with the constant region of the single stranded DNA molecules.

[83]. The method according to [80] to [82] wherein the constant region of the single stranded DNA molecules forms a hairpin loop by hybridization between a first and a second segment within said constant region.

[84]. The method according to [80] or [81] further comprising ligating the adapters of the library to a second DNA molecule, said second DNA molecule having a double stranded region, the ends of which are compatible with the ends of the adapter molecules.

[85]. The method according to [84] wherein the second DNA molecule comprises overhanging regions in the 5' region of the first strand and/or in the 3' of the second strand which do not hybridize to each other.

[86]. The method according to [85] wherein the 3' overhanging region in the second strand forms a hairpin loop by hybridization between a first and a second segment within said region.

[87]. The method according to [80] to [82] or [84] to [86] wherein each single stranded DNA molecule of step (i) is provided immobilized in a support, wherein said immobilization is carried out by binding the 5' end of the single stranded DNA molecule to said support.

[88]. The method according to [83] wherein each single stranded DNA molecule of step (i) is provided immobilized in a support, wherein said immobilization is carried out by binding a nucleotide of the hairpin loop of the single stranded DNA molecule to said support.

[89]. A library of double stranded DNA adapter molecules, wherein each DNA adapter molecule comprises a constant region and a variable region, wherein each double stranded DNA adapter comprises a first DNA strand and a second DNA strand and wherein each adapter is distinguishable from the others by a combinatorial sequence in the variable region located within the double stranded region formed between the 3' region of the first DNA strand and the 5' region of the second DNA strand.

[90]. The library according to [89] wherein the 3' end of at least one of the strands is reversibly blocked.

[91]. The library according to [89] or [90] wherein one or both strands comprise an overhanging region which does not hybridize with the opposite strand.

[92]. The library according to [91] wherein the constant region of one of the strands forms a hairpin loop by hybridization between a first and a second segment within said constant region.

The invention claimed is:

1. A library of DNA Y-adapters for use in a method for the identification of methylated cytosines in a population of double-stranded DNA molecules, each DNA Y-adapter comprising a first DNA strand and a second DNA strand, wherein:
   (1) a 3' region of the first DNA strand and a 5' region of the second DNA strand form a double-stranded region by sequence complementarity, and
   (2) wherein the ends of said double-stranded region formed by the 3' region of the first DNA strand and the 5' region of the second DNA strand of each DNA Y-adapter are compatible with the ends of a double-stranded DNA molecule, and
   (3) wherein the double-stranded region of each DNA Y-adapter comprises one or more barcode sequence(s), wherein each DNA Y-adapter comprises at least one barcode sequence in a single-stranded region of the DNA Y-adapter, a barcode being an identifier unique to the individual DNA Y-adapter, and
   (4) wherein each of the DNA-Y adapters is distinguishable from the others by the one or more barcode sequence(s) located within the double-stranded region formed by the 3' region of the first DNA strand and the 5' region of the second DNA strand of the DNA Y-adapter.

2. The library of DNA Y-adapters according to claim 1, wherein each DNA Y-adapter has a restriction site in the 5' region of the first DNA strand of the DNA Y-adapter.

3. The library of DNA Y-adapters as defined in claim 1 wherein a combinatorial sequence contains one or more modified cytosines which are resistant to treatment with a reagent which allows conversion of non-methylated cytosines to a base that is detectably dissimilar to cytosine in terms of hybridization properties.

4. A kit comprising the library of DNA Y-adapters as defined in claim 1.

5. The kit according to claim 4, further comprising one or more components selected from the group consisting of:
   a) a DNA polymerase,
   b) one or more nucleotides selected from A, G, C and T,
   c) one or more modified cytosines which are resistant to treatment with a reagent which allows conversion of unmethylated cytosines to a base that is detectably dissimilar to cytosine in terms of hybridization properties,
   d) a reagent capable of removing a blocking group from the 3' end of a second polynucleotide,
   e) a reagent which allows conversion of unmethylated cytosines to a base that is detectably dissimilar to cytosine in terms of hybridization properties, and
   f) a restriction endonuclease specific for a target site formed by a sequence within the 5' end of the second polynucleotide.

6. A library of DNA Y-adapters for use in a method for the identification of methylated cytosines in a population of double-stranded DNA molecules, each DNA Y-adapter comprising a first DNA strand and a second DNA strand, wherein:
   (1) a 3' region of the first DNA strand and a 5' region of the second DNA strand form a double-stranded region by sequence complementarity, and
   (2) wherein the ends of said double-stranded region formed by the 3' region of the first DNA strand and the 5' region of the second DNA strand of each DNA Y-adapter are compatible with the ends of a double-stranded DNA molecule, and
   (3) wherein the double-stranded region of each DNA Y-adapter comprises one or more barcode sequence(s), wherein each DNA Y-adapter comprises at least one barcode sequence in the single-stranded region of the DNA Y-adapter and wherein the 3' region of the second DNA strand of each DNA Y-adapter forms a hairpin loop by hybridization between a first and a second segment within said 3' region, the first segment being located at the 3' end of the 3' region, and
   (4) wherein each of the DNA-Y adapters is distinguishable from the others by the one or more barcode sequence(s) located within the double-stranded region formed by the 3' region of the first DNA strand and the 5' region of the second DNA strand of the DNA Y-adapter.

7. A kit comprising the library of DNA Y-adapters as defined in claim 6.

8. The kit according to claim 7, further comprising one or more components selected from the group consisting of:
   a) a DNA polymerase,
   b) one or more nucleotides selected from A, G, C and T,
   c) one or more modified cytosines which are resistant to treatment with a reagent which allows conversion of unmethylated cytosines to a base that is detectably dissimilar to cytosine in terms of hybridization properties,
   d) a reagent capable of removing a blocking group from the 3' end of a second polynucleotide,
   e) a reagent which allows conversion of unmethylated cytosines to a base that is detectably dissimilar to cytosine in terms of hybridization properties, and
   f) a restriction endonuclease specific for a target site formed by a sequence within the 5' end of the second polynucleotide.

9. A kit comprising
   (i) a library of DNA Y-adapters, said adapters comprising a first DNA strand and a second DNA strand, wherein a 3' region of the first DNA strand and a 5' region of the second DNA strand form a double-stranded region by sequence complementarity and wherein the ends of said double-stranded region are compatible with the ends of double-stranded DNA molecules;
   (ii) a plurality of elongation primers, wherein each elongation primer comprises a 3' region which is complementary to the second DNA strand of the DNA Y-adapter molecule as defined in (i) and which, after hybridization with the second DNA strand of the DNA Y-adapter creates overhanging ends; and
   (iii) a plurality of hairpin adapters, wherein each hairpin adapter comprises a hairpin loop region and overhanging ends which are compatible with the overhanging ends formed after hybridization of the elongation primer as defined in (ii) to the second strand of the DNA Y-adapter as defined in (i),
wherein the elongation primers of (ii) and the hairpin adapters of (iii) optionally are provided as a complex.

* * * * *

SEQUENCE LISTING

```
<160> NUMBER OF SEQ ID NOS: 8

<210> SEQ ID NO 1
<211> LENGTH: 46
<212> TYPE: DNA
<213> ORGANISM: Artificial Sequence
<220> FEATURE:
<223> OTHER INFORMATION: c15_Hairp01-5'P oligonucleotide
<220> FEATURE:
<221> NAME/KEY: misc_feature
<222> LOCATION: (1)..(1)
<223> OTHER INFORMATION: /replace = "guanosine 5'-phosphate"

<400> SEQUENCE: 1
nctccgatcg agggaggtag gatggaggaa tggctcgatc ggagct               46

<210> SEQ ID NO 2
<211> LENGTH: 27
<212> TYPE: DNA
<213> ORGANISM: Artificial Sequence
<220> FEATURE:
<223> OTHER INFORMATION: c14_Hang04 5'P oligonucleotide
<220> FEATURE:
<221> NAME/KEY: misc_feature
<222> LOCATION: (1)..(1)
<223> OTHER INFORMATION: /replace = "guanosine 5'-phosphate"
```

```
<400> SEQUENCE: 2
ncaagcaacg acggtaacgg gcggctc                                          27

<210> SEQ ID NO 3
<211> LENGTH: 30
<212> TYPE: DNA
<213> ORGANISM: Artificial Sequence
<220> FEATURE:
<223> OTHER INFORMATION: c14_BIO05noB oligonucleotide

<400> SEQUENCE: 3
ccgagccgcc cgttaccgtc gttgcttgct                                       30

<210> SEQ ID NO 4
<211> LENGTH: 28
<212> TYPE: DNA
<213> ORGANISM: Artificial Sequence
<220> FEATURE:
<223> OTHER INFORMATION: c14_BIO04-5'B biotinylated oligonucleotide
<220> FEATURE:
<221> NAME/KEY: misc_binding
<222> LOCATION: (1)..(1)
<223> OTHER INFORMATION: 5' binding to biotin

<400> SEQUENCE: 4
aaaaaaaaac attcctccat cctacctc                                         28

<210> SEQ ID NO 5
<211> LENGTH: 22
<212> TYPE: DNA
<213> ORGANISM: Artificial Sequence
<220> FEATURE:
<223> OTHER INFORMATION: c14_amp02F oligonucleotide

<400> SEQUENCE: 5
acccattacc atcattactt ac                                               22

<210> SEQ ID NO 6
<211> LENGTH: 27
<212> TYPE: DNA
<213> ORGANISM: Artificial Sequence
<220> FEATURE:
<223> OTHER INFORMATION: c14_amp02R oligonucleotide

<400> SEQUENCE: 6
gagttgtttg ttattgttgt tgtttgt                                          27

<210> SEQ ID NO 7
<211> LENGTH: 44
<212> TYPE: DNA
<213> ORGANISM: Artificial Sequence
<220> FEATURE:
<223> OTHER INFORMATION: c15_YA4  oligonucleotide

<400> SEQUENCE: 7 gagccgccg ttaccgtcgt tgcttgcttc ggcttcctga gtgt                        44

<210> SEQ ID NO 8
<211> LENGTH: 48
<212> TYPE: DNA
<213> ORGANISM: Artificial Sequence
<220> FEATURE:
<223> OTHER INFORMATION: c15_Hairp06 oligonucleotide
<220> FEATURE:
<221> NAME/KEY: misc_feature
<222> LOCATION: (1)..(1)
<223> OTHER INFORMATION: /replace = "cytosine 5'-phosphate"
```

```
<400> SEQUENCE: 8
nactcaggaa gccgaagcgc tccgatcgag tgttgtctcg atcggagc                48
```